(12) United States Patent
Kramer et al.

(10) Patent No.: US 6,413,229 B1
(45) Date of Patent: Jul. 2, 2002

(54) FORCE-FEEDBACK INTERFACE DEVICE FOR THE HAND

(75) Inventors: James F. Kramer, Menlo Park; Mark H. Yim; Marc R. Tremblay, both of Palo Alto; Daniel H. Gomez, Union City, all of CA (US)

(73) Assignee: Virtual Technologies, INC, San Jose, CA (US)

( * ) Notice: Subject to any disclaimer, the term of this patent is extended or adjusted under 35 U.S.C. 154(b) by 0 days.

(21) Appl. No.: 09/501,015

(22) Filed: Feb. 9, 2000

Related U.S. Application Data

(63) Continuation of application No. 09/076,617, filed on May 12, 1998, now Pat. No. 6,042,555.
(60) Provisional application No. 60/046,185, filed on May 12, 1997, and provisional application No. 60/054,654, filed on Aug. 4, 1997.

(51) Int. Cl.$^7$ ................................................ A61B 5/00
(52) U.S. Cl. ...................................................... 600/595
(58) Field of Search ................................ 600/587, 592, 600/593, 595; 364/413.02

(56) References Cited

U.S. PATENT DOCUMENTS 3,263,824 A   8/1966   Jones et al.
3,919,691 A   11/1975  Noll
3,923,166 A   12/1975  Fletcher et al.

(List continued on next page.)

FOREIGN PATENT DOCUMENTS

WO    WO95/10396    4/1995

OTHER PUBLICATIONS

Atkinson et al., "Computing with Feeling" Comput. & Graphics, vol. 2, pp. 97–103, 1977.

Fisher, "Telepresence master glove controller for detrous robotic end–effectors" SPIE vol. 726 Intelligent Robots and Computer Vision: Fifth in a Series (1986).
Akamatsu et al., "Multimodal Mouse: A Mouse–Type Device with Tactile and Force Display" *Presence*, vol. 3, No. 1, pp. 73–80, Winter 1994.
Eddy, Andy, "Power Glove, Get a Grip on Your Games", Video Games & Computer Entertaining, pp. 18–20, Sep. 1989.
Bergamasco et al. "Advanced Interfaces For Teleoperated Biomedical Robots" IEEE Engineering in Medicine and Biology Society, 11$^{th}$ Annual International Conference, pp. 0912–0913, 1989.
Foley, "Interfaces for Advanced Computing" Scientific American, 257, No. 4, New York, New York, pp. 82–86 and 88–90, Oct. 1987.
Noma, et al., Cooperative Object Manipulation in Virtual Space using Virtual Physics, DSC–vol. 61, Proceedings of the ASME Dynamic Systems and Control Division, pp. 101–106, 1997.

*Primary Examiner*—Max Hindenburg
(74) *Attorney, Agent, or Firm*—Paul M. Thyfault; James Riegel

(57) ABSTRACT

A man-machine interface is disclosed which provides force information to sensing body parts. The interface is comprised of a force-generating device (106) that produces a force which is transmitted to a force-applying device (102) via force-transmitting means (104). The force-applying device applies the generated force to a sensing body part. A force sensor associated with the force-applying device and located in the force applicator (126) measures the actual force applied to the sensing body part, while angle sensors (136) measure the angles of relevant joint body parts. A force-control unit (108) uses the joint body part position information to determine a desired force value to be applied to the sensing body part. The force-control unit combines the joint body part position information with the force sensor information to calculate the force command which is sent to the force-generating device.

20 Claims, 50 Drawing Sheets

U.S. PATENT DOCUMENTS

| | | |
|---|---|---|
| 4,302,138 A | 11/1981 | Zarudiansky |
| 4,414,537 A | 11/1983 | Grimes |
| 4,414,984 A | 11/1983 | Zarudiansky |
| 4,575,297 A | 3/1986 | Richter |
| 4,962,448 A | 10/1990 | DeMaio et al. |
| 4,986,280 A | 1/1991 | Marcus et al. |
| 4,988,981 A | 1/1991 | Zimmerman et al. |
| 5,004,391 A | 4/1991 | Burdea |
| 5,047,952 A | 9/1991 | Kramer et al. ........... 364/513.5 |
| 5,086,785 A | 2/1992 | Gentile et al. |
| 5,143,505 A | 9/1992 | Burdea et al. |
| 5,184,319 A | 2/1993 | Kramer ...................... 364/806 |
| 5,193,963 A | 3/1993 | McAffee et al. |
| 5,316,017 A | 5/1994 | Edwards et al. |
| 5,354,162 A | 10/1994 | Burdea et al. |
| 5,562,707 A | 10/1996 | Prochazka et al. ............. 607/2 |
| 5,587,937 A | 12/1996 | Massie et al. ............. 364/578 |
| 5,631,861 A | 5/1997 | Kramer ...................... 364/406 |
| 5,676,157 A | 10/1997 | Kramer ...................... 128/782 |
| 5,986,643 A | 11/1999 | Harvill et al. .............. 345/156 |
| 6,104,379 A | 8/2000 | Petrich et al. .............. 345/157 |

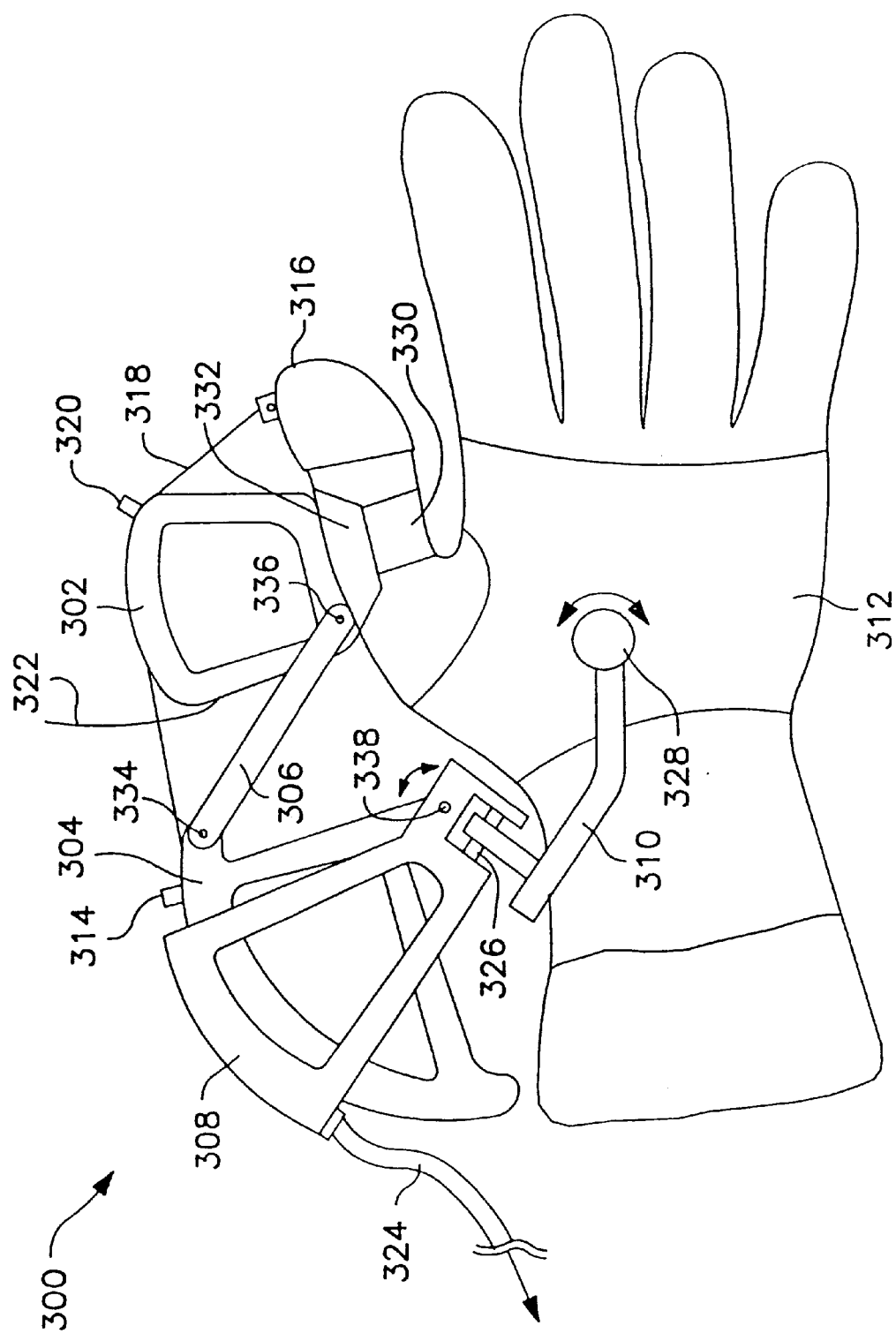

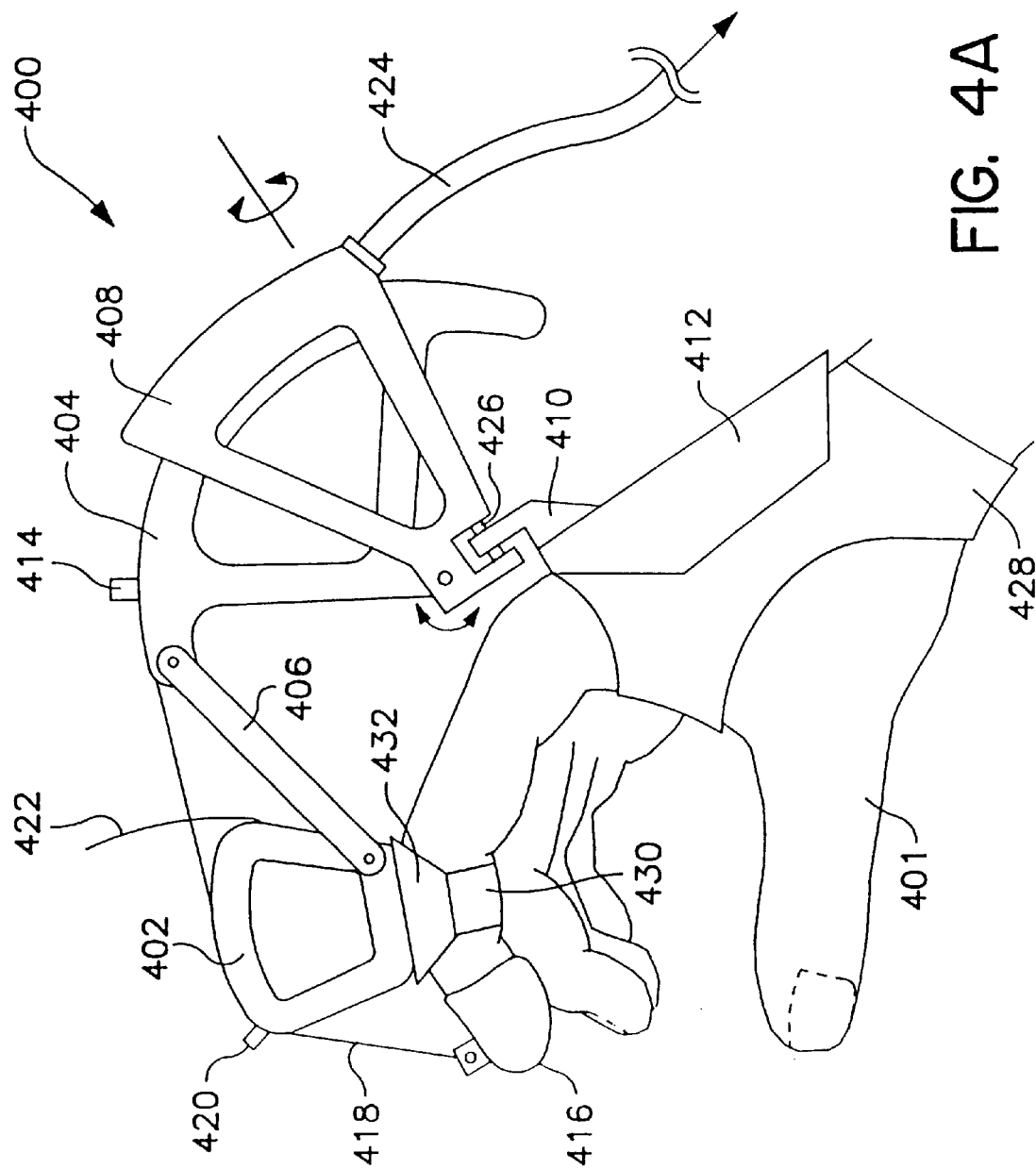

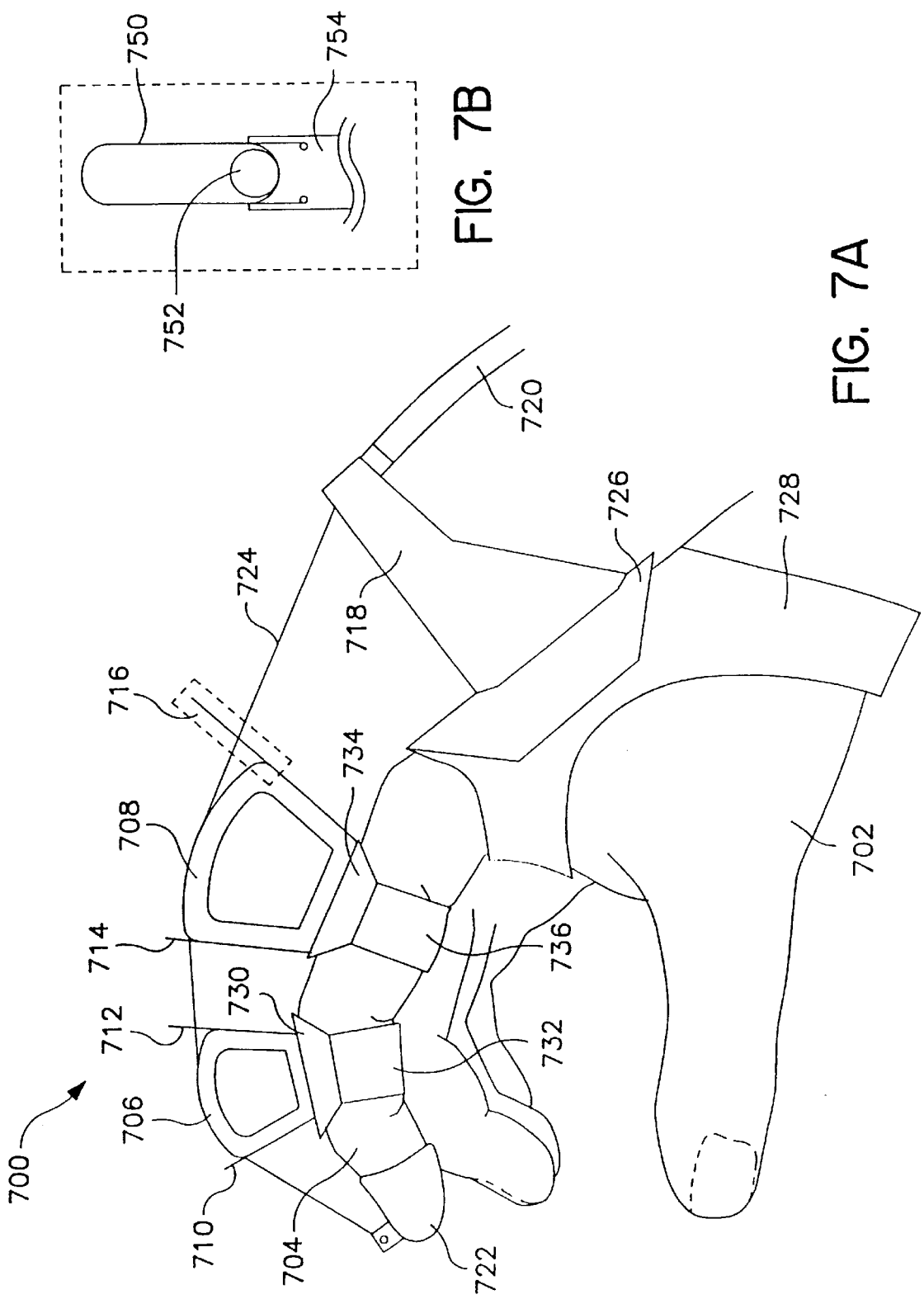

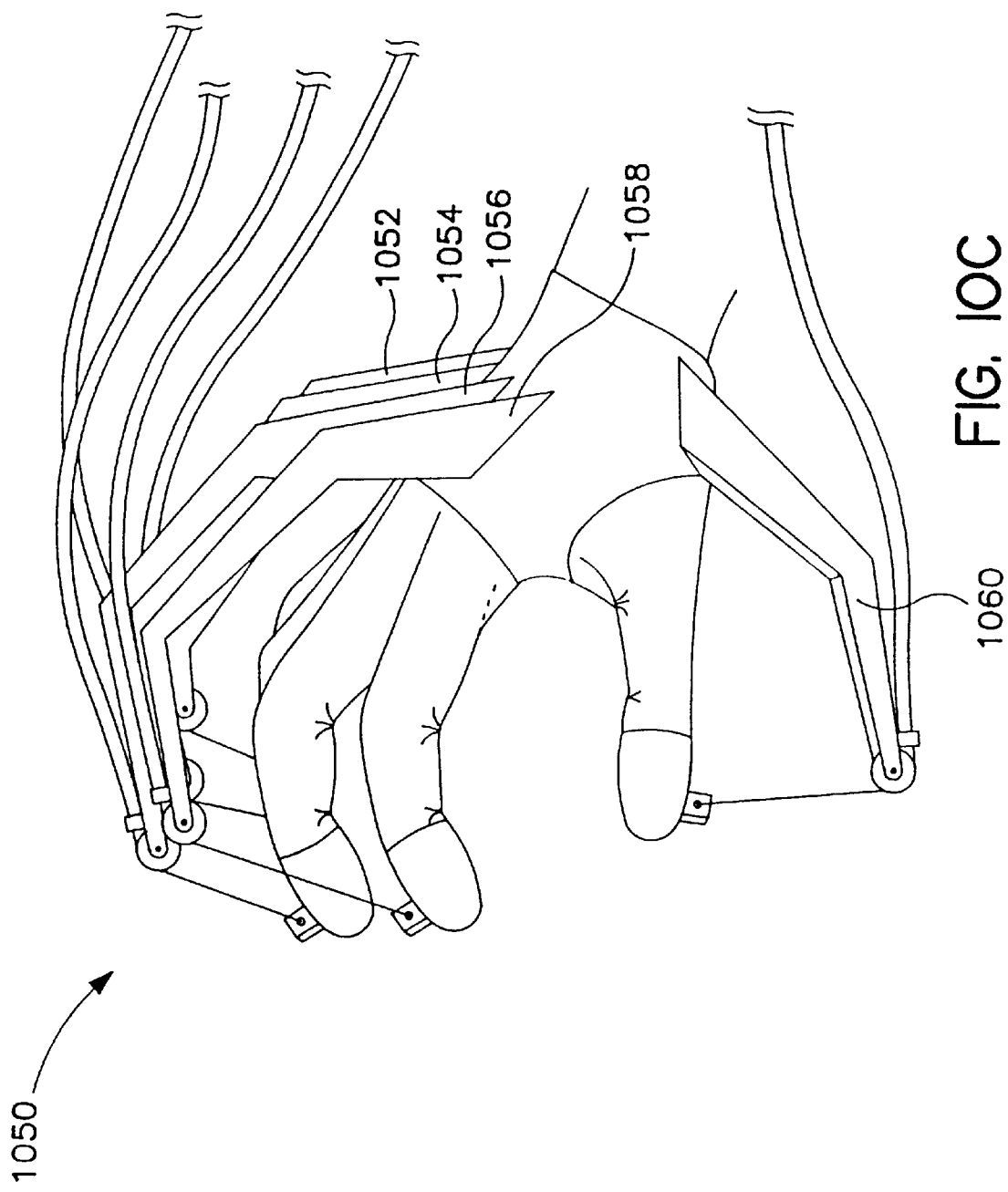

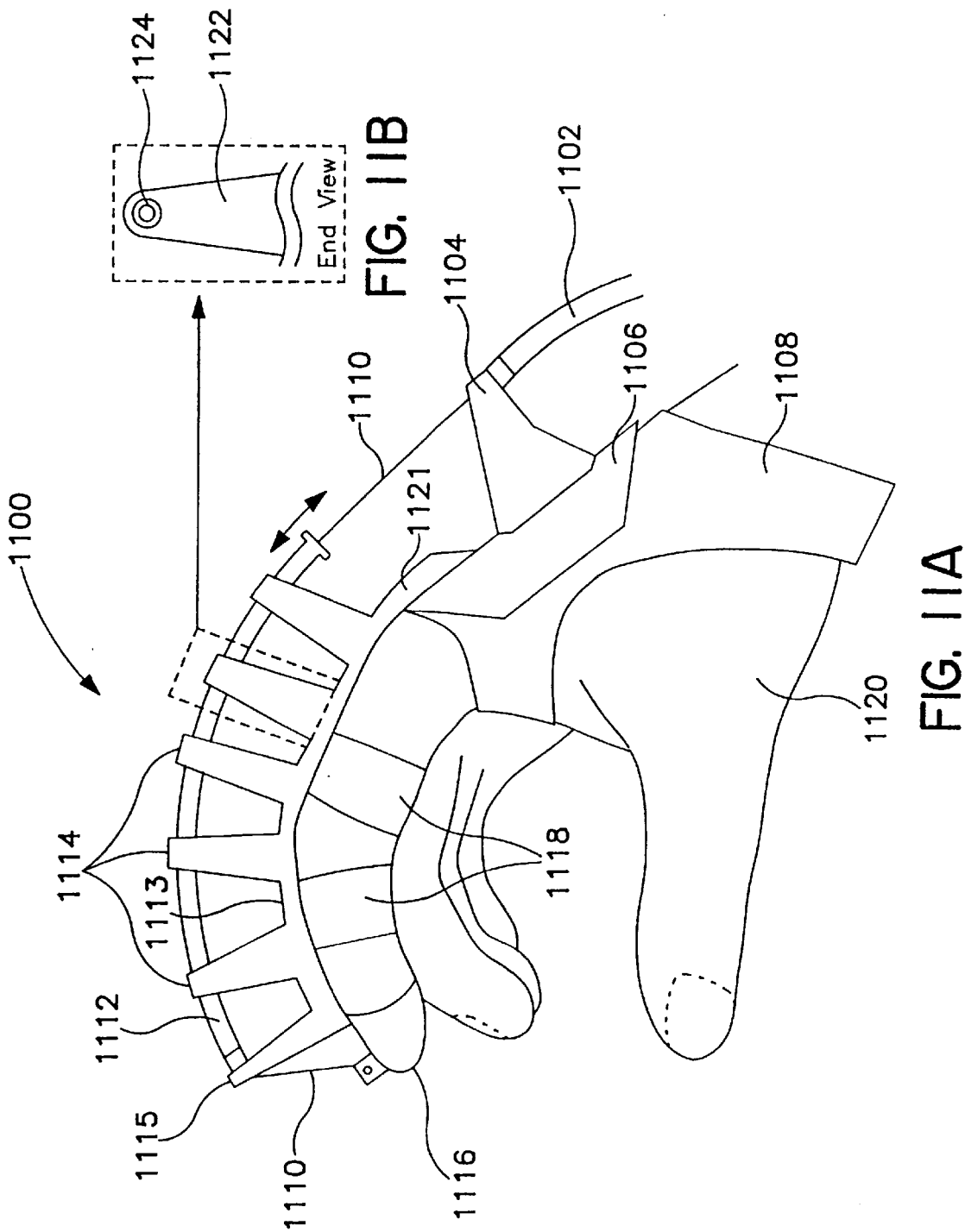

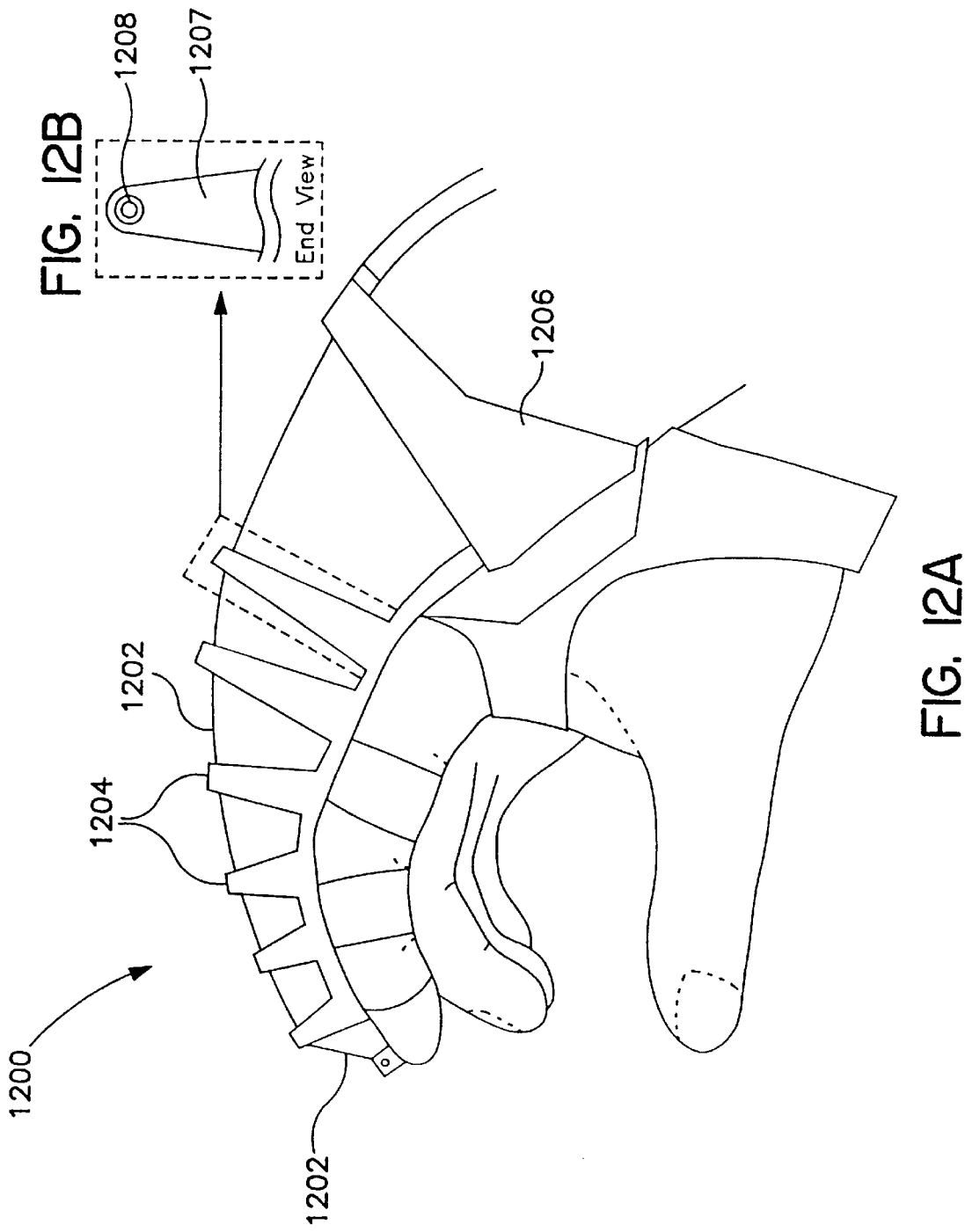

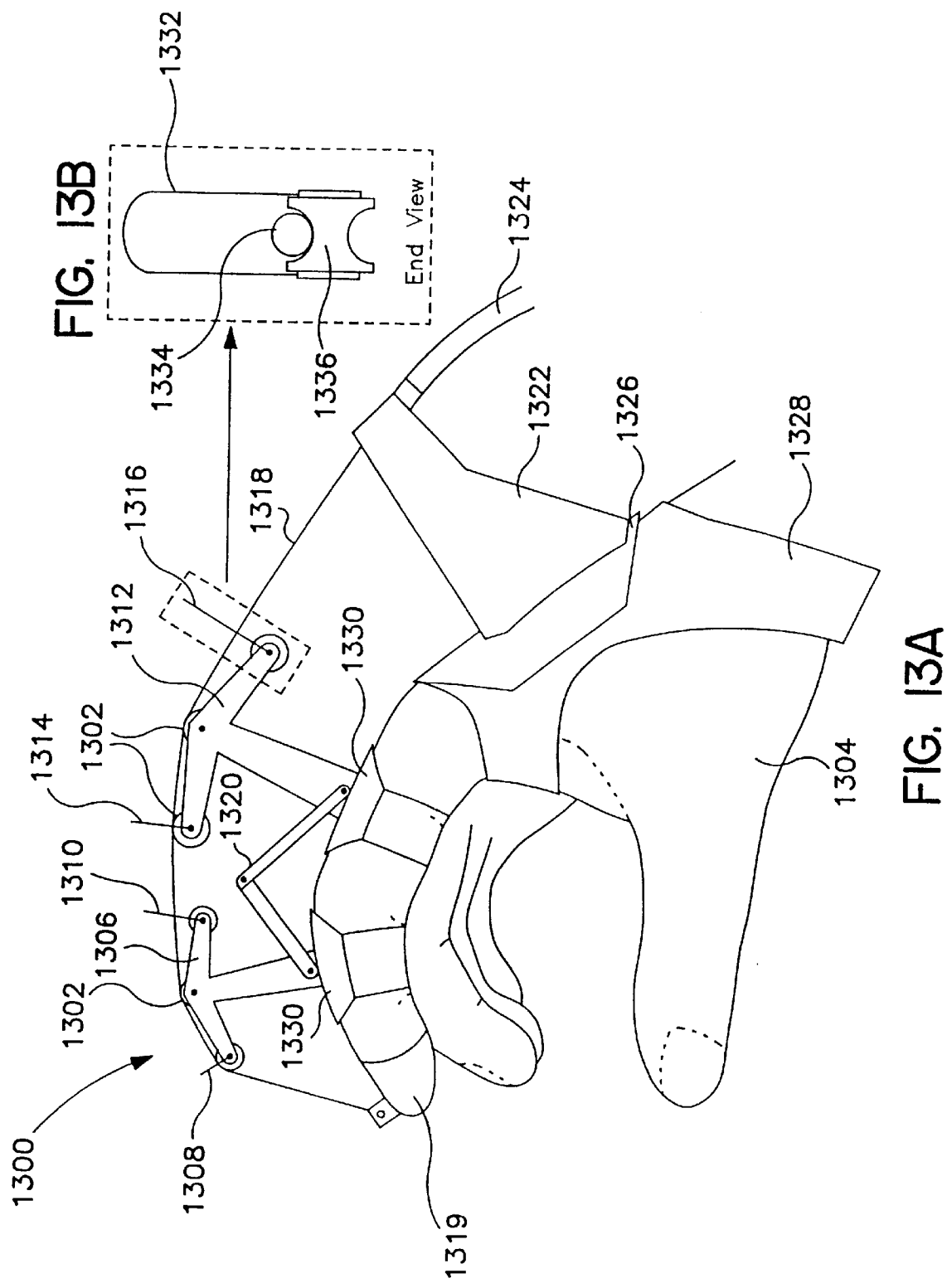

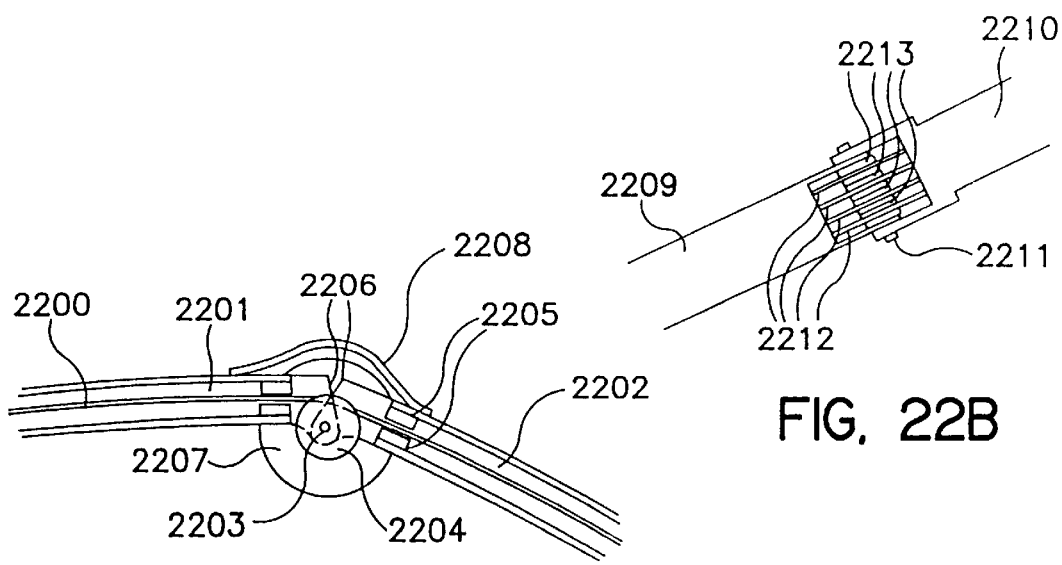
FIG. 22A
FIG. 22B
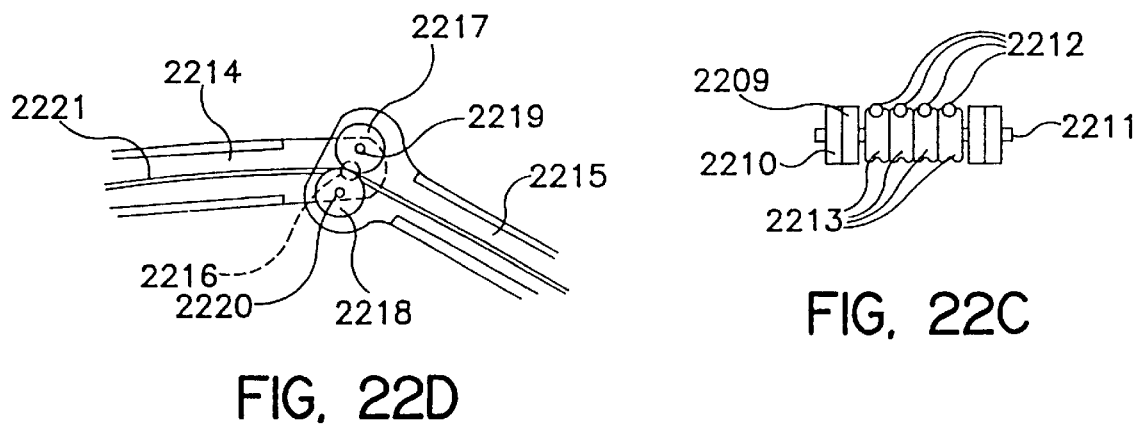
FIG. 22D
FIG. 22C
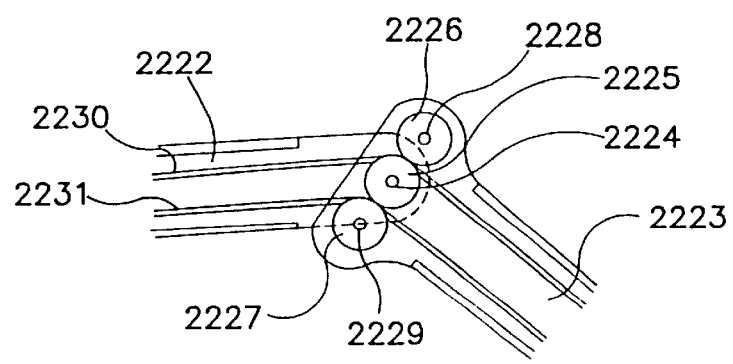
FIG. 22E

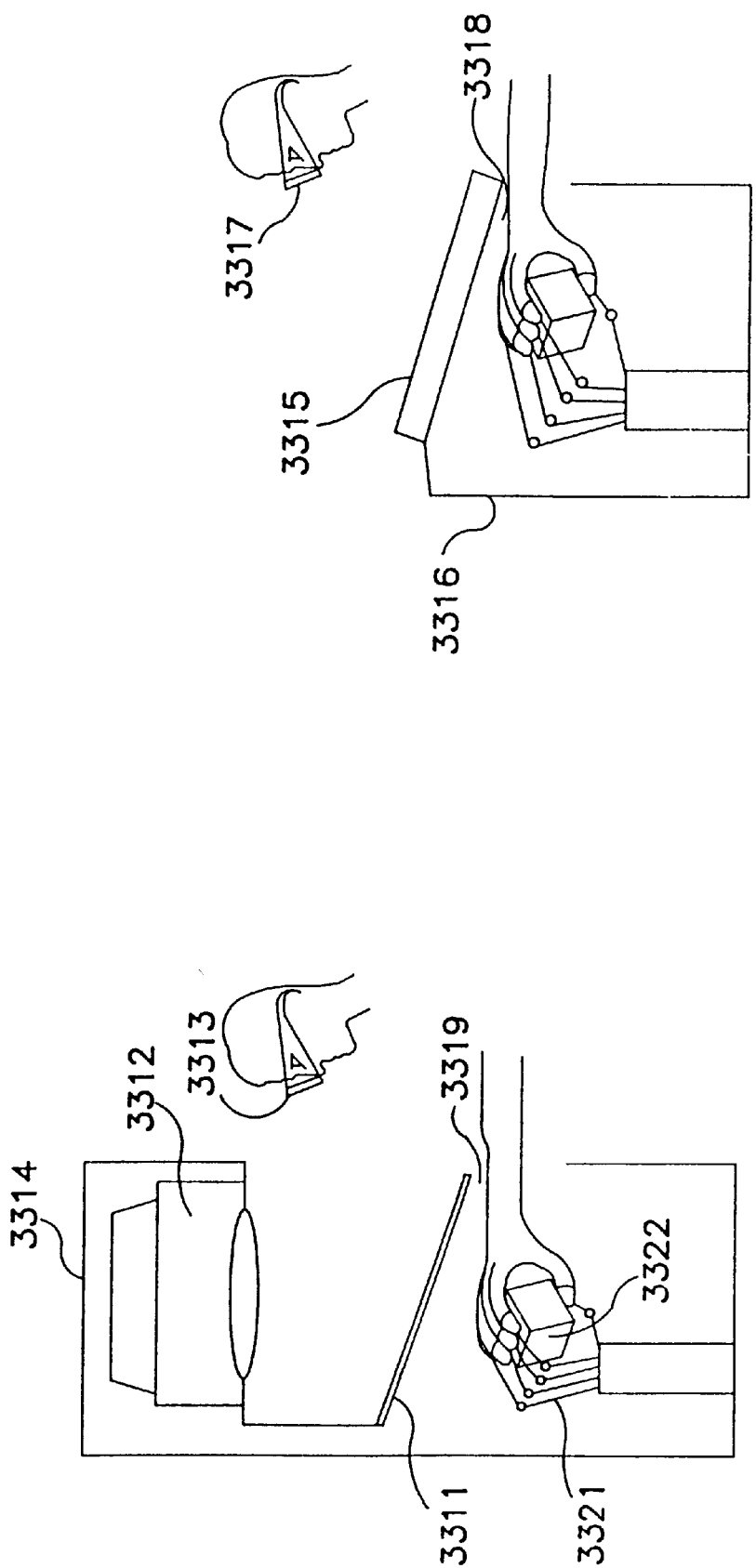

FORCE-FEEDBACK INTERFACE DEVICE FOR THE HAND

CROSS-REFERENCE TO RELATED APPLICATIONS

This application is a continuation of Ser. No. 09/076,617 filed May 12, 1998 now U.S. Pat. No. 6,042,555 which claims benefit of U.S. Provisional Application Ser. Nos. 60/046,185, filed May 12, 1997, and 60/054,654, filed Aug. 4, 1997.

TECHNICAL FIELD

This invention relates to a man-machine interface and in particular to an interface that measures body part positions and provides feedback to a user's hand and arm.

INTRODUCTION

Background

A new manner of computer interaction is now in its infancy. The words "virtual environment" or "virtual reality" will soon be commonplace. A virtual environment is an environment where some portion of the environment is artificially simulated, most often via a computer. A computer may create a graphic simulation of an environment, complete with graphic images of chairs, windows, doors, walls, etc., and even images of other people. The computer may also simulate environmental sounds. The generated objects may be viewed on a common two-dimensional display, such as a computer screen, or, by viewing with special stereoscopic equipment, the objects may be made to appear three dimensional.

The most natural way for an individual to interact in a virtual environment is to directly control a graphical representation of himself. For example, if the individual turns his head, the display screen at which he is looking is appropriately updated. Also, if the individual reaches out and closes his hand, the computer generated image of his hand on the screen reaches out and closes. Such virtual environments have been discussed in the literature.

To create the sensation of virtual reality, the computer should be able to generate and manipulate graphic images of real or imaginary objects in real time. Although generating a graphic representation of an environment may be time consuming and non-trivial to implement, much of the theory has been explored and is well-understood by those skilled in the art of interactive 3-D computer graphics and solid modeling. The invention described here pertains to the important related area in which relatively little research has been done, i.e., "How may a human user perceive grasping force and from his computer-generated counterpart in the virtual environment?"

There are many peripheral devices which have been created to allow a user to enter information into the computer. The most notable of these is the standard QWERTY keyboard. Besides the numerous modifications of this "key input" concept, there are many other devices with their associated permutations. A partial list of such devices includes mice, joy-sticks, trackballs and Computer-Aided-Design (CAD) tablets. The main drawback of these computer input devices is that they don't permit human users to enter information in a manner which may be the most efficient and natural. For example, in a CAD software program, the human designer may wish to rotate a 3-D graphic representation of a block on a computer screen to view and modify the hidden side. Using currently available input devices, the designer must select the axis or a sequence of axes about which the object must be rotated to achieve the desired orientation and view. After the desired axis is selected, the amount of angular rotation must be determined, usually by the linear motion of a mouse or by entering the desired amount of rotation as a decimal quantity via the keyboard. This whole procedure seems very awkward and non-intuitive when compared to what a person would normally do when confronted with a similar task in the "real world," i.e., he would simply reach out, pick up and rotate the object.

Instrumented gloves which provide finger-position information to the computer have been used to manipulate simulated objects in virtual environments. Such gloves have also been used in telerobotics to control highly dextrous end-effectors to grasp real objects. However, lack of force feedback to the glove wearer has reduced the effectiveness of these open-loop manipulation approaches. Imagine a 3-D graphic model of an egg on a computer screen. Suppose you are wearing a glove which maps your finger and hand motions to a graphic image of a hand on the same screen as the egg. As you move your hand and fingers, the corresponding graphic images of the hand and fingers move in a similar manner. The task is to move your own hand and fingers to control the graphic hand on the computer screen to pick up the egg. To accomplish this task you must provide enough force to reliably grasp and lift the virtual egg, but not so much force such that the egg is crushed. Without some kind of grasping force and tactile feedback, this task would be extremely difficult.

Attempts have been made to provide information about simulated contact with virtual or telemanipulated objects to senses other than the corresponding tactile senses. One method of simulated feedback which has been tested uses audible cues. For example, the computer may beep when contact is made. Another simple method is to highlight the object once contact is made. Both these methods will require the user to re-learn hand-eye coordination. It may be frustrating and time consuming for the user to learn one of these "unnatural" methods of grasping an object, and the sensation of interacting in a virtual environment will be reduced.

More recently, approaches have been developed to directly exert forces to the fingertips. One such approach uses pneumatic pistons located in the palm of the hand to exert resistive forces at the fingertips. The disadvantages of such an approach are numerous. First or all, pneumatic cylinders have low mechanical bandwidth and cannot exert very large forces because the limited workspace of the palm limits their size. Additionally, such actuators tend to be noisy and the fact that they are located in the palm limits the range of motion significantly. Other approaches have used servomotors located directly on the back of the hand. Such approaches tend to be quite bulky and often need to be supported by robotic arms and thus are not well suited for desktop applications. When robotic arms are not used, hand and arm fatigue are often a problem as it is quite difficult to produce a device that is small and light enough for prolonged usage. Additionally, such devices often do not provide feedback to all the fingers in an effort to minimize bulk. Finally, such devices typically suffer from a limited range of motion which hinders manipulation.

Therefore, it will be appreciated that there remains a need for a man-machine interface for the hand that is capable of sensing finger and hand positions and hand orientation, that provides appropriate force-feedback, and that overcomes the other limitations in the state-of-the-art as described herein before.

One object of the invention is to provide a man-machine interface which may be employed in interactive computer applications. Another object of the invention is to provide a force feedback control system capable of controlling a set force to a selected part of the body, e.g., the fingertip. et another object of the invention is to provide a man-machine interface comprising a glove capable of sensing finger and hand positions and hand orientation, which may exert, measure and dynamically vary and control the forces applied to each finger. Another object of the invention is to provide a digital control system capable of sensing the force applied to the fingertip and capable of using this applied force signal to control the fingertip force to a desired force set point which may vary as a function of finger position. Still another object of the invention is to provide a force feedback system which may be employed in many different applications, such as virtual environments, telemanipulation and interactive 3-D graphics, telerobotics and Computer Aided Design (CAD). Yet another object of the invention is to provide more natural and intuitive feedback during object/environment interaction.

SUMMARY OF THE INVENTION

The subject invention introduces new techniques for providing grasp force feedback and grounded force feedback to the hand of a wearer. The feedback techniques are largely predicated on transmitting a force from a remotely located actuator to the site of force application via a tendon-in-tendon-guide structure. Various tendon/tendon guide structures are provided, some comprising flexible tendon guides and some comprising rigid tendon guides. In one useful embodiment of the subject invention, the tendons are routed over a series of moment-augmenting structures on the dorsal surface of the hand, where the structure determines the level of moment applied to joints of the hand for a given fingertip force. The structure is typically designed such that a larger moment is applied to the metacarpophalangeal joint than a joint more distal. In another useful embodiment, 5- or 7-bar linkages are used to apply force only to the fingertip relative to a location typically either on the back of the hand or a structure supported by a ground-referenced robotic arm. When used with a ground-reference robotic arm, grasp-force devices become lightweight, low-inertia ground-referenced force-feedback devices.

In one aspect, the inventive structure provides apparatus for attachment to a body where the body has a sensing body link connected to a non-sensing body link with at least one sensing body joint between the sensing and non-sensing body links. The apparatus includes means for applying force to the sensing body link, attachment means for attaching to the means for applying force and to the non-sensing body link, and means for generating a force at the sensing body link and a moment at the sensing body joint. The apparatus also includes means for applying the generated force between the sensing body link and the non-sensing body part. In one embodiment of the inventive structure, the means for applying the generated force includes a moment-augmenting structure (such as for example, towers and cams). The inventive structure also includes a tendon elevated by the moment-augmenting structure, where the tendon is connected at the force-applying means at one end, and to the force generating means at the other end; and tendon guiding means for guiding the tendon between the force-applying means and the force generating means.

In one particular embodiment, the moment-augmenting structure comprises first and second elements connected by an articulated link such that the two elements move in the same plane. In another embodiment, the moment-augmenting structure comprises a composite member of some complexity comprising a flexure-articulating component and an abduction-articulating component, the composite member further comprises two revolute joints, wherein the flexure-articulating component is attached to the abduction-articulating component by one of the revolute joints and rotates relative to the abduction-articulating component, and the abduction-articulating component is attached to the attachment means at the non-sensing body link by means of the other one the revolute joints. In still another embodiment, the moment-augmenting structure comprises a simple member including means for attachment to an intermediate link between the sensing and non-sensing links and a tendon-elevating guide connected to the attachment means.

In another embodiment, the force-applying means includes a platform displaced from the sensing body link when in an unactivated position and in contact with the sensing body link when in an activated position. In still another embodiment, the apparatus may include a second force generating means connected to the apparatus for providing force to the apparatus relative to a reference point off the body.

In one embodiment of the inventive method for use in a device for attachment to a body having a sensing body link connected to a non-sensing body link, includes the steps of: applying force to said sensing body link; attaching the body to the force-applying means and to said non-sensing body link; generating a force at the sensing body link and a moment at said sensing body joint; and applying the generated force between the sensing body link and the non-sensing body part; the step of applying the generated force comprising applying the force via a moment-augmenting structure and a tendon elevated by the moment-augmenting structure, where the tendon is connected to receive the generated force at one end and to apply the applied force at the other end; and guiding the tendon between the force-applying means and the force generating means.

A control system and method that senses the force applied to the fingertip; and controls the fingertip force to a desired force set point in response to the sensed applied force signal, where the desired force set point may varying as a function of finger position, is also described.

In one aspect, the invention provides for the use of a flexible housing which may comprise one or more concentric flexible casings which guide a force-transmitting flexible elongated element such as a flexible, low friction/stiction, high modulus of elasticity thread or a shape-memory alloy wire which serves as a tendon and is used in tension to apply force to a sensing body part. In another aspect, the invention provides for the use of force actuators to generate force which is transmitted to the sensing body part via flexible tendon cables, or pneumatic or hydraulic tubes, and used by a force applicator to apply force to the sensing body part. In still another aspect, the invention provides for the use of a support to which the flexible tendon cables or tubes are secured. The support may be a reinforced wrist-strap when the sensing body part is part of the hand. In yet another aspect, the invention provides for the use of a mechanical structure to augment the mechanical moment and which is attached to the back of the hand to route force applying tendons to each of the fingertips without hindering hand movement and exerting resistive forces at the fingertips as well as resistive torques at the finger joints. In a further aspect, the invention provides for the use of a pressure, tension and/or force sensor to measure the force applied to the force-sensing body part by the force actuator.

Additional objects, features, and advantages of the inventive system, apparatus, and method will be more readily apparent from the following detailed description and appended claims when taken in conjunction with the drawings.

BRIEF DESCRIPTION OF THE DRAWINGS

Additional objects and features of the invention will be more readily apparent from the following detailed description and appended claims when taken in conjunction with the drawings, in which:

FIG. 3 is a diagrammatic illustration showing a side view of the mechanical structure of a thumb-controlling force-feedback device.

FIG. 4A is a diagrammatic illustration showing a side view of the mechanical structure of an index-finger-controlling force-feedback device;

FIG. 7A is a diagrammatic illustration showing a side view of another alternative embodiment of the mechanical structure of an index-finger-controlling force-feedback device; and FIG. 7B shows an end view of an individual tendon guide.

FIG. 10C shows a perspective view of the mechanical structure of an whole-hand-finger-controlling force-feedback device using one tower structure per finger.

FIG. 11A is a diagrammatic illustration showing a side view of another alternative embodiment of the mechanical structure of an index-finger-controlling force-feedback device; and FIG. 11B shows an end view of an exemplary individual tendon guide.

FIG. 12A is a diagrammatic illustration showing a side view of another alternative embodiment of the mechanical structure of an index-finger-controlling force-feedback device showing towers of varying heights;

FIG. 12B shows an end view of an individual tendon guide; and

FIG. 13A is a diagrammatic illustration showing a side view of another alternative embodiment of the mechanical structure of an index-finger-controlling force-feedback device showing towers of varying heights; having connecting links; and FIG. 13B shows an end view of an individual tendon guide;.

FIGS. 22A–22E are diagrammatic illustrations showing various pinned joints which may be employed when routing a tendon 2200 from the actuator to its desired final destination;

FIG. 29 is a diagrammatic illustration showing a force- and position-programmable robotic arm which may be used as a macro-manipulator, or as a grounded-force device which attaches to the grasp-force device of FIG. 1, and the like;

FIGS. 33A–33D are diagrammatic illustrations a canonical force-feedback system, representing any of the force-feedback embodiments described in the subject application, being used with a 3D display system;

DESCRIPTION OF SPECIFIC EMBODIMENTS

Figure 1:
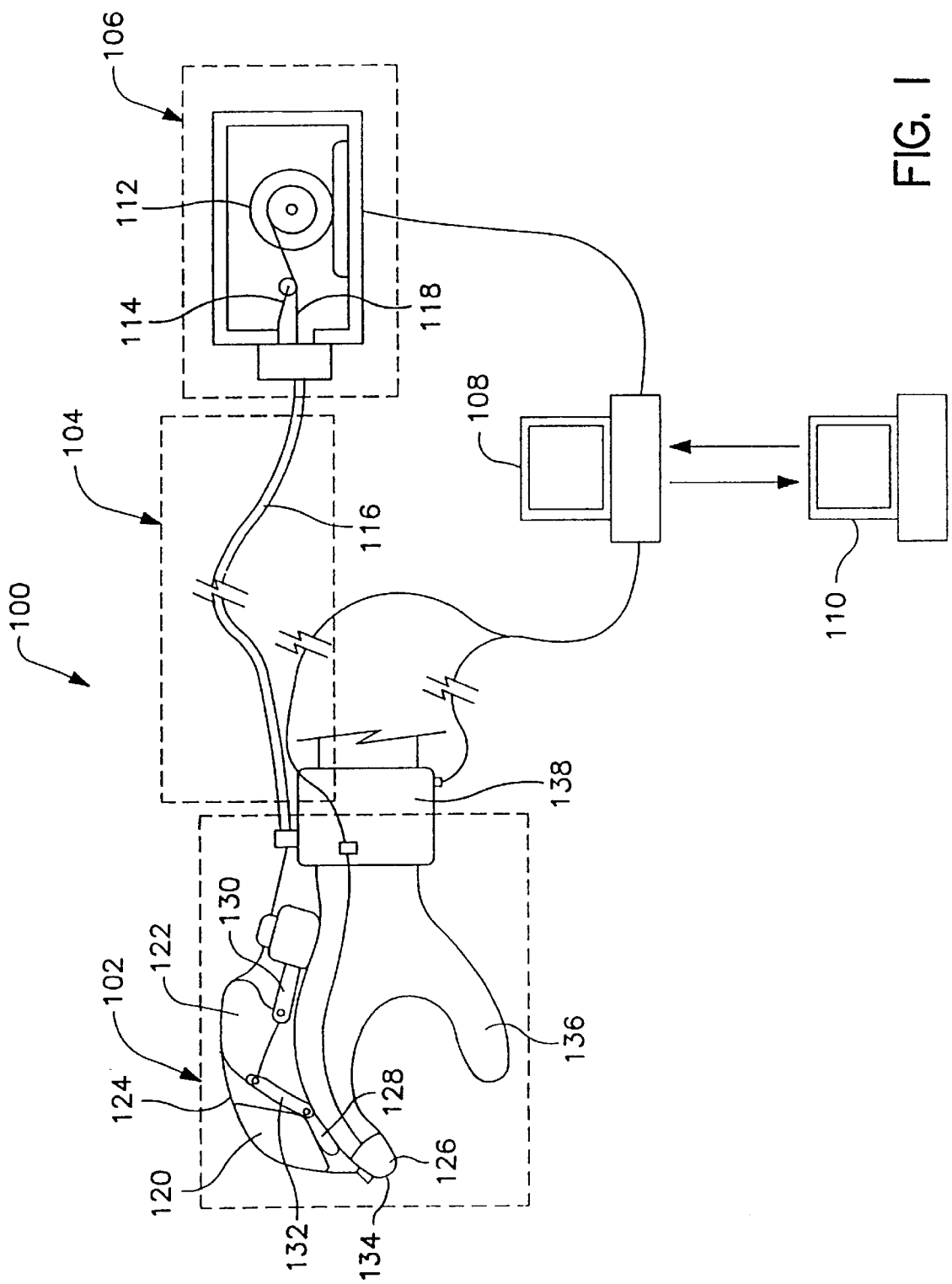
FIG. 1 is a diagrammatic illustration of an exemplary embodiment of a system employing the force feedback structure mounted atop an instrumented glove that measures the position of the hand in conjunction with the controlling components.

Reference will now be made in detail to the specific embodiments of the invention, which are illustrated with reference to the accompanying figures. We begin with an overview of some features of the inventive structure and method and then describe particular inventive features with reference to exemplary embodiments illustrated by the accompanying figures.

One embodiment of the invention provides the use of a glove incorporating not only sensors which provide analog values representing finger and overall hand motion, but also true force feedback to the wearer's fingertips relating the amount of force a corresponding graphic (or actual) device is applying to a given virtual (or telemanipulated) object.

The invention, which senses one or more body part positions and provides force feedback to one or more body parts, permits a relatively "natural" method of computer interaction. The subject device provides for: (1) controlling body part position-sensing means employing a plurality of signal-producing means associated with individual movable controlling body parts, where the signal is related to controlling-body-part position, with the individual signals analyzed to define a composite signal; where the signal-producing means may be anything which provides body part position and/or orientation, mechanical, electrical or optical, including strain gage, electromagnetic, ultrasonic, piezoelectric, Hall effect, infrared emitter/detector pair, encoder/potentiometer, laser scanning or other position and/or orientation sensors; (2) force-applying means which may be anything which provides force information to a sensing body part; (3) force-sensing means which may be anything which provides a force-measurement signal; (4) force-generating means which may be any actuator which generates a force (or displacement), including electrical, electromagnetic, electromechanical, pneumatic, hydraulic, piezoelectric, shape memory alloy (for example, Nickel/Titanium alloys), vapor pressure actuators, and the like; (5) force-transmitting means (for example, a tendon/sheath assembly, exemplified by a flexible, inelastic tendon guided by a flexible, incompressible housing, or a hydraulic assembly exemplified by an incompressible fluid guided by an inelastic housing), which may be anything which transmits a force signal from a force-generating means to an applying means (for example, a force-applying means); (6) signal-collection and producing means (for example, a processor or computer) for collecting signals (for example, from the position-sensing and/or force-sensing means) and producing signals (for example, for the force-applying means); and (7) support structure (including clips, straps, clamps, guides, cams, rollers, pockets, material, and the like) used to support the body part sensing means, the force-applying means, the force-generating means, the force-transmitting means and the signal collection and producing means and attach the various components in their operative organization to the body part.

The signal associated with the controlling-body-part position-sensing means may be coordinated with the force applied to a sensing body. For example, the signal produced by the controlling-body-part position-sensing means may be used by a signal-collection and producing means to manipulate a multi-articulated computer-generated interactive entity in a virtual environment. The force-applying means may apply force to a sensing body part in relation to the interaction between the interactive entity and a component of the virtual environment to further enhance the sensation of reality.

A particular application for the invention is to sense and provide force feedback to the hand. A useful embodiment for the invention when used for the hand includes a "feedback glove." The feedback glove embodiment comprises means for measuring position and orientation of the hand in space relative to a given reference, means for measuring individual joint angles, means for applying force to various parts of the hand and desirably means for sensing the applied force. Many of the specific descriptions of the invention will be centered around the feedback glove, however, the sensing and structures described for the glove may be translated to other body parts (e.g., arms, legs, feet, head, neck, waist, etc.).

In one embodiment of the feedback glove, the means for providing position and orientation of the hand in space is a Polhemus™ or Ascension™ electromagnetic position sensor. The individual joint-angle-sensing means comprises two long, flexible strain gages mounted back to back. The strain gage assemblies reside in guiding pockets sewn over each joint. When a joint is flexed, one of the strain gages of the corresponding pair of gages is in tension, while the other strain gage is in compression. Each pair of two strain gages comprise the two legs of a half bridge of a common Wheatstone bridge configuration. An analog multiplexer is used to select which of the half bridge voltages is to be sampled by an analog-to-digital converter. The maximum strain experienced by each gage is adjusted by varying the thickness and elastic modulus of the backing to which the gages are mounted. The backing is selected to maximize the signal output without significantly reducing the fatigue life of a gage. These joint angle strain gage sensors are disclosed in the Kramer et. al. U.S. Pat. No. 5,047,952 and are incorporated herein by reference.

Means for applying force to parts of the hand comprises means (e.g., an electric motor or a hydraulic actuator) for generating a desired force, means (e.g., a flexible tendon/casing assembly) for transmitting the generated force to force-applying means, and means (e.g., a force-applying platform) for transferring the force to a specific part of the hand (e.g., the fingertip). The feedback glove may also comprise a means (e.g., a force-sensing platform or load cell) for measuring the applied force. The embodiment includes structure which supports the tendons and casings, usually at least at their ends, and also supports the force-applying means.

The force-feedback glove embodies joint angle sensors and the force-feedback apparatus. The force-feedback glove overcomes many of the problems of joint sensing devices which do not incorporate force feedback. The force feedback glove simulates contact and grasping information in a "natural" manner to a user and facilitates many tasks, such as those arising in interactive 3-D graphics and telerobotics. The force-feedback glove may be used to feed back force information from "virtual" objects in a virtual environment or from remote "real" objects when used in telerobotic applications.

When used with appropriate animation and control software, the force-feedback glove provides joint-angle sensing and sufficient force feedback for a user to control an interactive entity, such as a computer-generated graphic representation of his/her hand to reliably grasp a virtual object, such as a cup, or any object which appears as a graphic model on a display device. Some virtual objects are programmed to demonstrate physical properties similar to real objects, such as weight, contour, stiffness and friction. These, and other features, may be sensed and the virtual objects manipulated using the force-feedback glove. The force feedback incorporated into the glove relays the virtual grasping force information to the user when he "touches" virtual objects with his own computer simulated virtual fingers.

The force-feedback glove, which provides joint angle sensing and force feedback, may also be used for telerobotics. For this application, the force-feedback glove provides joint angle information which is used to control an interactive entity, such as a robot manipulator, to grasp a remote real object. The force feedback of the glove provides the user with information about the actual grasping forces experienced by the robot's gripper, or robotic hand, such that the real object may be more reliably grasped and manipulated with reduced likelihood of dropping or crushing.

The glove employing force feedback may also be programmed to teach finger dexterity, finger timing and even the motions necessary to learn some musical instruments. For example, if the user were learning the piano, as fingers are flexed, the user would receive fingertip pressure from virtual keys signifying to the user that he had pressed the key. Tendons similar to those positioned on the dorsal side of the fingers to restrict finger flexure may also be placed on the palm side of the hand. These palm-side tendons may be used to force the fingers into the desired flexed positions or to restrict the fingers from extending. These tendons would be used in the case when the user wanted to be "taught" to play the piano and wanted his fingers to be properly positioned and flexed for him at the proper times. The idea of this example may be extended from a virtual piano to other virtual instruments and even to other devices such as a virtual keyboard. The feedback glove could be used to teach someone to type, and when learned, to allow the user to generate text by "typing in the air."

More specifically, the invention is a man-machine system which, in addition to measuring actual human joint angles, provides one or more feedback sensations to the user. While the subject device finds primary application with a human, the device may be used with other animate vertebrates, such as other primates, where the vertebrate has an appropriate body part. In one embodiment, a small device is attached to the fingertip of a joint-angle-sensing glove and holds a force-applying platform in juxtaposition to the fingertip (see, for example, U.S. Pat. No. 5,631,861, for the described embodiment, as well as alternative embodiments.) The force-applying platform is displaced from the fingertip (by about 4 mm) by a retractable means (e.g., a leaf spring) when inactivated, but is capable of quickly contacting the fingertip and applying a dynamically selectable force when activated. The sudden impact of the force-applying platform provides a sensation similar to that perceived when the actual fingertip contacts an object. Thereafter, the force-applying platform presses against the fingertip with a programmable force which may relate the amount of force that a virtual finger is pressing against a virtual object.

In another embodiment, the force that is applied by the force-applying platform to the fingertip is transmitted from a force-generating actuator (a DC servo motor) via a high tensile strength, flexible tendon enclosed in a flexible, non-compressible tubular casing. The function of this assembly is similar to a bicycle brake cable. Other embodiments may employ force actuators based on electrical, electromagnetic, electromechanical, pneumatic, hydraulic, piezoelectric, shape-memory-alloy (e.g., Nickel/Titanium alloys), vapor pressure, or other suitable technologies. In choosing the appropriate actuator technology, various factors will be considered, such as speed of response, force output, size, weight, cost and power consumption.

One end of the tendon casing is secured near the force actuator and the other end is secured to a support on the glove itself, such as on the dorsal side of the metacarpus, or to a wristband near the feedback glove. As a tendon emerges from the end of the casing secured to the force feedback structure or exoskeleton, it is routed by a guiding means, e.g., grooved cams, until the tendon reaches its designated final location, for example, the force-applying platform at the fingertip. Tendons which are to provide a force to restrict the wearer from flexing a finger are guided across the dorsal or palmar side of the hand to the final location. In addition, a tendon may be terminated at any properly reinforced intermediate glove location.

As tension is increased, tendons which pass along the mechanical structure of the device, exert a force on the mechanical structure, which in turn exerts a force against the underlying finger. This force, in combination with the force at the fingertip, produces a resistive torque at the finger joints.

To provide a force to restrict the wearer from extending a finger or to actually drive a finger into a flexed position, tendons are guided across the palm side of the glove by sections of casing. In one embodiment, these tendons are guided to the fingertip where they are ultimately secured to a force-applying platform, but they may also terminate at properly reinforced intermediate positions. Unlike the case where the tendons are guided along the back-side of the hand, when the tendons which are guided along the palm-side of the hand are in tension, they tend to pull the casing sections (and hence the glove material) away form the hand. Although not necessary, if it is desired to guide these tendons along the surface of the palm and fingers as they pass from where the casings are secured to the wristband to their final designated locations, the glove must be appropriately reinforced between each joint. (See for example, U.S. Pat. No. 5,631,861.) Alternatively, one may provide a mechanical structure which, much like the structure on the back side of the hand, will guide the tendon away from the palm, thus producing larger torques at the finger joints for the same force at the fingertip, as compared to the embodiment described in the aforementioned patent.

Where the tendons are routed and where they are ultimately secured to the glove will determine the forces applied to the hand by the tendon. Forces and torques applied to parts of the hand by a single tendon may not be controlled independently. Only the force applied to one part of the hand or the torque applied by the tendon to an individual joint may be controlled. In a preferred embodiment, the tendons are fastened to the force-applying platforms at the fingertips, and the forces at the fingertips are measured and controlled, not the torques applied to the joints. To isolate the force and independently restrict motion of a single intermediate joint, a separate tendon is used. Its casing is secured just prior to the joint, and the tendon is fastened to a force-applying platform just beyond the joint.

In a preferred embodiment, the actual force at the fingertip is sensed and fed back to a servo control system. The control system controls the output of the force actuator such that the force applied to the fingertip follows a desired force profile. The force profile for any finger is a function which produces a desired-force set point for any given finger and hand position. That is, as either the finger or hand changes position, the force applied to the fingers varies accordingly. For example, a force profile may be generated which simulates the force sensation of a push button switch that gradually increases its opposing force as the button is depressed until it reaches its toggle point, clicks, and releases most of its resistive force.

The devices provided in the subject application may also be used with various other feedback-signal-generating devices, such as air bladders for pressure feedback, heat and cold-generating devices, tactile-feedback generating devices, force-applying platforms, and the like. Such other feedback-signal-generating devices may be used as are found in Kramer U.S. Pat. Nos. 5,184,319 and 5,631,861, which patents are incorporated herein by reference. In addition, the force-generating devices described herein may conveniently be replaced by brakes, clutches, ratchets, and the like, as appropriate.

Attention is now directed to the specific embodiments illustrated in the figures. In FIG. 1, there is illustrated an overview of the system and method employing the force-feedback device as applied to a hand. The system 100 comprises a force-applying means 102 (indicated by the box designated by broken lines) mounted on a hand wearing an instrumented glove 136, a force-transmitting means 104, a force-generating means 106, a force-control unit 108 communicating with a host computer 110. The force-generating means 106 comprises an actuator 112, conveniently an electric motor, and desirably a tendon tension sensor 114. The actuator 112 may incorporate a position sensor for closed-loop control purposes. The force-transmitting means 104 comprises a tendon casing 116 and tendon 118, shown exposed at both ends of the casing 116. The force-applying means 102 comprises a moment augmenting means or structure 103, such as for example, a mechanical superstructure having tendon-guiding cams 120 and 122 which route the exposed tendon 124 to the force applicator 126, located at the fingertip. Various cam contours may be selected to provide desirable joint-moment vs. joint-angle mappings. The front and rear cams 120 and 122 are mounted to front and rear supports 128 and 130, respectively, and are attached together by connecting link 132. The force applicator may contain a force sensor for closed-loop force or impedance control at the fingertip. The front and rear cam supports 128 and 130 are mounted over the instrumented glove 136. The glove 136 has a wrist strap 138 which serves to anchor one end of the tendon casing 116. This strap can also be located on the metacarpus. The force control unit 108 comprises a processing unit, which has the necessary hardware and software to control the actuator 112 to which it is operatively connected. The force control unit 108 will also detect the signals from the force sensor 134 and the tendon tension sensor 114, and the actuator position sensor, if present. The force control unit also communicates with a host computer 110, where the computer simulation resides or which controls a robot.

By elevating the tendon off the surface of the finger instead of routing it closer to the surface, it is possible to exert larger resistive torques at the finger joints for an identical tension in the tendon. The mechanism transmits the tendon forces to the force applicator 126 at the fingertip while simultaneously exerting reaction forces to the hand via the cam supports 128 and 130. These reaction forces produce reaction torques at the finger joints that prevent the wearer from flexing the finger. The system is shown with a single force-applying means, but the device may include a plurality of force-applying means, such as one for each finger and/or for one or more joints. These force-applying means consist of an individual force-producing means, force-transmitting means and force-generating means, so that each fingertip and, when appropriate, each joint can be individually controlled. The force-control unit monitors the signals received from the various sensors to ensure that the forces exerted on the hand conform with the desired forces.

Figure 2A:
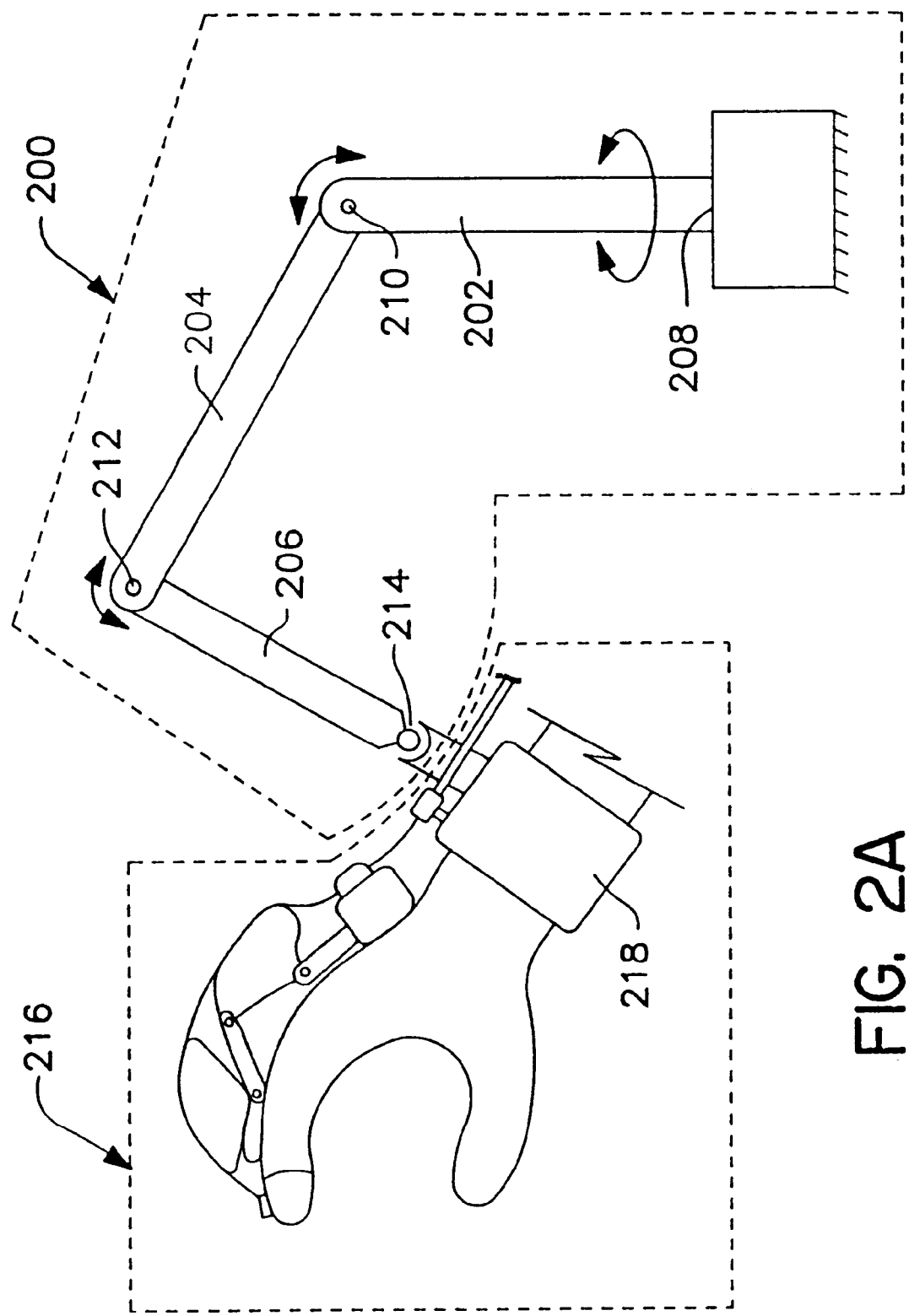
FIG. 2A is a diagrammatic illustration showing a side view of an exemplary embodiment of a force feedback device attached to a reference point off the body (ground)

In FIG. 2a a portion of the system depicted in FIG. 1 is shown in conjunction with a grounding device capable of referencing the hand forces to the physical world, as also depicted in U.S. Pat. No. 5,631,861, the contents of which are incorporated in their entirety herein by reference as if explicitly included. The grounding device 200 (indicated by the box designated by broken lines) is an articulated force-generating apparatus of which there are many possible embodiments. As depicted in FIG. 2, the device comprises articulated linkages 202, 204 and 206, with revolute or prismatic joints 208, 210 and 212, which may comprise associated actuating and sensing means. Articulated interface 214 serves to connect the grounding device 200 to the hand-force-feedback device 216 (indicated by the box designated by broken lines) at the wristband 218, although it may be attached at other sites, such as the back of the hand or the palm. The articulated interface 214 may comprise position sensors capable of measuring the position and orientation of the hand-force-feedback device 216 relative to the grounding device 200. Additionally this interface may be activated to provide up to an additional three degrees of freedom of force feedback, for a total of six or more. In operation, a force-control unit, substantially as described above in FIG. 1, will control the force or torques exerted at the individual joints and also read all corresponding position sensors, including the ones at the articulated interface. As the physical hand moves, the grounding device 200 can be controlled such that it tracks the hand's movement without exerting forces on the hand until such forces are desired by the host computer. When the virtual hand interacts with a virtual object, or a robot interacts with a physical object, the grounding device combined with the hand force feedback device will exert corresponding forces on the arm and hand.

Figure 2B:
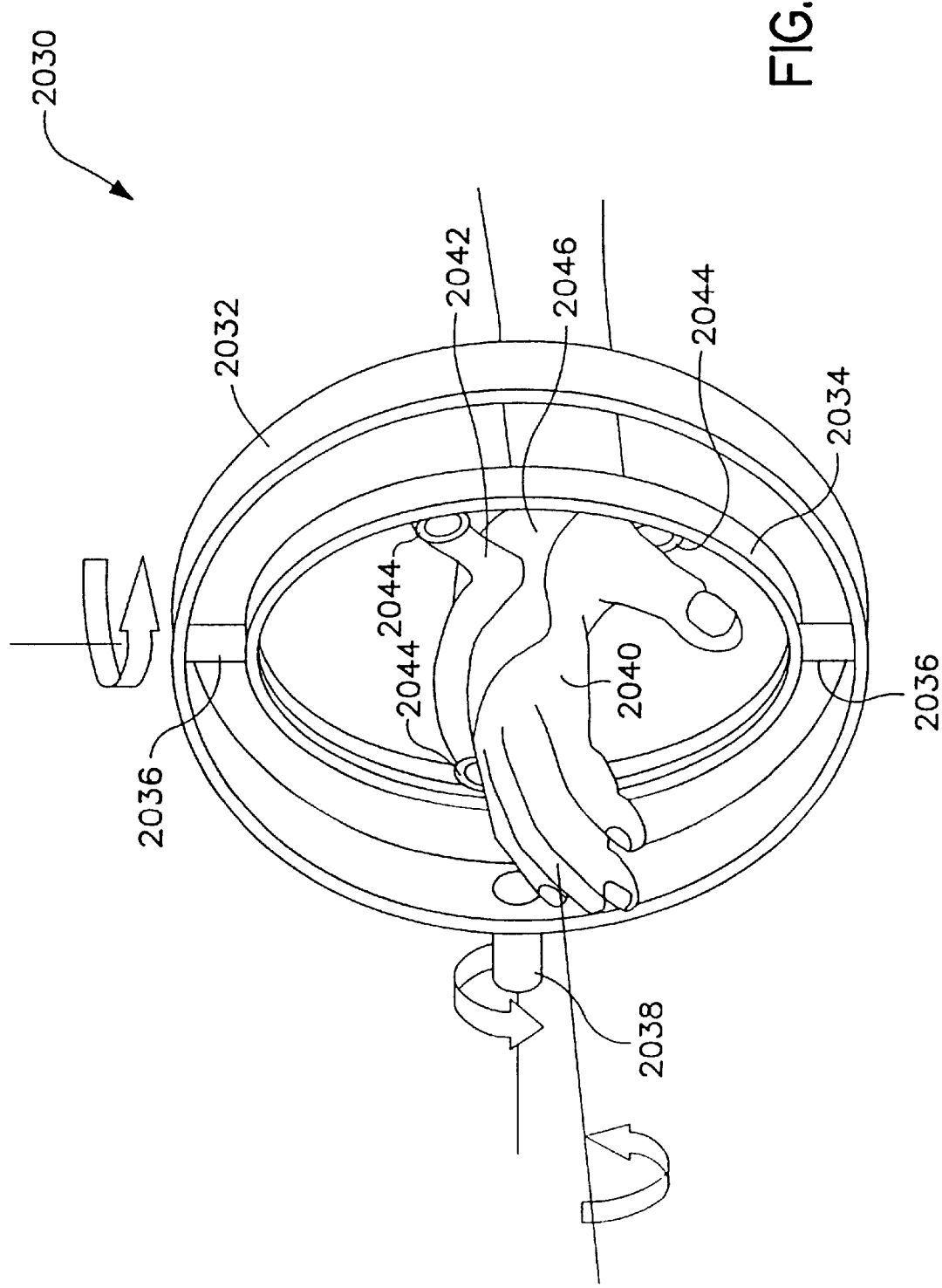
FIG. 2B is a diagrammatic illustration showing a perspective view of an embodiment of the articulated interface that connects the force-feedback device to a reference point off the body (ground)

FIG. 2b is a perspective view of a more detailed illustration of the embodiment of the articulated three degree-of-freedom interface described in FIG. 2a. It consists of two concentric rings 2032 and 2034. The smaller of the two rings 2034 is attached to the larger ring 2032 via pivot joints 2036 such that the inner ring 2034 can rotate inside, and with respect to, the outer ring 2032. The pivot joints are equipped with bearings, bushings or any other suitable means which provide minimal rotational friction. This comprises the first degree-of-freedom of rotation of the interface 2030. It should be noted that for the outer ring, a half-ring and even a quarter ring can also be used. If a quarter-ring is used, one of the pivot joints 2036 is not omitted. The outer ring 2032 is attached to the grounding device described in FIG. 2a via a pivot joint 2038. This comprises the second degree-of-freedom of rotation of the interface 2030. A variety of materials can be used to produce stiff yet light rings such as, but not limited to, titanium, graphite, carbon fiber, aluminum, steel and rigid plastics. Inside the inner ring 2034 resides an attachment 2042 which serves to affix the interface 2030 to the backplate 2046 of the force-feedback means which is the main subject of this invention. For clarity, the force-feedback means is omitted. The attachment 2042 is connected to the backplate 2046 using any convenient means such as a thumb screw, clamp or the like, in order to facilitate attaching/detaching it from the backplate 2046. The backplate is attached to the hand 2040 by any convenient means, such as straps, belts or the like. The attachment 2042 interfaces with the inner ring via a set of three or more wheel-like rotational mechanisms 2044. These rotational mechanisms let the backplate 2046 rotate with respect to the inner ring 2034 and form the third degree-of-freedom of rotation of the interface 2030. It is desirable to add a sensing means to each of the degrees-of-freedom in order to determine the orientation of the hand in space. These sensing means may include, but are not limited to, encoders, potentiometers, Hall-Effect sensors and the like. Greater details of such an implementation are given in FIG. 2c.

In operation, the articulated interface 2030 acts as a three degree-of-freedom revolute joint with angular position measuring capabilities and it transmits forces from the grounding device to the force-producing means located on the hand. It may be designed such that the three major axes of rotation intersect at point located in the palm of the hand or any other suitable location. By having intersecting rotational axes, it is possible to exert a three-dimensional point load on the hand at the intersecting point. This is of particular concern if the articulated interface is not capable of transmitting torques to the hand. Typically, such an interface is used with a grounding device such as the one described in FIG. 2a which can exert three degrees-of-freedom of force. In another embodiment, it may be desirable to add torque producing means to each of the three-degree-of-freedom of the articulated interface 2030. This may be the case if a six-degree-of-freedom grounding device is used.

Figure 2C:
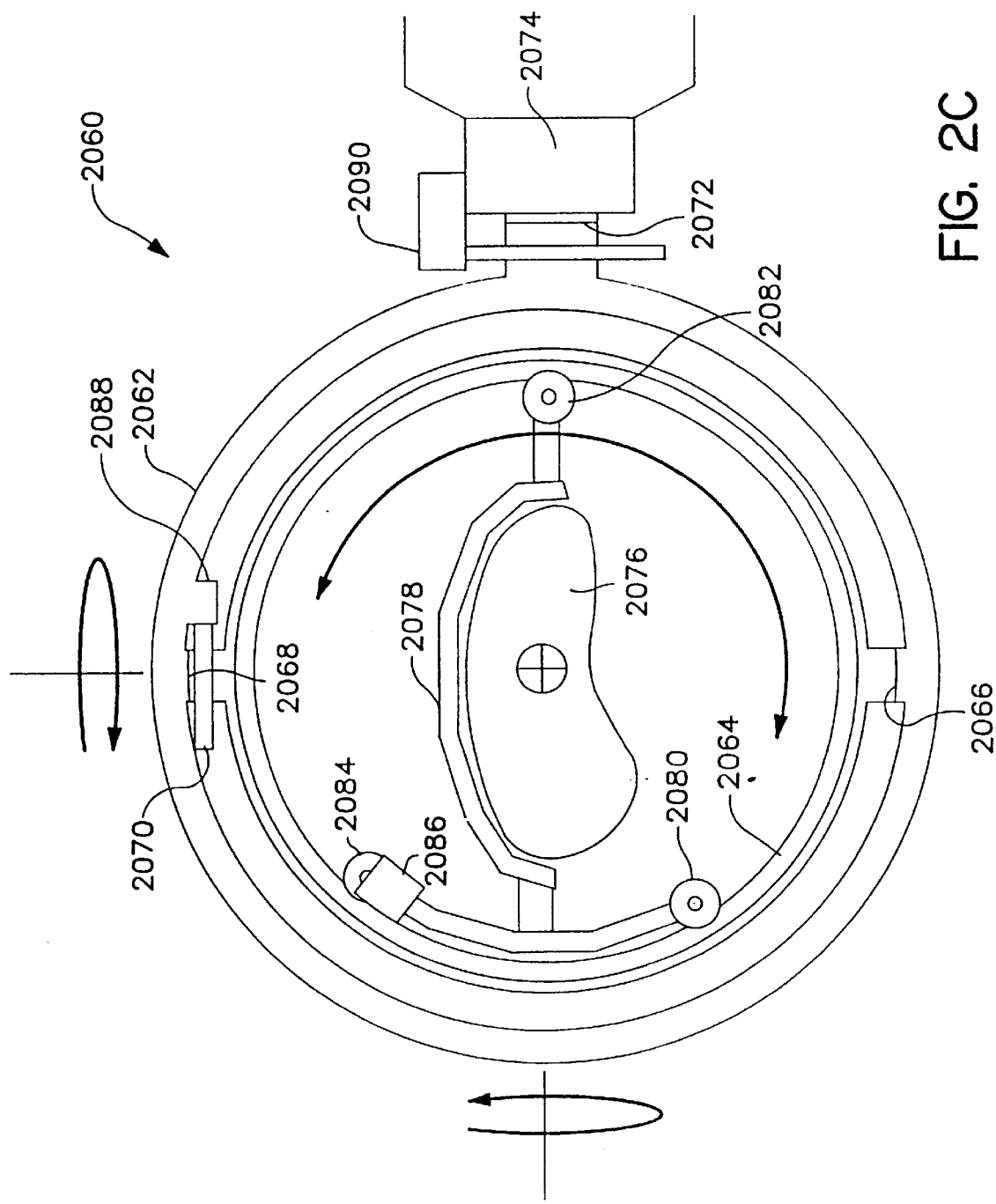
FIG. 2C is a diagrammatic illustration showing a side view of an embodiment of the articulated interface that connects the force-feedback device to a reference point off the body (ground).

FIG. 2c is a side view of the articulated three degree-of-freedom interface described in FIG. 2b which illustrates where angular position sensing means may be located on the device 2060. It shows the two concentric rings 2062 and 2064. The smaller of the two rings 2064 is attached to the larger ring 2062 via pivot joints 2066 at the bottom and 2068 at the top, such that the inner ring 2064 can rotate inside, and with respect to, the outer ring 2062. This comprises the first degree-of-freedom of rotation of the interface 2060. The outer ring 2062 is attached to the grounding device described in FIG. 2a via a pivot joint 2072. This comprises the second degree-of-freedom of rotation of the interface 2060. Inside the inner ring 2064 resides an attachment 2078 which serves to affix the interface 2060 to the force-feedback means which is the main subject of this invention. For clarity, the force-feedback means is omitted. The attachment 2078 is connected to the force-feedback. The attachment 2078 interfaces with the inner ring via a set of three or more wheel-like rotational mechanisms 2080, 2082 and 2084. These rotational mechanisms let the backplate 2078 rotate with respect to the inner ring 2064 and form the third degree-of-freedom of rotation of the interface 2060. It is desirable to add a sensing means to each of the degrees-of-freedom in order to determine the orientation of the hand in space. These sensing means may include, but are not limited to, encoders, potentiometers, Hall-Effect sensors and the like. The figure illustrates how such sensing means may be positioned on the interface 2060. An angular-position-sensing means 2070 can be affixed to the pivot joint 2068 in order to measure the angular position of the inner ring 2064 with respect to the outer ring. Similarly, an angular-position-sensing means 2090 can be affixed to the pivot joint 2072 in order to measure the angular position of the outer ring 2062 with respect to the grounding device 2074. Finally, an angular-position-sensing means 2086 can be affixed to one of the rotational mechanisms 2084 in order to measure the angular position of the attachment 2078 with respect to the inner ring 2064.

In operation, the articulated interface 2060 operates in a manner similar to the interface described in FIG. 2b.

For further understanding of the device, we now refer to the embodiment in FIG. 3 which shows a particular embodiment of the hand-force-feedback device 300 which is worn over an instrumented glove 301 capable of measuring the position of the hand. In this embodiment, a mechanical superstructure capable of exerting forces on the thumb is shown while the structures that would be used for the other fingers are omitted for clarity. The device 300 comprises a superstructure having a front cam 302 and a rear cam 304, a connecting link 306, a cam-supporting structure 308, and an attachment 310 from the cam-supporting structure 308 to a back plate 312. For exerting forces at the fingertip, a force applicator 316 to which is attached a tendon 318, is used. The force applicator 316 may employ any one of multiple ways of applying forces to the fingertips. For example, forces may be applied to the fingertips as shown and described in U.S. Pat. No. 5,631,861 (where they are referred to as "feedback assemblies"), the contents of which are incorporated in their entirety herein by reference as if explicitly included.

In one embodiment, it is desirable to include a force-sensing means in the force applicator, as described in the aforementioned U.S. Pat. No. 5,631,861. The force applicator may also be a thimble-like cup, or even a loop which fits around the fingertip. The tendon 318 is routed in a guiding groove at the top of the front cam 302 passing through both a rigid tendon guide 320 and, optionally, a flexible tendon guide 322. From the flexible tendon guide 322, the tendon 318 continues through a groove at the top of the rear cam 304 and into the tendon casing 324, which is affixed to the back of the cam-supporting structure 308. In order to track the adduction/abduction movement of the thumb base joint, the cam supporting structure 308 is free to rotate with respect to the attachment 310 by means of a revolute joint 326. Furthermore, the attachment 310 connects to the back plate 312 by means of a fastener 328, which enables the user to position the cam supporting structure 308 at the base of the thumb. The backplate 312 is attached to the hand by any convenient means, such as straps, belts, tape, or the like. In addition, the front cam 302 attaches to the middle phalanx of the thumb by an attachment device 330, which may be any convenient means, such as a strap or belt. Conveniently, the front cam may be mounted on a base 332 to which the attachment means 330 is attached.

In operation, the mechanical superstructure allows the tendon 318 to be routed to the force applicator 316, regardless of thumb configuration or position and without hindering movement of the thumb. As the thumb is flexed the entire superstructure will move to track the thumb's movement. When tension is exerted upon the tendon, a resistive force will be applied to the fingertip by the force applicator 316 and the superstructure will produce reactive forces on the back of the thumb by pressing down on the attached portions and thus producing reactive torques at the joints. The connecting link 306 maintains alignment between the front cam 302 and the rear cam 304 during movement of the thumb. As illustrated in the embodiment of FIG. 3, the connecting link is straight, but it can be designed to have a curved or angular profile that better conforms to the shape of the finger when it is flexed. The rigid tendon guides 314 and 320 and the flexible tendon guide 322 ensure that the tendon remains in the cam groove. The flexible tendon guide 322, for example, a flexible spring wire, can retract out of the way of the rear cam 304 as the thumb is hyper-extended. This will be further expanded upon when the invention is described relative to the embodiment in FIG. 5a and FIG. 5b.

In the embodiment depicted in FIG. 3, the instrumented glove 301 is used to obtain information on the position of the hand. Such information is required by the force-control unit in order to determine the force that should be exerted at the fingertip. Using a mechanical superstructure such as the one described in FIG. 3, it is also possible to forego using the instrumented glove altogether in favor of angular position sensing means incorporated directly into the superstructure. In this FIG. 3 embodiment, these position sensing means could be located at the three pivot points, namely the joints 334 and 336 at each end of the connecting link 306, and the pivot point 338 at the base of the rear cam 304. Examples of angular-position-sensing means include, but are not limited to, any devices which provides body-part position and/or orientation: mechanical, electrical, optical, strain gage, electromagnetic, ultrasonic, piezoelectric, Hall-effect, infrared emitter/detector pair, encoder/potentiometer, laser scanning or other position and/or orientation sensors.

FIG. 4a shows an embodiment of the hand-force-feedback-device 400 which is worn over an instrumented glove 401 capable of measuring the position of the hand. Alternatively, angular position sensing means can be located directly in the superstructure as described in FIG. 3. In this embodiment, a mechanical superstructure capable of exerting forces on the index finger is shown while the structures that would be used for the other fingers are omitted for clarity. The device 400 comprises a superstructure having a front cam 402 and a rear cam 404, a connecting link 406, a cam supporting structure 408, and an attachment 410 from the cam supporting structure 408 to a backplate 412. For exerting forces at the fingertip, a force applicator 416 (see also 316 in FIG. 3) to which is attached a tendon 418, is used. The tendon 418 is routed in a guiding groove at the top of the front cam 402 passing through both rigid tendon guides 414 and 420 and an optional flexible tendon guide 422. From the flexible tendon guide 422, the tendon 418 continues through a groove at the top of the rear cam 404 and into the tendon casing 424, which is affixed to the back of the cam supporting structure 408. In order to track the adduction/abduction movement of the index finger base joint, the cam supporting structure 408 is free to rotate with respect to the attachment 410 by means of a revolute joint 426. The backplate 412 is attached to the hand by any convenient means 428, such as straps, belts or the like. In addition, the front cam 402 attaches to the middle phalanx of the finger by an attachment device 430, which may be any convenient means, such as a strap or belt. Conveniently, the front cam is supported by a base 432 to which the attachment device 430 is attached. In operation, the mechanical superstructure functions in a manner similar to the one for the structure described in FIG. 3.

Figure 4B:
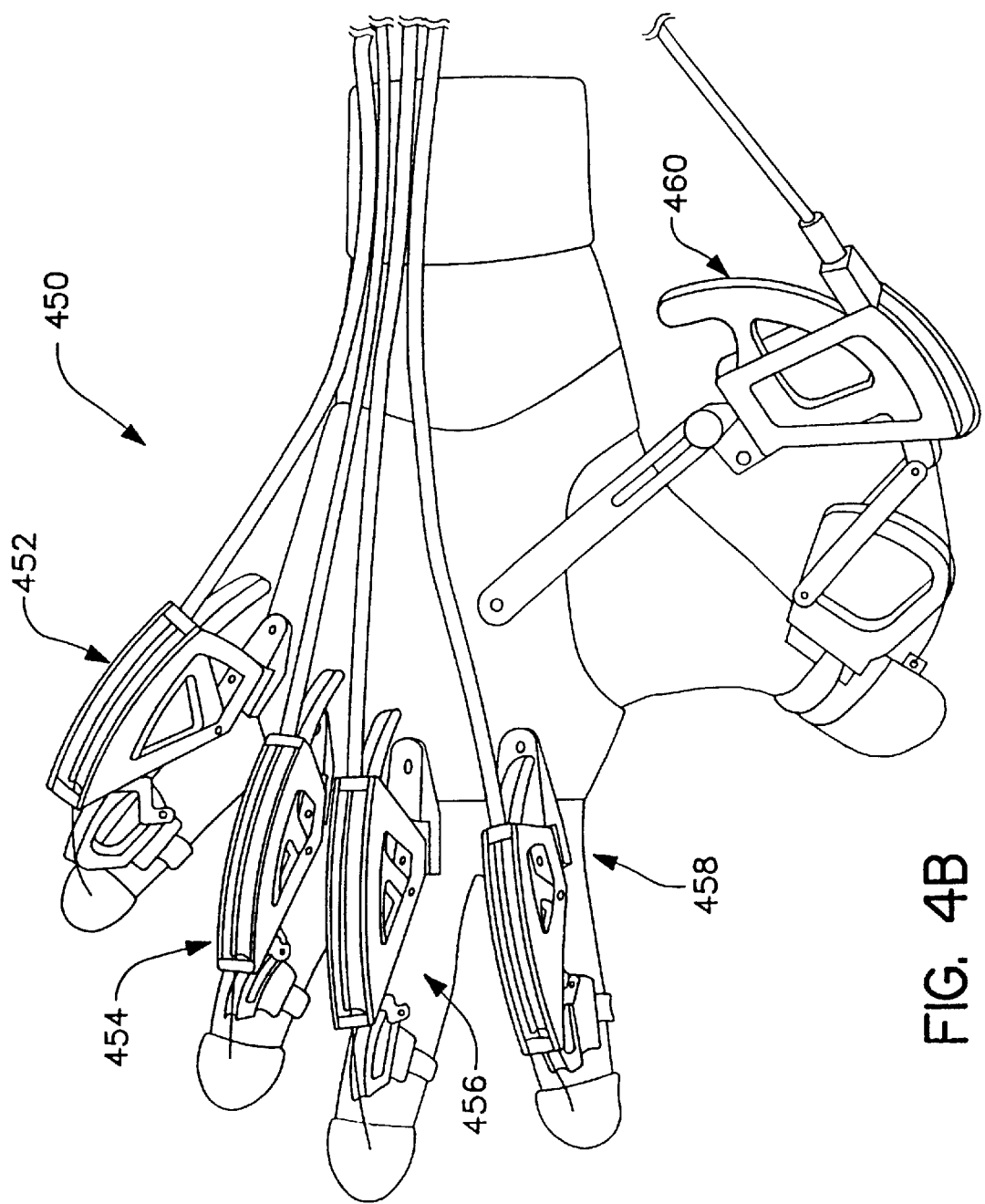
FIG. 4B is a diagrammatic illustration showing a perspective view from the top of a whole-hand-force-feedback-device.

FIG. 4b is a perspective view of the embodiment of the invention that is described in FIGS. 3 and 4a. Whereas the devices in FIGS. 3 and 4a show structures implemented on a single finger, the device 450 in this figure illustrates a mechanism with force-feedback structures (452, 454, 456, 458, 460) on each of the five fingers of the hand. A simplified version of device 450 can be implemented with, for example, structures on the thumb 460, the index 458 and the middle finger 456.

Figure 5A:
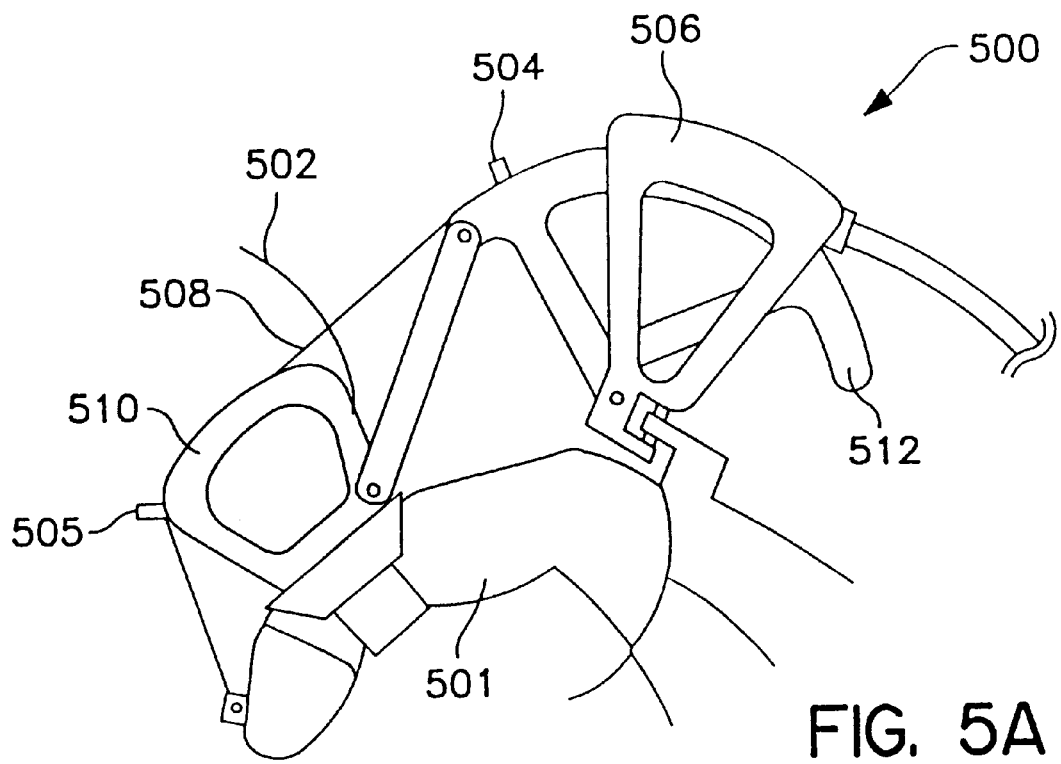
FIGS. 5A and 5B are diagrammatic illustrations showing respectively side views of the tendon-guiding mechanism in a flexed and extended position.
Figure 5B:
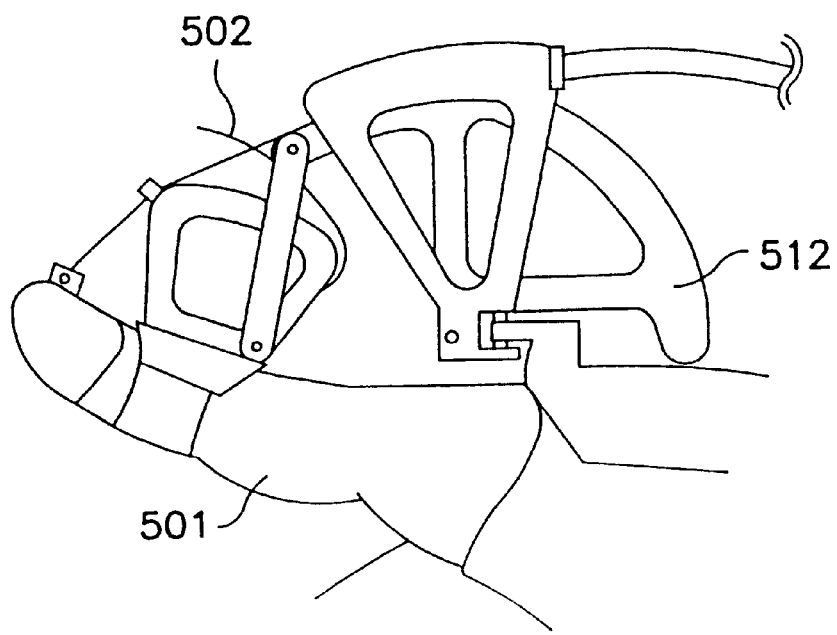
Figure 5C:
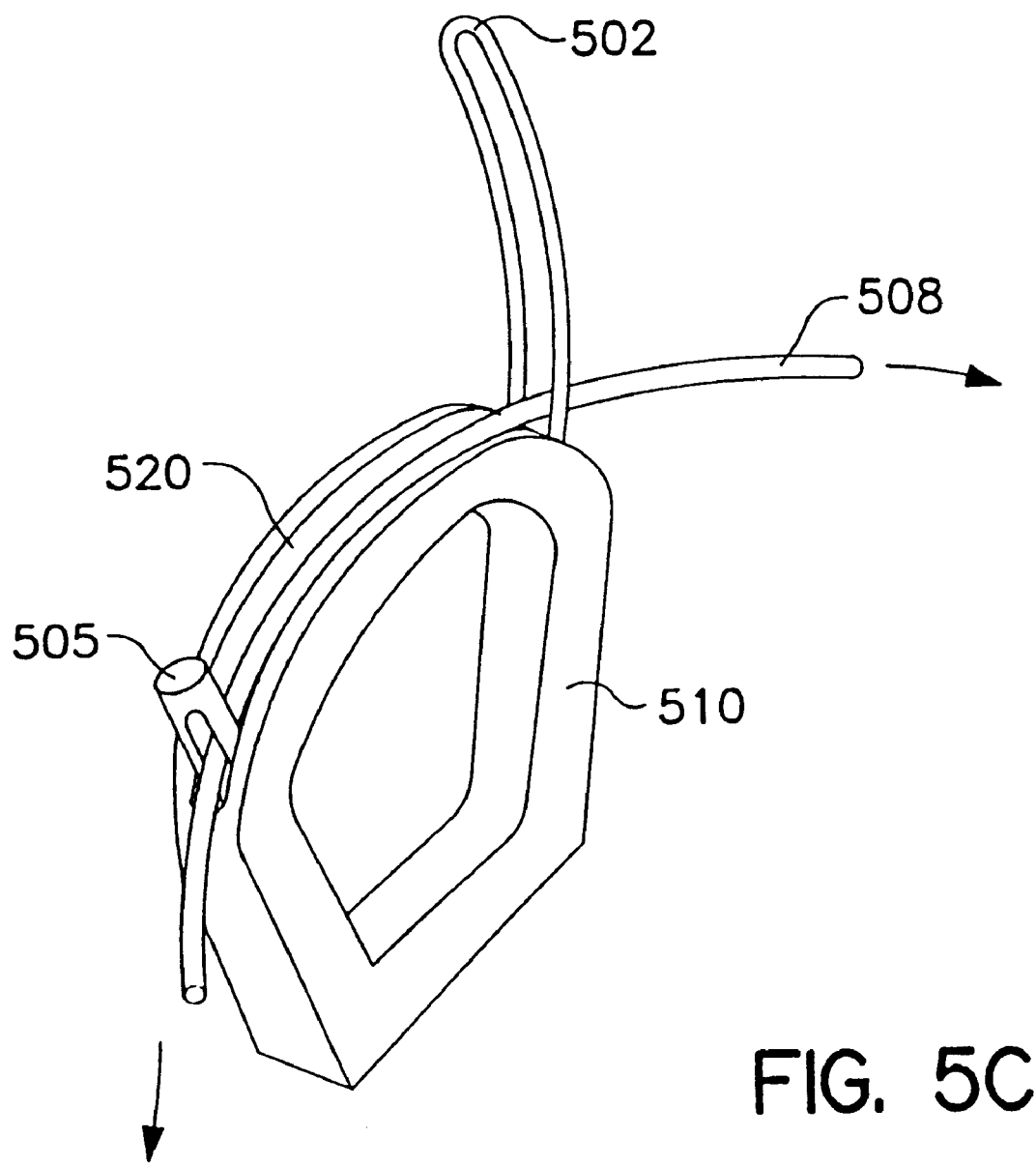
FIG. 5C shows a perspective view of a front cam which includes both rigid and flexible tendon guides.

We now direct our discussion to the structures illustrated in FIG. 5. FIGS. 5a, 5b and 5c serve to illustrate how the tendons are kept atop the cams in the embodiments described herein. More particularly, FIG. 5a shows a mechanical superstructure 500 for a single finger 501 for a flexed finger, and serves to illustrate the functionality of the flexible tendon guide 502 which, in conjunction with the rigid tendon guides 504 and 505 and the cam supporting structure 506, helps keep the tendon 508 in the grooves located on the front 510 and rear 512 cams. When the finger is flexed, the flexible tendon guide springs up into position and helps guide the tendon 508 into the grove atop the cam.

The structure illustrated in FIG. 5b shows the mechanical superstructure depicted in FIG. 5a in the case where the finger 501 is hyper-extended instead of flexed. In this case, the flexible tendon guide 502 bends out of the way once it makes contact with the rear cam 512. The structure illustrated in FIG. 5c shows a perspective view of a front cam 510 which includes both rigid 55 and flexible 502 tendon guides. The embodiment in FIG. 5c also shows how a groove 520 can be included atop a cam-like structure 510 to further help guide the tendon 508 to the fingertip. In operation, the tendon slides back and forth in the groove as the finger is flexed and extended.

Figure 6:
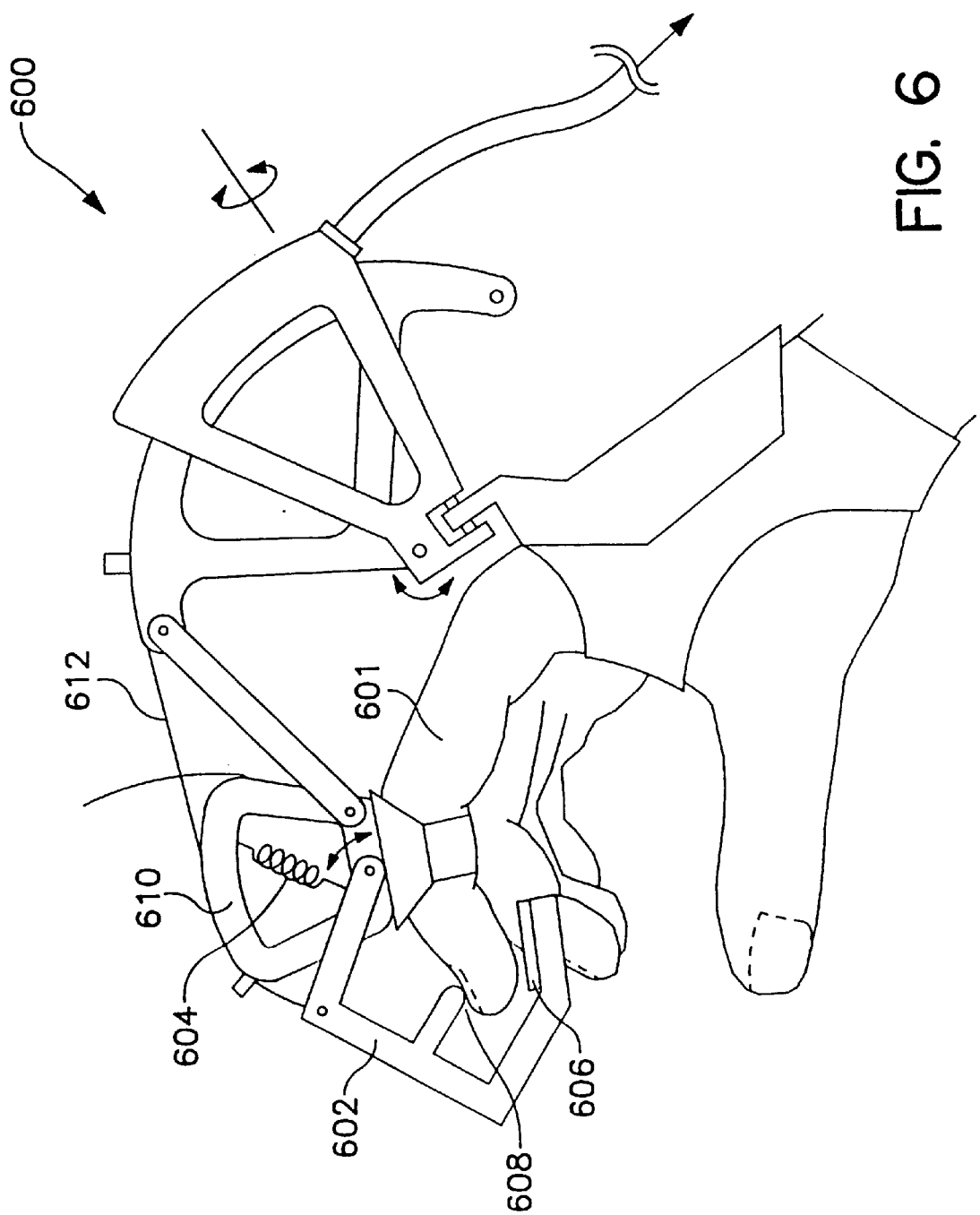
FIG. 6 is a diagrammatic illustration showing a side view of an alternative embodiment of the mechanical structure of an index-finger-controlling force-feedback device.

With respect to the illustration in FIG. 6, there is shown an embodiment of the invention in which a mechanical structure 600 operates in a manner similar to the one described relative to the embodiment in FIG. 4a but includes a different force applicator 602. Only the structure for the index finger 601 is represented in the illustration to preserve clarity, but the structure could be repeated for some or for all of the four other fingers. In this case, the force applicator 602 is designed such that it is not in contact with the fingertip until simulated contact forces are required. Force applicators are also described in U.S. Pat. No. 5,631,861 where they are referred to as "feedback assemblies." These designs have been adapted to make use of the front cam 604 as a means to attach to the finger 601.

The force-applicator structure 602 consists of a force pad 606 (which can be fitted with force-sensing means), a structure support 608 and a contact spring 610. In this implementation, when there is little or no tension in the tendon 612, the contact spring 610 pushes on the force-applicator structure 602 such that the structure support 608 touches the back of the fingertip (nail area). If the finger is flexed, the force applicator structure 602 moves accordingly, thus keeping the force pad 606 a small distance away from the fingertip. When is it desired to exert a force on the fingertip, the tension in the tendon 612 overcomes the force of the contact spring and the force pad 606 makes contact with the fingertip. By keeping the force pad 606 away from the fingertip until force is applied, bandwidth requirements of the force applying means are reduced.

For example, when the invention is used to provide feedback from a virtual environment and a virtual object is grasped, the force pad makes contact with the fingertip with a non-zero relative velocity, as would a real object when contacting the fingertip. If the force pad were always in contact with the fingertip, much larger tendon velocities and accelerations would have to be generated to provide the same contact sensation to the user. In operation, the rest of the mechanical superstructure functions in a manner similar to the behavior of the structure described in FIG. 3 and is not described further.

Another embodiment of the invention is illustrated in FIG. 7a, which utilizes a simplified cam-based superstructure 700 requiring fewer moving parts which is worn over an instrumented glove 702 capable of measuring hand position. In this embodiment, a mechanical superstructure capable of exerting forces on the index finger is shown while the structures that would be used for the other fingers are omitted for clarity. The device 700 comprises a superstructure having a front can 706 with front 710 and rear 712 tendon guides, a rear cam 708 with front 714 and rear 716 tendon guides and a base support 718 which anchors the tendon casing 720. For exerting forces at the fingertip, a force applicator 722 to which is attached a tendon 724, is used. The tendon 724 is routed in a guiding groove at the top of the front cam 706 passing through tendon guides 710 and 712 and a guiding groove at the top of the rear cam 708 passing through tendon guides 714 and 716. From the rear cam 708, the tendon 724 goes into the tendon casing 720, which is affixed to the back of the base support 718, which in turn is attached to a backplate 726 for added stability. The backplate 726 is attached to the hand by any convenient means 728, such as straps, belts, or the like. In addition, the front cam 706 attaches to the middle phalanx of the finger by an attachment device 732, which may be any convenient means, such as a strap or belt. Conveniently, the front cam may be mounted on a base 730 to which the attachment means 732 is affixed. Similarly, the rear cam 708 attaches to the proximal phalanx of the finger by an attachment device 736, which may be any convenient means, such as a strap or belt. Again, the rear cam 708 may be mounted on a base 734 to which the attachment means 736 is fixed.

An end view of an embodiment of one of the tendon guides is illustrated in FIG. 7b. It illustrates how the guide 750 keeps the tendon 752 aligned with the grove of the cam 754 while still letting it break contact with the cam when the finger is hyper-extended.

In operation, the instrumented glove 702 acts as the position-sensing means for the device. Under little or no tendon force, the finger is free to move and flex in any direction while the position sensing in the hand ensures that the tendon slack will be kept to a minimum, ensuring prompt response when forces are desired at the fingertip. Forces and torques are transmitted to the fingertip and joints respectively in a manner similar to the one described in FIG. 4a.

FIGS. 8a–8e are side views of four different exemplary embodiments of front cams for the embodiments of the devices depicted in FIGS. 3–7. As mentioned in the description of the invention relative to the embodiment in FIG. 3, it is possible to include a force-sensing means in the force applicator located at the fingertip. An alternate way of measuring the forces applied at the fingertip is to measure the tension in the tendon as it leaves the front cam.

Figure 8B:
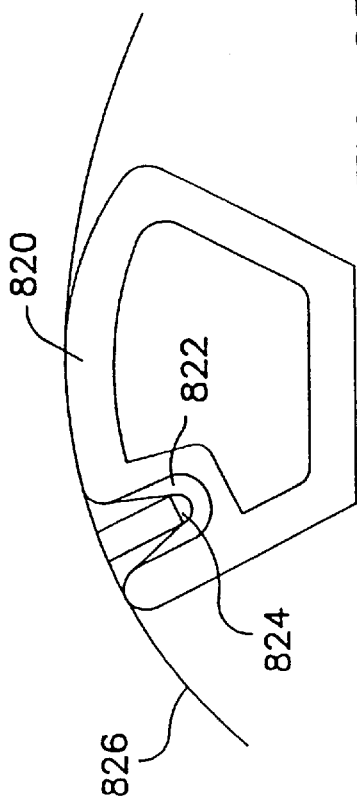
FIGS. 8A–8E are diagrammatic illustration showing several exemplary embodiments of tendon-tension sensors
Figure 8D:
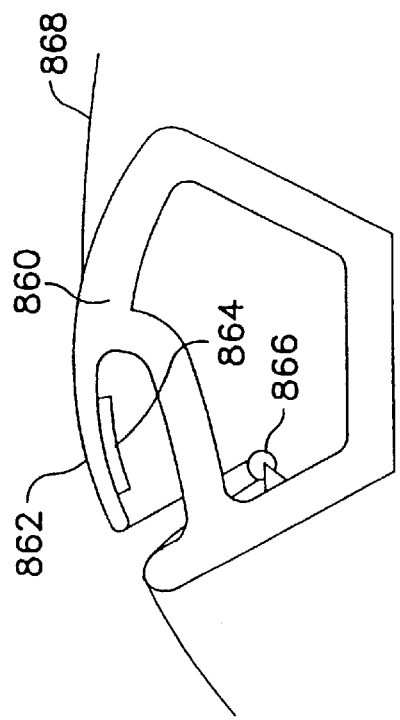
Figure 8A:
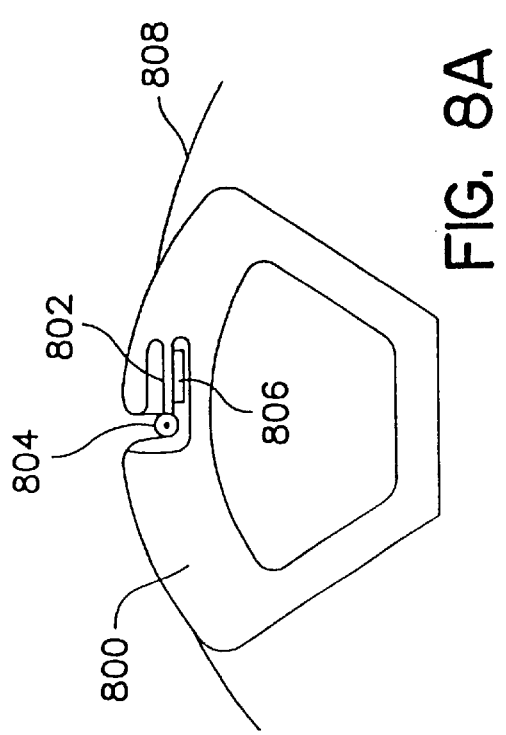

FIG. 8a is an illustration showing an exemplary cam-based force sensor incorporated into the front cam 800. In this embodiment, a small flexure 802 is machined into the cam pattern and a small pulley-like device 804 is attached to the end of the flexure 802. The tendon 808 slides in a groove machined into the cam, goes around the pulley 804 and then back up onto the groove. An increase in tension in the tendon 808 causes the flexure 802 to bend and a deflection sensing means 806 (such as a strain gauge) attached to the flexure measures the deflection. By measuring the deflection of the flexure and knowing its stiffness, it is possible to determine the tension in the tendon and thus the force exerted at the fingertip.

FIG. 8b is an illustration showing an exemplary cam-based force sensor incorporated into the front cam 820, where a detour 822 is included in the tendon path on the front cam such that the tendon 826 must go around a specific point where a force-measuring device 824, such as a load cell, can be located. The force measured by the force-measuring device 824 will be proportional to the tension in the tendon 826 and thus to the force exerted at the fingertip.

Figure 8C:
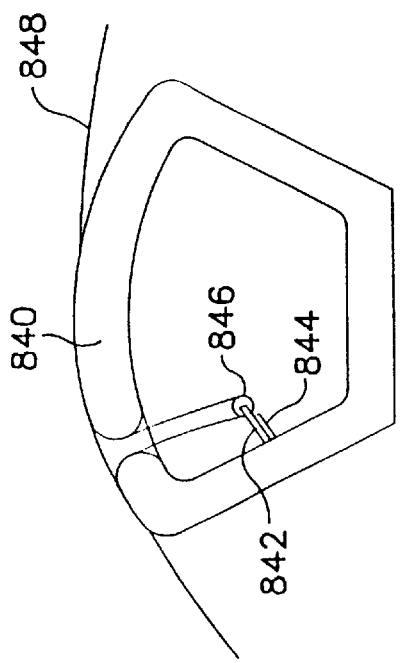

FIG. 8c is an illustration showing an exemplary cam-based force sensor incorporated into the front cam 840, where the tendon 848 is redirected from it's intended path in a groove atop the front cam 840 such that it passes around a pulley-like device 846 mounted on a flexure 842 which is attached to the inside of the front cam, before returning back to its intended path in the groove atop the front cam 840. Using this approach, the tension in the tendon 848 will produce a force on the pulley which will be nominally perpendicular to the flexure 842, and thus produce a deflection which is proportional to the force. A deflection sensing means 844 (such as a strain gauge) attached to the flexure 842 measures said deflection. By measuring the deflection of the flexure and knowing its stiffness, it is possible to determine the tension in the tendon 868 and thus the force exerted at the fingertip.

FIG. 8d is an illustration showing an exemplary cam-based force sensor incorporated into the front cam 860, where the tendon 868 is redirected from it's intended path in a groove atop the front cam 860 such that it passes around a pulley-like device 866 located inside the front cam 860. Also, a flexure 862 is incorporated into the top part of the front cam such that the tendon 868 slides over the flexure. The effect of rerouting the tendon 868 around the firmly-anchored pulley-like device 866 produces a deflection in the flexure 862 when the tendon is under tension. A deflection-sensing means 864 (such as a strain gauge) attached to the flexure 862 measures the deflection. By measuring the deflection of the flexure and knowing its stiffness, it is possible to determine the tension in the tendon 868 and thus the force exerted at the fingertip.

Figure 8E:
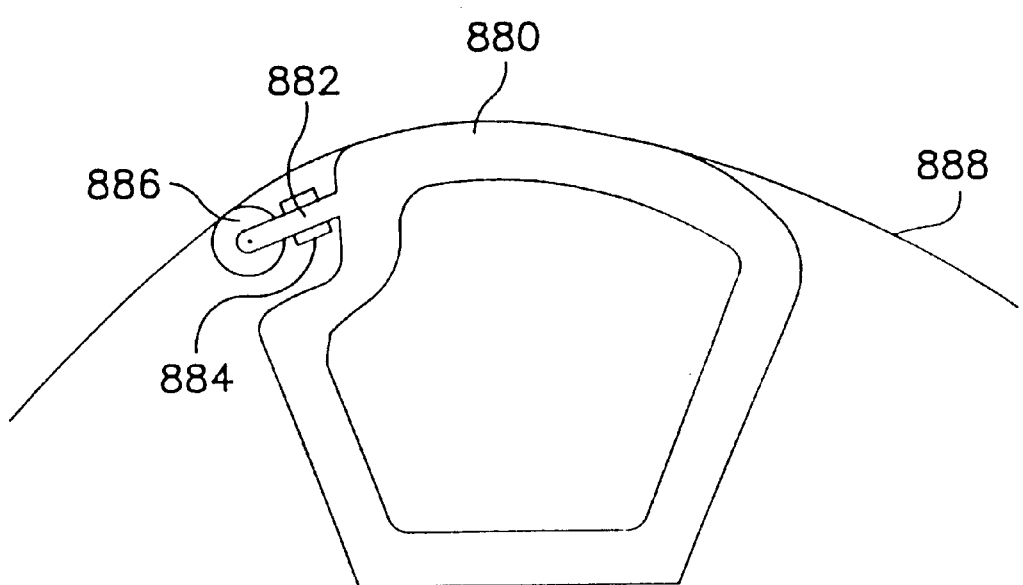

FIG. 8e is an illustration showing an exemplary cam-based force sensor incorporated into the front cam 880, where the tendon 888 passes over a pulley-like device 886 before leaving the front cam 860. A flexure 882 is incorporated into the top part of the front cam such that the tendon 868 deflects the flexure when in tension. A deflection-sensing means 884 (such as a strain gauge) attached to the flexure 882 measures the deflection. By measuring the deflection of the flexure and knowing its stiffness, it is possible to determine the tension in the tendon 888 and thus the force exerted at the fingertip.

Figure 9:
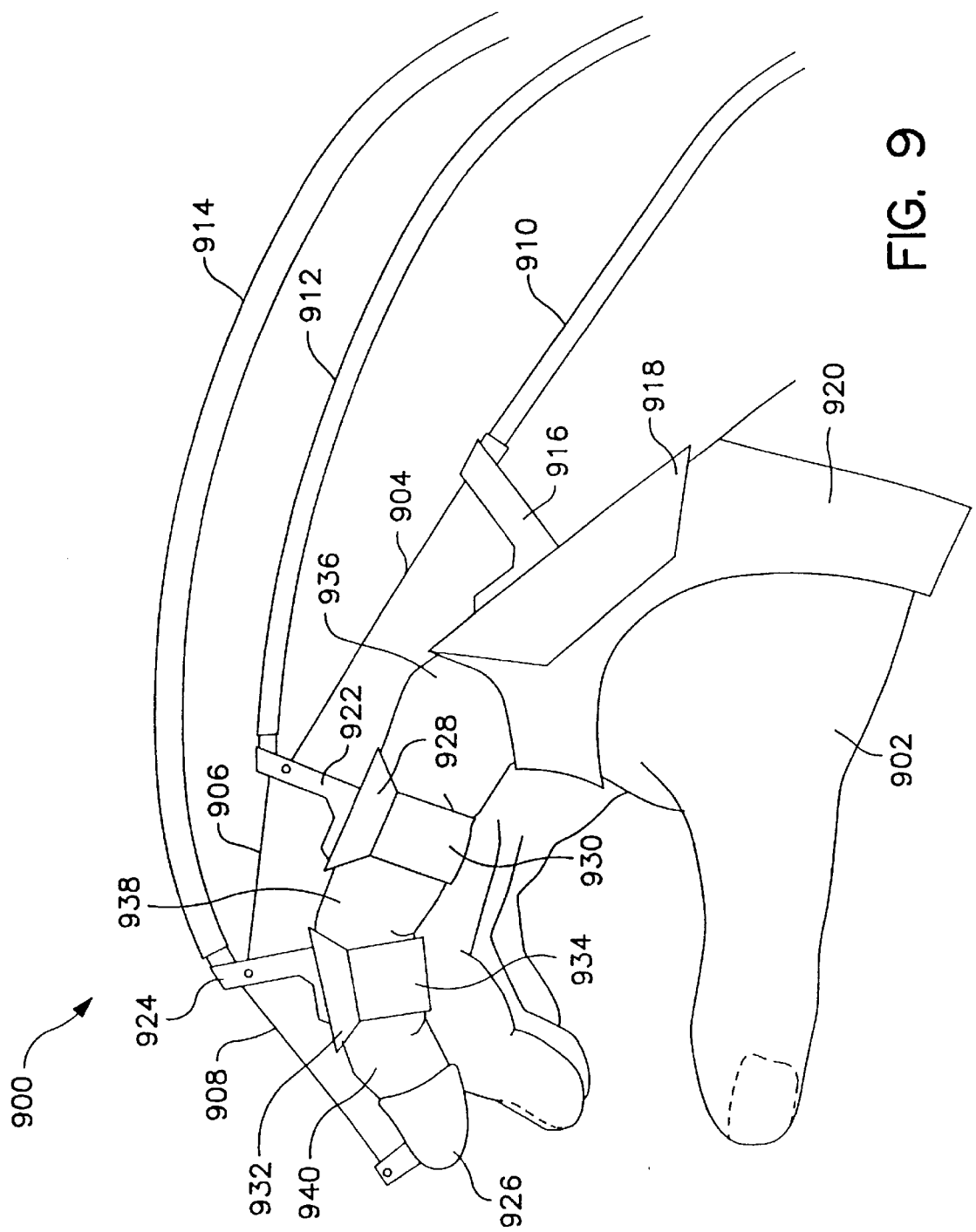
FIG. 9 is a diagrammatic illustration showing a side view of an alternative embodiment of the mechanical structure of an index-finger-controlling force-feedback device having a plurality of tendons for individual joint torque control.

Yet another embodiment of a hand force-feedback device 900 which is worn over an instrumented glove 902 capable of measuring the position of the hand is now described relative to the illustration in FIG. 9. In this particular embodiment, a mechanical superstructure using a plurality of tendons and capable of exerting a force at the fingertip and torques at each of the three joints of the index finger is shown. The individual structures that would be used for the other fingers are omitted for clarity. In this embodiment, three force-generating means, such as the one already described relative to the embodiment illustrated in FIG. 1, are required per finger. Forces are transmitted from the force transmitting means to the superstructure on the finger via tendons 904, 906 and 908 which are routed through tendon casings 910, 912 and 914, respectively. A base tower 916 anchors tendon casing 910 which houses tendon 904 which in turn terminates at tower 922. Similarly, tower 922 anchors tendon casing 912 which houses tendon 906 which in turn terminates at tower 924. Finally, tower 924 anchors tendon casing 914 which houses tendon 908 which in turn terminates at the force applicator 926 located at the fingertip. The base tower is mounted on a rigid base such as a backplate 918 which in turn is attached to the hand by any convenient means, such as straps, belts or the like 920. In addition, tower 922 attaches to the proximal phalanx of the index finger by an attachment device 930, which may be any convenient means, such as a strap or a belt. Conveniently, tower 922 may be mounted on a base 928 to which the attachment device 930 is attached. Similarly, tower 924 attaches to the middle phalanx of the index finger by an attachment device 934 and may also be mounted on a base 932 to which the attachment device 934 is attached.

In operation, the mechanical superstructure, used in conjunction with an instrumented glove 902, makes it possible to exert individually controlled resistive torques at each of the finger joints and a resistive force at the fingertip. By applying a tension in tendon 904, it is possible to pull on tower 922 which acts as a moment arm and produces a torque at the base joint 936 of the finger. Similarly, by applying a tension in tendon 906, it is possible to pull on tower 924 which acts as a moment arm and produces a torque at the middle joint 938 of the finger. Finally, by applying a tension in tendon 908, it is possible to pull on the force applicator 926 which produces a torque at the distal joint 940 of the finger while also producing a resistive force at the fingertip 926.

Figure 10A:
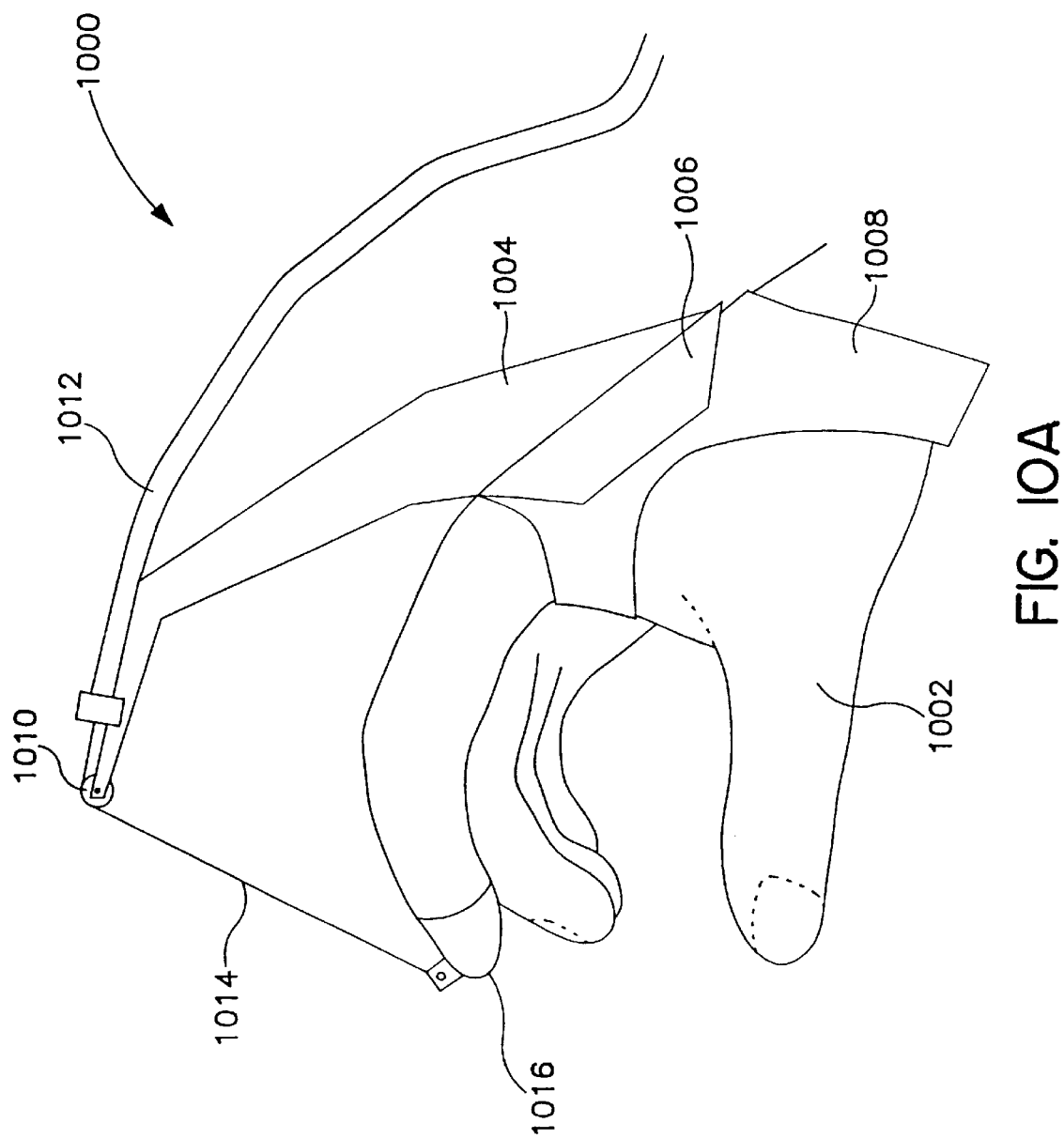
FIG. 10A is a diagrammatic illustration showing a side view of an alternative embodiment of the mechanical structure of an index-finger-controlling force-feedback device using a single tower structure.

In FIG. 10a there is illustrated another embodiment of the hand force-feedback device. In this embodiment, a mechanical superstructure 1000 capable of exerting a force at the tip of the index finger is shown. The individual structures that would be used for the other fingers are omitted for clarity. The superstructure is designed to be worn over an instrumented glove 1002 capable of measuring the position of the hand. Forces are transmitted from the force-transmitting means to the superstructure on the finger via a tendon 1014 which is routed through a tendon casings 1012. A tendon-supporting tower 1004 extends above the finger and serves as the end point for the tendon casing 1012. The tendon 1014 exits the tendon casing and then ends at a force applicator 1016 which enables it to exert forces on the fingertip. To minimizes friction, a pulley-type device 1010 or the like may be used to route the tendon over the end of the tower. The tower 1004 is mounted on a rigid base such as a backplate 1006 which in turn is attached to the hand by any convenient means, such as straps, belts or the like 1008.

In operation, the tower structure keeps the tendon 1014 above the finger such that it can exert a resistive force on the force applicator 1016 for any given finger configuration. In this and the other embodiments described heretofore, the towers also. cooperate with the cams to augment or enhance the moment arm and provide moment augmenting means. It the illustrated configuration, the mechanical superstructure 1000 resides above the finger in a plane which coincides with the plane of motion of the finger when it is flexing. Additional superstructures may be added which reside in different planes in order to exert forces in another plane, such as the plane where finger adduction/abduction occurs. By combining two or more of the described superstructures for one finger, it is possible to produce resulting three-dimensional forces.

Figure 10B:
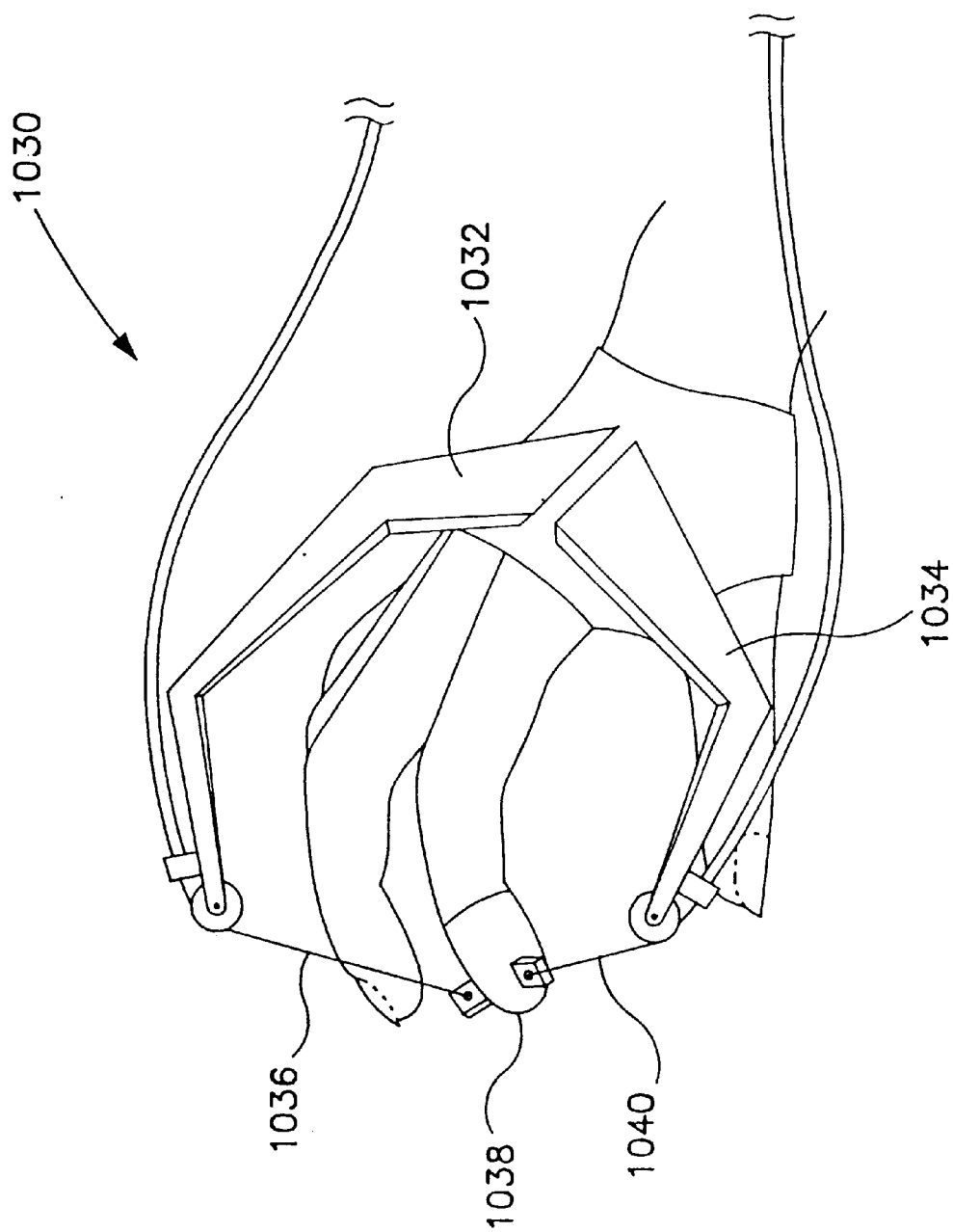
FIG. 10B shows a side view of the mechanical structure of an index-finger-controlling force-feedback device using two tower structures.

FIG. 10b shows another embodiment of the hand force-feedback device described in FIG. 10a where an additional. In this embodiment, a mechanical superstructure 1030 capable of exerting a force at the tip of the index finger is shown. The superstructure consists of two individual tower structures 1032 and 1034 and serves to illustrate how multiple structure can be used in conjunction with one another to provide more complex force feedback to the user.

In operation, tower structure 1032 keeps the tendon 1036 above the finger such that it can exert a resistive force on the force applicator 1038 for any given finger configuration. In the illustrated configuration, tower structure 1032 resides above the finger in a plane which coincides with the plane of motion of the finger when it is flexing. An additional tower structure .1034 is shown and it resides in a plane which is perpendicular to the plane in which the other tower structure 1032 resides. The tower structure 1034 routes the tendon 1040 to the force applicator 1038 where it may exert side forces on the finger. By exerting forces with both force-feedback structures simultaneously, it is possible to produce complex forces which act outside the planes of both structures.

FIG. 10c is a perspective view of the embodiment of the invention that is described in FIGS. 10a and 10b. Whereas the devices in FIGS. 10a and 10b show structures implemented on a single finger, the device 1050 in this figure illustrates a mechanism with force-feedback structures (1052, 1054, 1056, 1058, 1060) on each of the five fingers of the hand. A simplified version of the device 1050 can be implemented with, for example, structures on the thumb 1060, the index 1058 and the middle finger 1056.

In FIG. 11a, yet another embodiment of the hand-force-feedback device is illustrated. In this embodiment, a mechanical superstructure 1100 is affixed to the back of the hand and serves two roles: housing finger-joint-angle-sensing means 1121, and routing the force-applying tendons 1110 to the fingertips. Alternatively, the joint-angle-sensing-means can be omitted from the superstructure in favor of an instrumented glove 1120 capable of measuring hand position. In this illustration, the superstructure is shown for the index finger while the similar individual structures which may be used for the other fingers are omitted for clarity. The superstructure comprises a plurality of support towers 1114 through which passes a sliding tendon casing 1112 and which are linked together via a common flexible base 1113. The flexible base can be made of a spring steel, rubber, plastic, composite material, or any other appropriate material and can be designed in such a way that there are guiding pockets for bend sensors 1121 (e.g. the strain-gage bend sensor of Kramer et al.) located above each of the finger joints. In addition, the flexible base attaches to the finger using attachment devices 1118, which may be any convenient means, such as a strap or a belt. The support towers 1114 can be either attached to the flexible base 1113 if spring steel is used, or molded into it if rubber or plastic is used. The sliding tendon casing is anchored at the support tower 1115 closest to the fingertip but free to slide through holes in the other support towers 1114. The tendon which transmits forces to the force applicator at the fingertip 1116 is routed from the force-applying means described relative to the embodiment illustrated in FIG. 1 to the superstructure 1100 via a tendon casing 1102 which is anchored at a base support 1104. The base support may be mounted on a rigid backplate 1106 which in turn is attached to the hand by any convenient means 1108 such as straps, belts or the like.

FIG. 11*b* shows an end view of one of the support towers 1122 already shown and described relative to the embodiment in FIG. 11*a*, and shows the chamfered hole 1124 through which the sliding tendon casing moves. In this embodiment, all the support towers have the same height but it might also be desirable to vary the heights to change the distribution of the forces on the finger.

In operation, the sliding tendon casing 1112 is free to move relative to the holes in the support towers 1114 and it's purpose is to provide a smooth arced path for the tendon 1110 from the base support 1104 to the force applicator 1116 located at the fingertip. The joint-sensing means 1121 located in the flexible base 1113, or the instrumented glove 1120 if it is used instead, serve to measure the flexion in the finger at each of its joints. The mechanical superstructure allows the tendon 1110 to be routed to the force applicator 1116, regardless of finger configuration or position and without hindering movement of the finger. As the finger is flexed the entire superstructure will move to track the finger's movement. When tension is exerted upon the tendon, a resistive force will be applied to the fingertip by the force applicator 1116 and the superstructure will produce reactive forces on the back of the finger by pressing down on it and thus producing reactive torques at the joints.

In FIG. 12*a*, we turn our attention to an embodiment of the invention that operates in a manner similar to the one illustrated in FIG. 11*a*. However, the embodiment illustrated in FIG. 12*a* differs in two primary respects from the embodiment in FIG. 11*a*. First, in FIG. 12*a*, tendon 1202 is routed through the support towers 1204 without the use of a sliding tendon casing such as the one depicted in FIG. 11*a*. The second difference is that the support towers 1204 are of varying height, unlike the support towers depicted in FIG. 11*a* which all have substantially the same height.

In FIG. 12*b*, there is illustrated an end view of one of the support towers 1207 illustrated FIG. 12*a*, and further shows the chamfered hole 1208 through which the sliding tendon moves. In operation, the device 1200 will function much like device 1100 in FIG. 11*a*, except that the resulting torques exerted at the finger joints are distributed somewhat differently, with larger torques exerted at the joints nearest to the base support 1206.

Figure 12C:
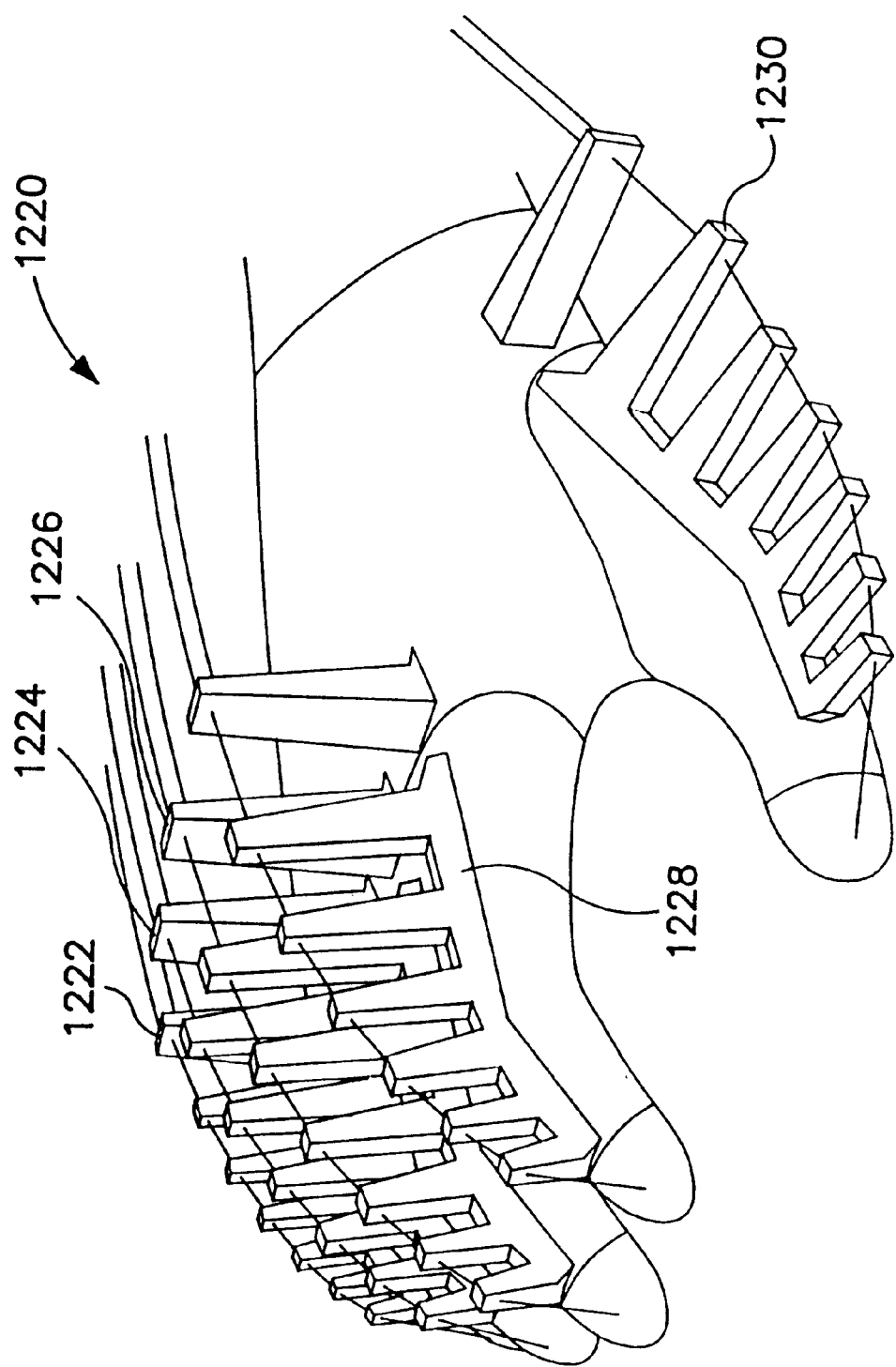
FIG. 12C is a perspective view of the mechanical structure of a whole-hand-controlling force-feedback device showing towers of varying heights for all five fingers.

FIG. 12*c* is a perspective view of the embodiment of the invention that is described in FIGS. 12*a* and 12*b*. Whereas the device in FIGS. 12*a* and 12*b* shows a structure implemented on a single finger, the device 1220 in this figure illustrates a mechanism with force-feedback structures (1222, 1224, 1226, 1228, 1230) on each of the five fingers of the hand. A simplified version of the device 1220 can be implemented with, for example, structures on the thumb 1230, the index 1228 and the middle finger 1226.

A variation of the embodiment of the structure in FIG. 7 is illustrated in FIG. 13*a*. The grooves in the front and rear cams used in the FIG. 7 embodiment, and detailed in FIG. 5*c*, can essentially be thought of as an infinite number of rollers placed side by side atop the cam to help guide the tendon to the fingertip with minimal friction. A superstructure 1300 is shown where a discrete number of rollers 1302 are used to guide the tendon 1318 instead of a continuous groove. In this instance, three rollers are used, but more or fewer rollers may be employed to provide the desired functionality, and any given quantity deemed adequate may be used. The device may be worn over an. instrumented glove 1304 capable of measuring hand position. In this embodiment, a mechanical superstructure capable of exerting forces on the index finger is shown while similar structures which may be used for the other fingers are omitted for clarity. The device 1300 comprises a superstructure having a front tower 1306 with front 1308 and rear 1310 tendon guides and three rollers 1302; a rear tower 1312 with front 1314 and rear 1316 tendon guides, and three rollers 1302; and a base support 1322 which anchors the tendon casing 1324. A connecting means 1320 such as the two links shown in the figure may be used to help ensure that the towers 1306 and 1312 remain aligned with one another. Similarly, such a connecting means may be used to connect the rear tower 13 12 to the base support 1322. When such an implementation is used, joint-sensing means (for example, encoders, potentiometers, electromagnetic sensors, and the like) may be positioned at the link joints thus removing the need for an instrumented glove 1304 to measure hand position. For exerting forces at the fingertip, a force applicator 1319 to which is attached a tendon 1318, is used. The tendon 1318 is routed along the pulleys 1302 at the top of front tower 1306 and passing through tendon guides 1308 and 1310 and the pulleys at the top of rear tower 1312 passing through tendon guides 1314 and 1316. From the rear tower, the tendon goes into the tendon casing 1324, which is affixed to the back of the base support 1322, which in turn may be attached to a backplate 1326 for added stability. The backplate 1326 is attached to the hand by any convenient means 1328, such as straps, belts or the like. In addition, the front and rear towers attach to the phalanges of the finger by attachment devices 1328, which may be any convenient means, such as a strap or belt. Conveniently, the front and rear towers may be mounted on bases 1330 to which the attachment means 1328 are fixed.

An end view of one of the tendon guides depicted in FIG. 13*a* is illustrated in FIG. 13*b*. It illustrates how the guide 1332 keeps the tendon 1334 aligned with the groove of the pulley 1336 while still letting it break contact with the pulley when the finger is hyper-extended.

In operation, the instrumented glove 1304 of FIG. 13, acts as the position-sensing means for the device. Under little or no tendon force, the finger is free to move and flex in any direction while the position sensing in the hand ensures-that the tendon slack will be kept to a minimum, ensuring prompt response when forces are desired at the fingertip. Forces and torques are transmitted to the fingertip and joints respectively in a manner similar to the one described in FIG. 4*a* and are not described further here.

Figure 14A:
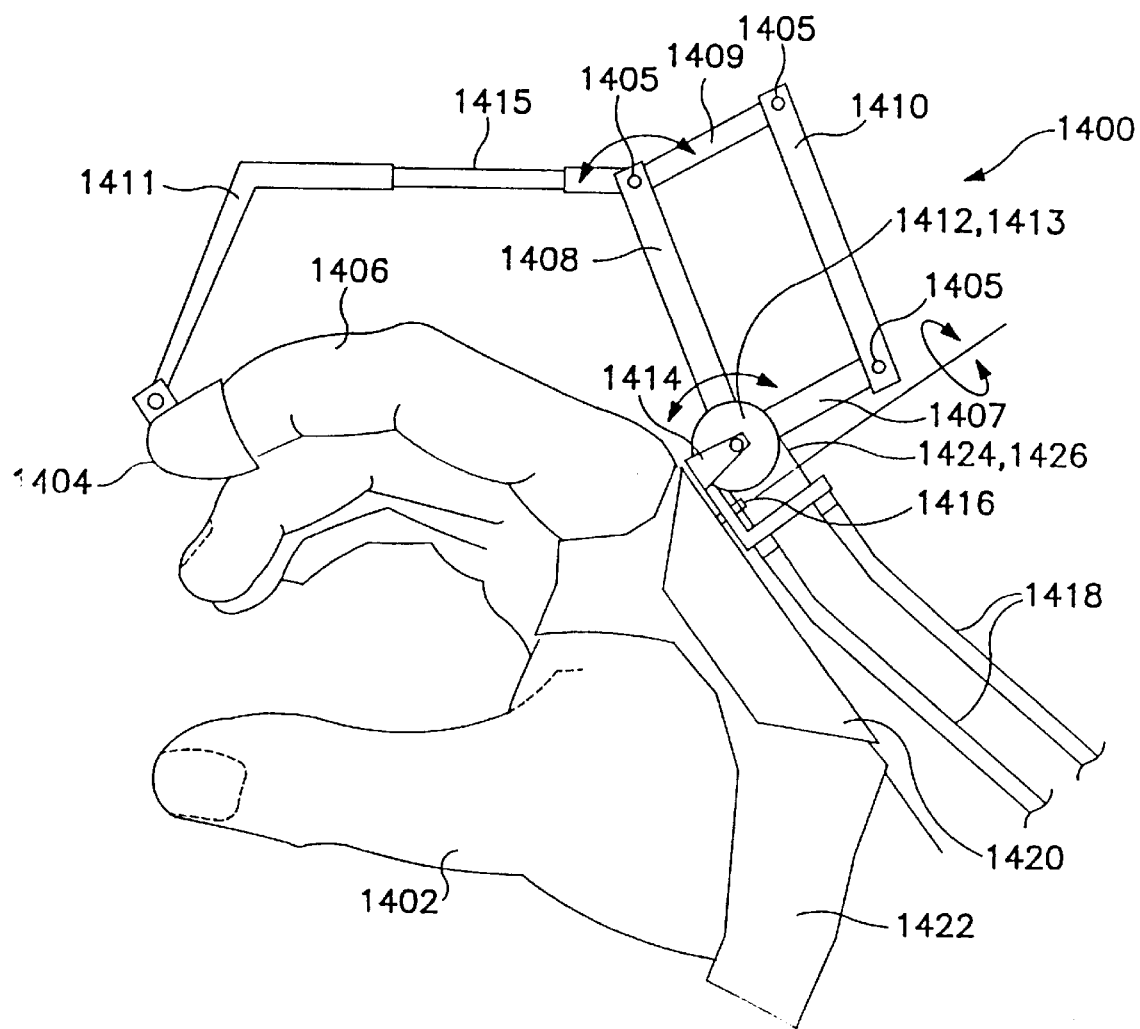
FIG. 14A is a diagrammatic illustration showing a side view of another alternative embodiment of the mechanical structure of an index-finger-controlling force-feedback device capable of exerting forces in the finger plane.

FIG. 14a is an illustration showing an embodiment of the invention which uses a superstructure 1400 which exerts a force directly at the fingertip without attaching to other parts of the finger. In this embodiment, a mechanical superstructure capable of exerting forces on the index finger 1406 is shown while similar structures which may be used for the other fingers are omitted for clarity. At the heart of the superstructure is a five-bar linkage consisting of links 1407, 1408, 1409 and 1410 which are attached together via revolute joints 1405. Link 1409 extends to a linear adjustment 1415 which attaches to another link 1411 which is attached to the force applicator 1404 at the fingertip. Links 1407 and 1408 are attached to pulleys 1412 and 1413, respectively. Pulley 1413 cannot be seen in the illustration as it is located directly behind pulley 1412 but it is shown in the perspective view of FIG. 15a. Links 1407 and 1408 and pulleys 1412 and 1413 are attached to, and pivot about, a support 1414. The support is also free to rotate about joint 1416 to track finger abduction/adduction. The support is connected to the backplate 1420 via the joint 1416 and the backplate is attached to the hand by any convenient means 1422 such as straps, belts or the like. Two tendons 1424 and 1426, one of which is not visible, are routed around, and fixed to, the two pulleys 1412 and 1413, respectively. The tendons are guided to the superstructure 1400 from the force-producing means as described relative to FIG. 1 using four tendon casings 1418, of which two can be seen in the illustration. Alternatively, incompressible yet flexible tendons such as steel wire may be used, wherein only two tendon casings 1418 are required because the tendons 1424, 1426 are thus able to both push and pull on the pulleys.

In operation, the mechanism is capable of fully tracking the motion of the finger when no forces are being exerted. To exerted forces, the torques on the pulleys 1424, 1426 are exerted via the tendons 1424, 1426, and these torques are translated to forces exerted at the fingertips via the five-bar linkage. Using this mechanism, it is possible to exert a force in any direction in the plane of the finger. Additionally, it may be desirable to add another pulley/tendon assembly to joint 1416 in order to exert resistive forces when the finger is abducting/adducting. By including a position-sensing means (e.g., encoder, potentiometer, Hall-effect sensor) at the force-applying means (e.g., DC motor, stepper motor, pneumatic actuator) it is possible to compute the position of the force applicator 1404 and therefore the fingertip, thus removing the need for an instrumented glove 1402 when it is not otherwise desired. The linear adjustment 1415 may be friction-based or indexed and serves to adjust the mechanism for a variety of hand sizes.

Figure 14B:
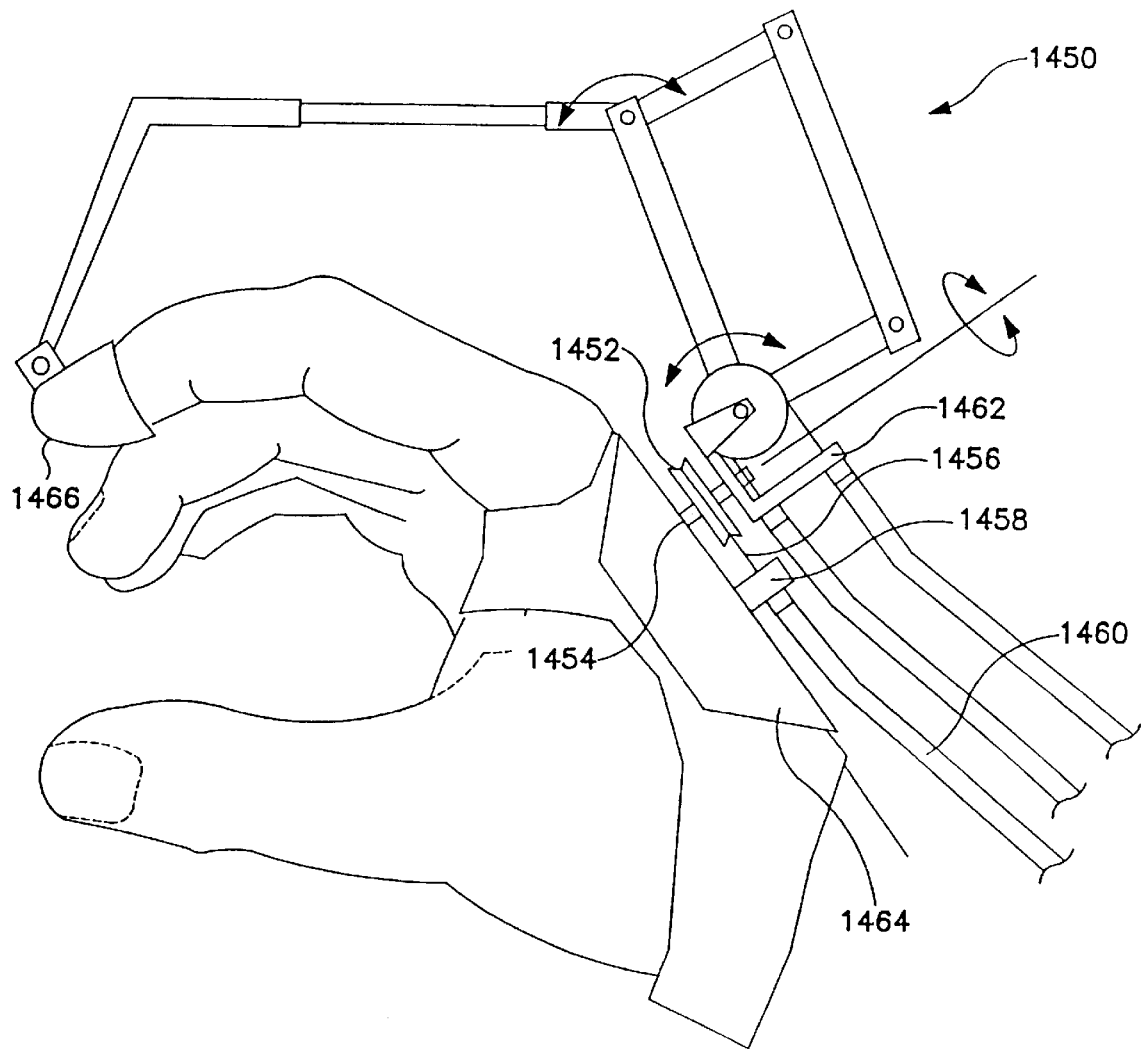
FIG. 14B is a side view of another alternative embodiment of the mechanical structure of an index-finger-controlling force-feedback device capable of exerting forces in the finger plane as well as the abduction/adduction plane.

FIG. 14b is an embodiment of the invention that is very similar to the device illustrated in FIG. 14a but adds an additional degree-of-freedom of force feedback. In this embodiment, a mechanical superstructure capable of exerting forces on the index finger is shown while similar structures which may be used for the other fingers are omitted for clarity. The device 1450 is designed such that an additional pulley assembly is added to the superstructure described in FIG. 14a. The pulley assembly consists of a pulley 1452, which is mounted at the pivot joint 1454, a tendon 1456 which wraps around the pulley and is routed into the tendon casing support 1458, and two tendon casings 1460 (one is visible) which are anchored into the casing support and serve as the force transmitting means from the force-producing means to the force applying means. The pulley 1452 is fixed to the pivot joint 1454, which in turn is fixed to the support 1462. They cannot move with respect to one another. The pivot joint 1454, and consequently the pulley 1452 and the support 1462, can rotate with respect to the backplate 1464.

In operation, device 1450 is capable of exerting the forces described in FIG. 14a as well as forces in the abduction/adduction plane of the finger by rotating the pulley 1452 about the pivot joint 1454. The net result is that complex 3-dimensional forces can be transmitted to the fingertips via the force applicator 1466.

Figure 15A:
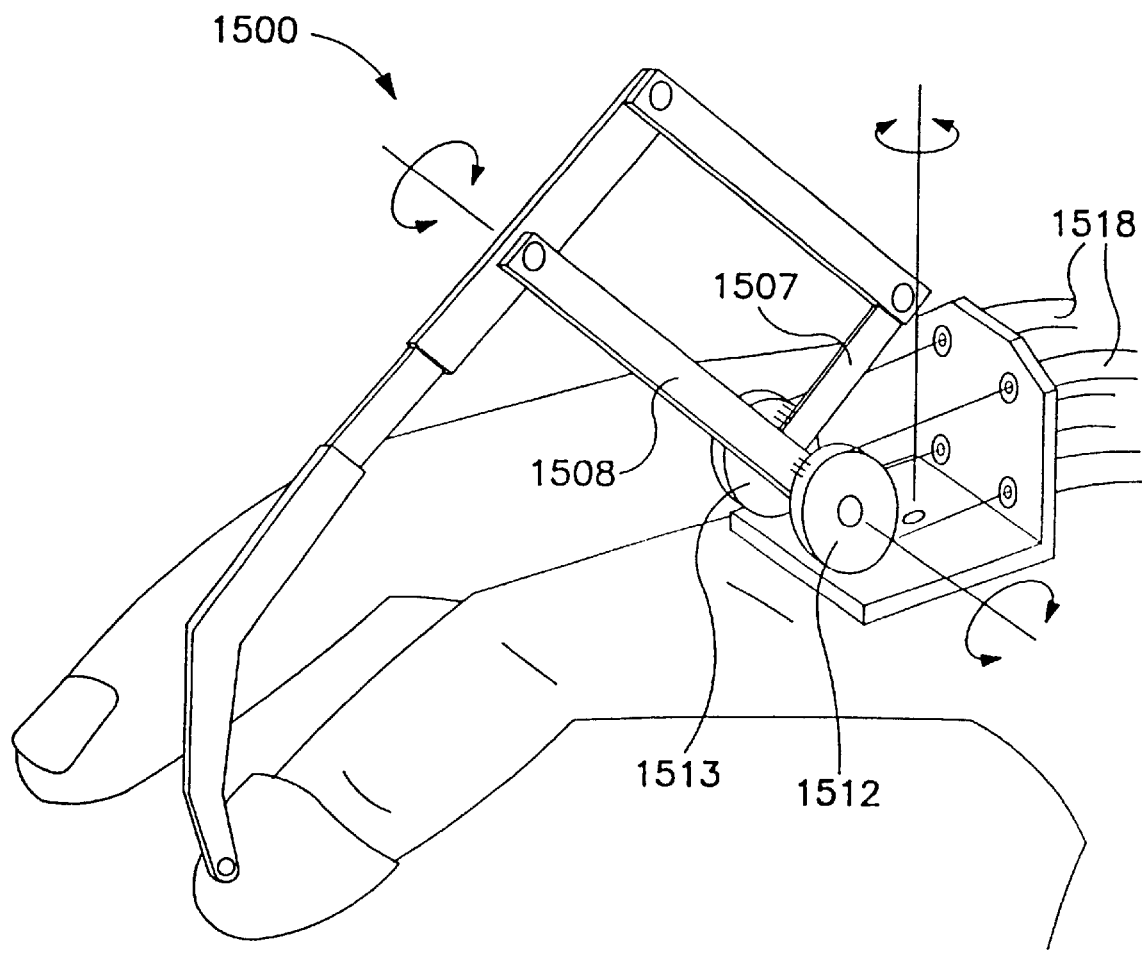
FIG. 15A is a diagrammatic illustration showing a perspective view of the embodiment of FIG. 14A.

FIG. 15a shows a perspective view of the same embodiment of the invention that is shown in plan view and described relative to FIG. 14a. It shows the second pulley 1513 (1413 in FIG. 14a) located behind the pulley 1512 (1412 in FIG. 14a). It also shows an unobstructed view of the four tendon casings 1518 (1418 in FIG. 14a). Pulley 1512 is attached to link 1508 of the five-bar linkage while pulley 1513 is attached to link 1507.

Figure 15B:
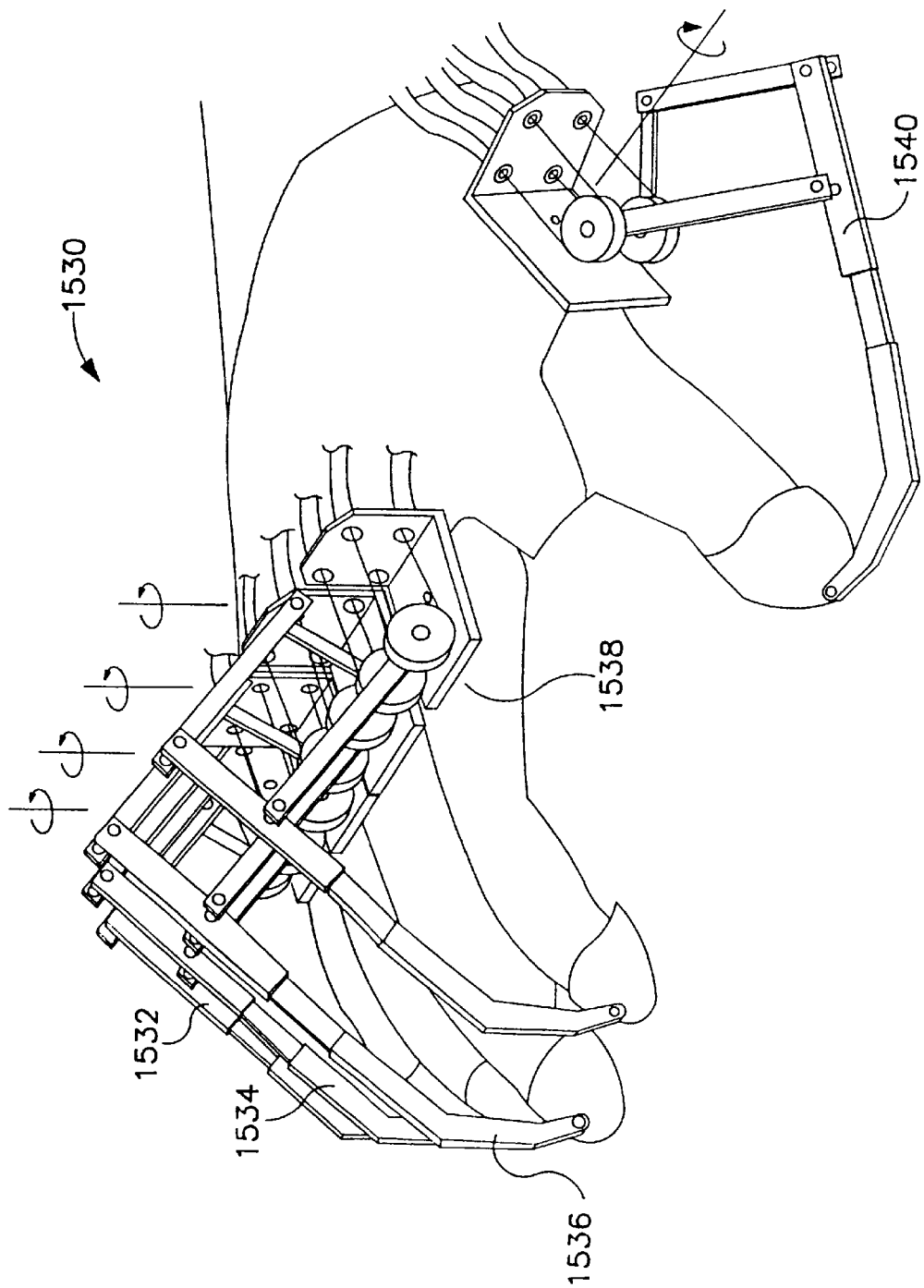
FIG. 15B is a perspective view of the embodiment of FIG. 14A showing mechanical structures above each finger.

FIG. 15b is a perspective view of the embodiment of the invention that is described in FIGS. 14a and 15a. Whereas the devices in FIGS. 14a and 15a show a structure implemented on a single finger, the device 1530 in this figure illustrates a mechanism with force-feedback structures (1532, 1534, 1536, 1538, 1540) on each of the five fingers of the hand. A simplified version of the device 1530 can be implemented with, for example, structures on the thumb 1540, the index 1538 and the middle finger 1536.

Figure 15C:
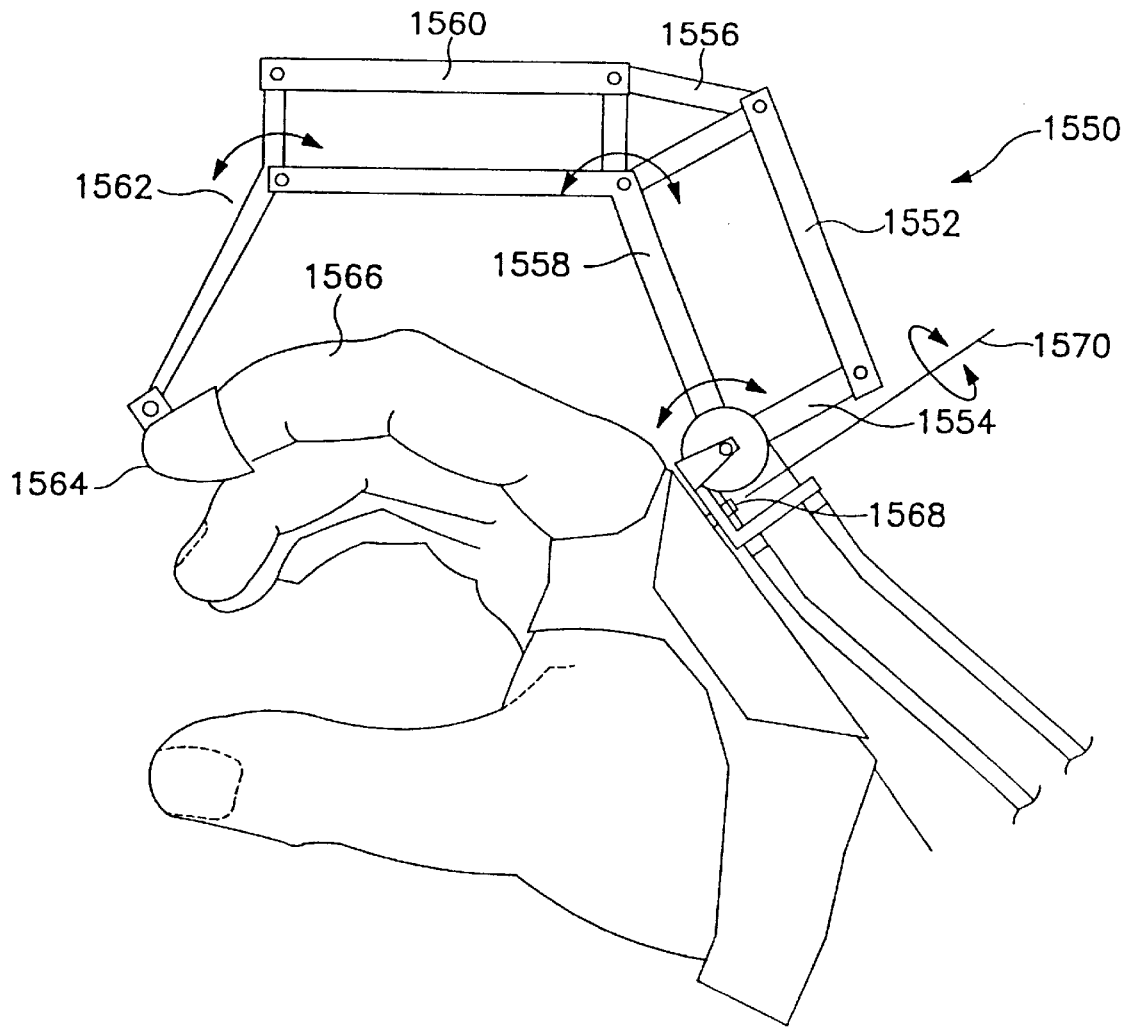
FIG. 15C a side view of another alternative embodiment of the mechanical structure presented in FIG. 15A.

FIG. 15c is an embodiment of the invention that uses a superstructure 1550 which exerts a force directly at the fingertip without attaching to other parts of the finger. As for the other mechanism described herein, the embodiment is shown for the index finger but it can be extended to the other fingers of the hand. It's operation is very similar to that of the device described in FIG. 14a. The difference is that the mechanism comprises two five-bar linkages instead of one. In this embodiment, the first five-bar linkage consists of two straight links 1552 and 1554, a triangular link 1556 and a v-shaped link 1558. The triangular link and the v-shaped link are also part of the second five-bar linkage which also consists of the straight link 1560 and another v-shaped link 1562 which attaches to the force applicator 1564 at one end. In this type of configuration, the second five-bar linkage mimics the motion of the first one, which is actuated as described in FIG. 14a. A third five-bar linkage could be added in series if so desired.

In operation, the mechanism behaves in a manner that is very similar to the mechanism described in FIG. 14a. The advantage of adding a second five-bar linkage is that for the full range-of-motion of the hand, the device 1550 keeps a lower profile than the one described in FIG. 14a. It will be able stay close to the index finger 1566 when the user makes a fist yet not extend high above the finger when it is hyper-extended. Additionally, the structure is free to rotate 1570 about a joint 1568 that enables it to track finger adduction/abduction without hindering it. It may be desirable to add another pulley/tendon assembly to exert adduction and abduction forces at the fingertip.

Figure 16A:
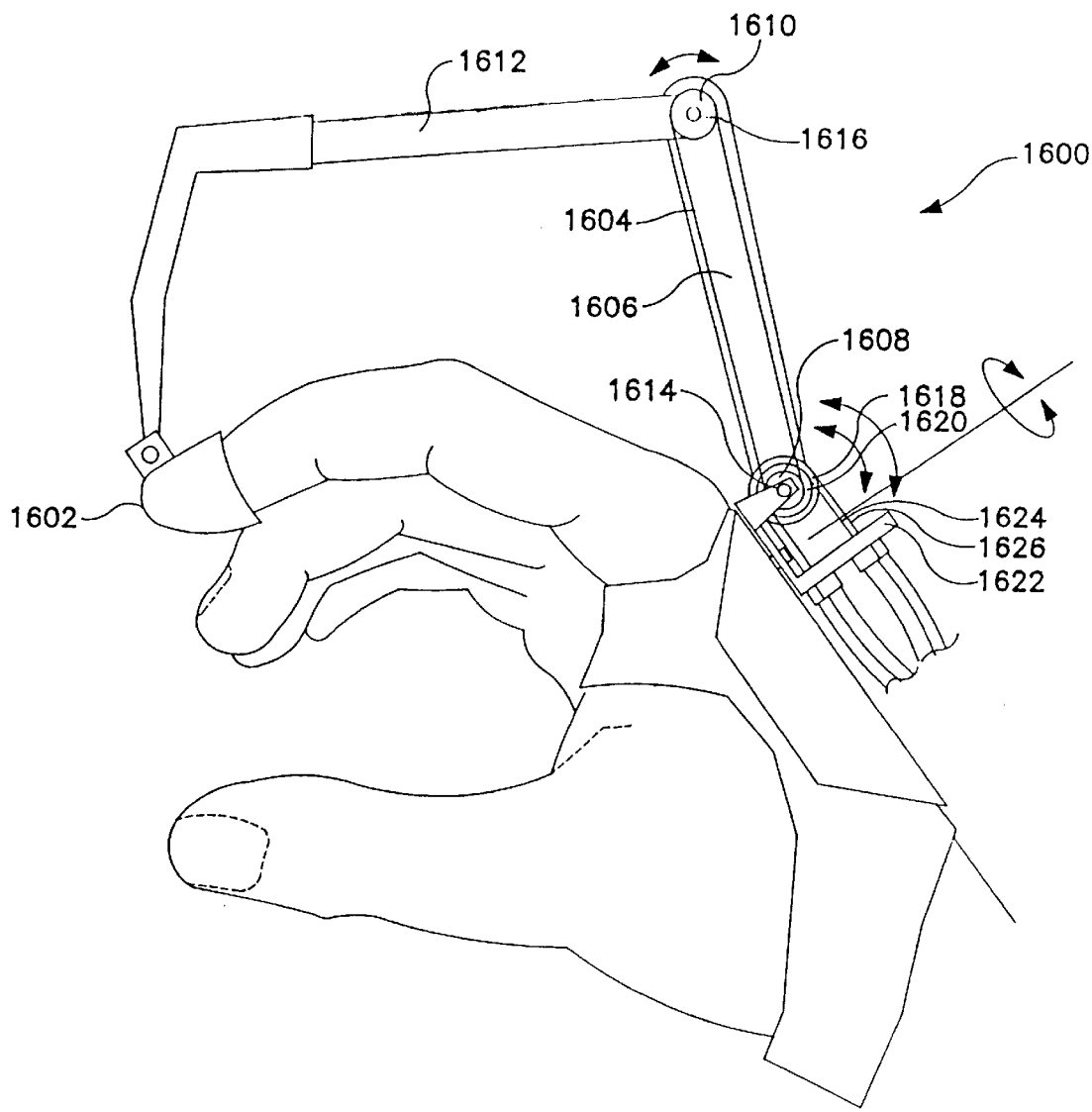
FIG. 16A is a diagrammatic illustration showing a side view of another alternative embodiment of the mechanical structure of an index-finger-controlling force-feedback device capable of exerting forces in the finger plane.

FIG. 16a is a variation of the embodiment of the invention described in FIG. 14a. It also exerts forces directly to the force applicator 1602 located at the fingertip, but instead of using a five-bar linkage to transmit the forces, it uses a tendon-based approach. Again, the superstructure 1600 is shown for the index finger, with the similar structures that may be used for the other fingers omitted for clarity. The tendon-based approach used in this mechanism acts similarly to the five-bar linkage in FIG. 14a except that the five-bar mechanism is replaced with a pair of pulleys 1608 and 1610 and a tendon 1604 which is anchored at both pulleys. A base link 1606 supports both pulleys 1608 and 1610 which are free to rotate about their respective joint shafts 1614 and 1616. Additionally, pulley 1610 is attached to link 1612 such that when it rotates, link 1612 rotates with respect to the base link 1606. Similarly, pulley 1608 rotates about shaft 1614 but is connected to pulley 1610 via tendon 1604 such that any rotation of pulley 1608 causes a corresponding rotation in pulley 1610. The mechanism includes two other pulleys 1618 and 1620 which correspond to pulleys 1412 and 1413 respectively in FIG. 14*a*. Pulley 1618 is attached to the base link 1606 and is free to rotate about shaft 1614 such that when the pulley rotates, the base link rotates with respect to the support 1622. Similarly, pulley 1620 is attached to pulley 1608 and is free to rotate about shaft 1614 such that when pulley 1620 rotates, it cause a corresponding rotation in pulley 1608 and consequently a rotation in pulley 1610.

In operation, the mechanism behaves like the mechanism described in FIG. 14*a* where rotating the bases pulleys 1618 and 1620 using tendons 1624 and 1626 causes forces to be produced at the force applicator 1602 located at the fingertip.

Figure 16B:
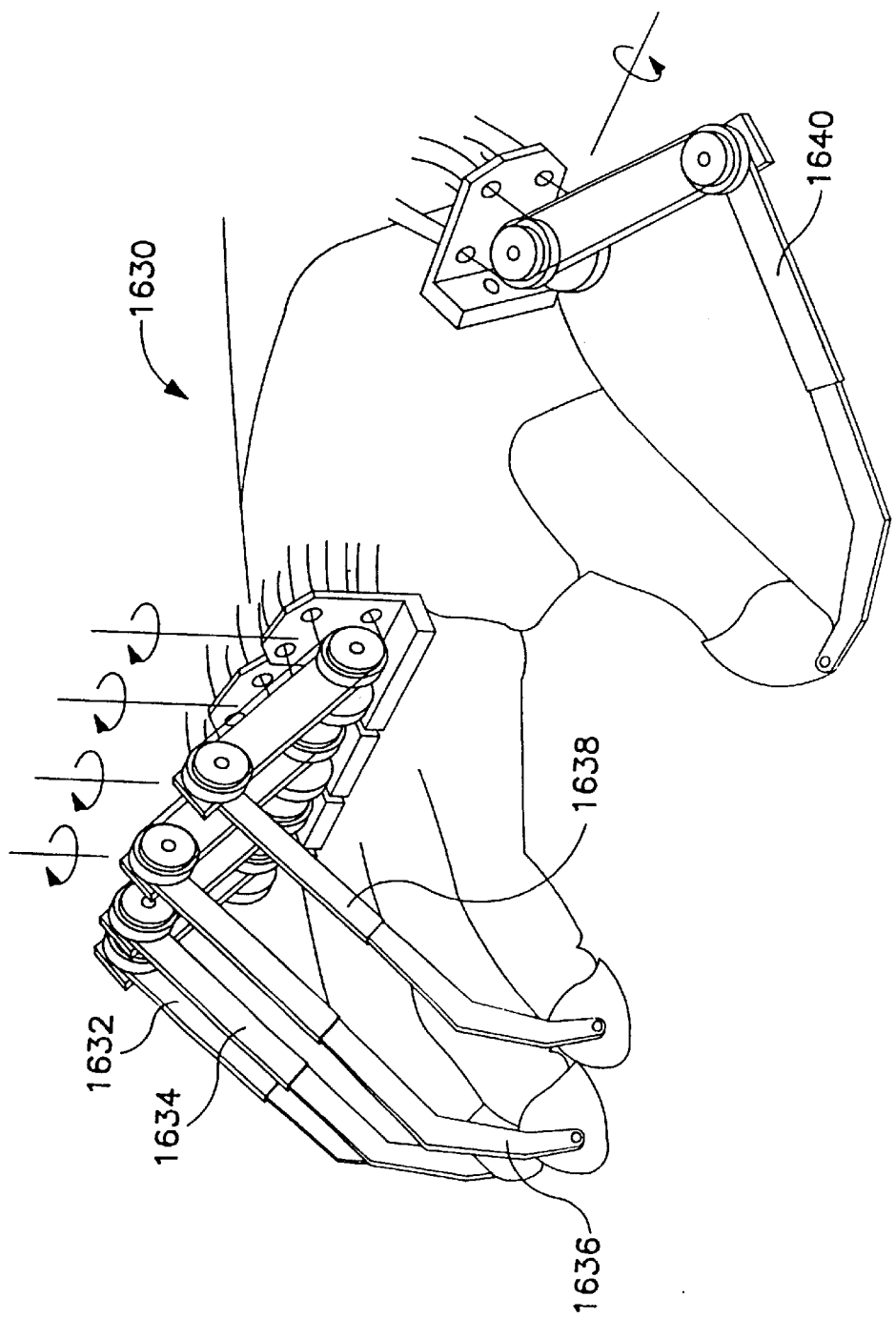
FIG. 16B is a perspective view of the mechanical structure of a whole-hand-controlling force-feedback device using the mechanism presented in FIG. 16A.

FIG. 16*b* is a perspective view of the embodiment of the invention that is described in FIG. 16*a*. Whereas the device in FIG. 16*a* shows a structure implemented on a single finger, the device 1630 in this figure illustrates a mechanism with force-feedback structures (1632, 1634, 1636, 1638, 1640) on each of the five fingers of the hand. A simplified version of the device 1630 can be implemented with, for example, structures on the thumb 1640, the index 1638 and the middle finger 1636.

Figure 16C:
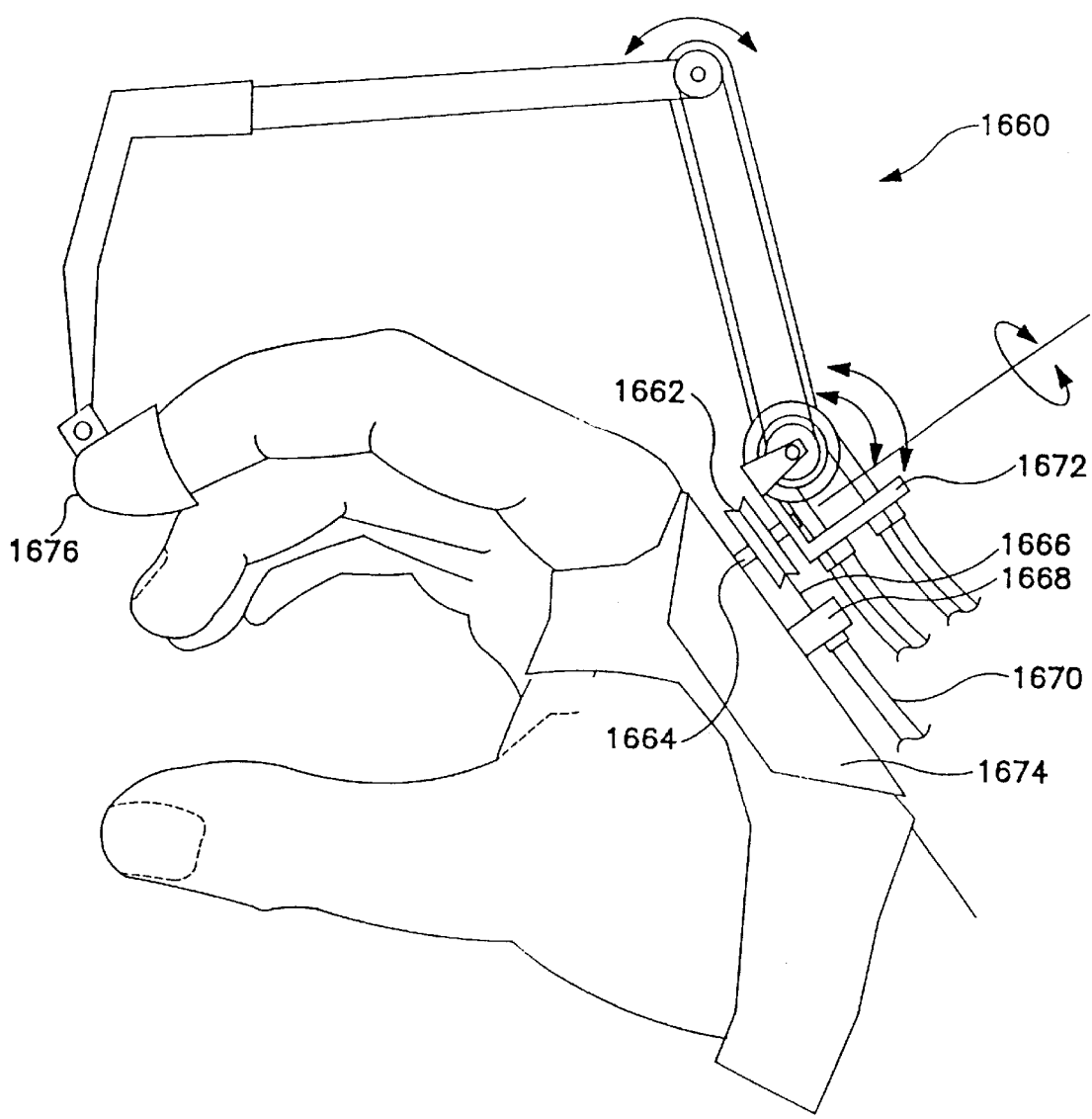
FIG. 16C is a side view of another alternative embodiment of the mechanical structure of an index-finger-controlling force-feedback device capable of exerting forces in the finger plane as well as the abduction/adduction plane.

FIG. 16*c* is an embodiment of the invention that is very similar to the device illustrated in FIG. 16*a* but adds an additional degree-of-freedom of force feedback. In this embodiment, a mechanical superstructure capable of exerting forces on the index finger is shown while similar structures which may be used for the other fingers are omitted for clarity. The device 1660 is designed such that an additional pulley assembly is added to the superstructure described in FIG. 16*a*. The pulley assembly consists of a pulley 1662, which is mounted at the pivot joint 1664, a tendon 1666 which wraps around the pulley and is routed into the tendon casing support 1668, and two tendon casings 1670 (one is visible) which are anchored into the casing support and serve as the force transmitting means from the force-producing means to the force applying means. The pulley 1662 is fixed to the pivot joint 1664, which in turn is fixed to the support 1672. They cannot move with respect to one another. The pivot joint 1664, and consequently the pulley 1662 and the support 1672, can rotate with respect to the backplate 1674.

In operation, device 1660 is capable of exerting the forces described in FIG. 16*a* as well as forces in the abduction/adduction plane of the finger by rotating the pulley 1662 about the pivot joint 1664. The net result is that complex 3-dimensional forces can be transmitted to the fingertips via the force applicator 1676.

Figure 17:
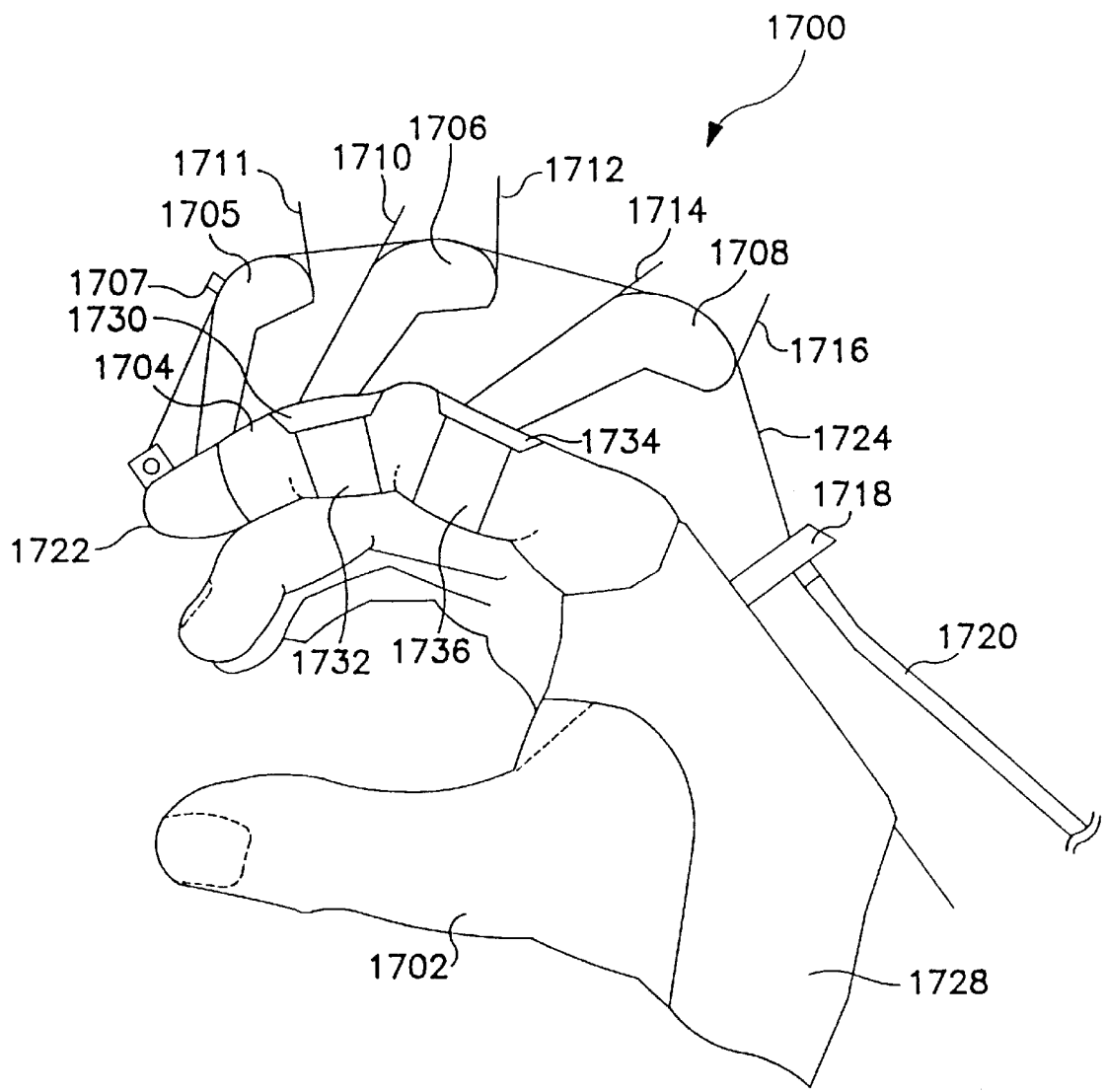
FIG. 17 is a side view of another alternative embodiment of the mechanical structure of an index-finger-controlling force-feedback device capable of exerting forces in the finger plane.

FIG. 17 illustrates an embodiment of the invention which utilizes a cam-based superstructure 1700 requiring few moving parts which is worn over an instrumented glove 1702 capable of measuring hand position. In this embodiment, a mechanical superstructure capable of exerting forces on the index finger is shown while the structures that would be used for the other fingers are omitted for clarity. The device 1700 comprises a superstructure having an offset front cam 1705 with front 1707 and rear 1711 tendon guides, an offset middle cam 1706 with front 1710 and rear 1712 tendon guides, an offset rear cam 1708 with front 1714 and rear 1716 tendon guides and a base support 1718 which anchors the tendon casing 1720 that serves as the force-transmitting means. For exerting forces at the fingertip, a force applicator 1722 to which is attached a tendon 1724, is used. The tendon 1724 is routed in a guiding groove at the top of the front cam 1705 passing through tendon guides 1707 and 1711 and then in the guiding grooves at the top of the middle 1706 and rear 1708 cams, passing through their respective tendon guides. From the rear cam 1708, the tendon 1724 goes into the tendon casing 1720, which is affixed to the back of the base support. The base support 1718 is attached to the hand by any convenient means 1728, such as straps, belts or the like. In addition, the front cam 705 attaches to the distal phalanx of the finger via the force applicator 1722. The middle cam 1706 attaches to the middle phalanx by an attachment device 1732, which may be any convenient means, such as a strap or belt. Conveniently, the middle cam may be mounted on a base 1730 to which the attachment means 1732 is affixed. Similarly, the rear cam 1708 attaches to the proximal phalanx of the finger by an attachment device 1736, which may be any convenient means, such as a strap or belt. Again, the rear cam 1708 may be mounted on a base 1734 to which the attachment means 736 is fixed.

In operation, the instrumented glove 1702 acts as the position-sensing means for the device. Under little or no tendon force, the finger is free to move and flex in any direction while the position sensing in the hand ensures that the tendon slack will be kept to a minimum, ensuring prompt response when forces are desired at the fingertip. Forces and torques are transmitted to the fingertip and joints respectively using a single tendon 1724 per finger. Under tension, the tendon will pull up on the force applicator 1722 thus producing a reactive force at the fingertip. Simultaneously, the tendon will push down on the three offset cams 1705, 1706 and 1708. This effect will produce reactive torques at each of the three finger joints.

Figure 18:
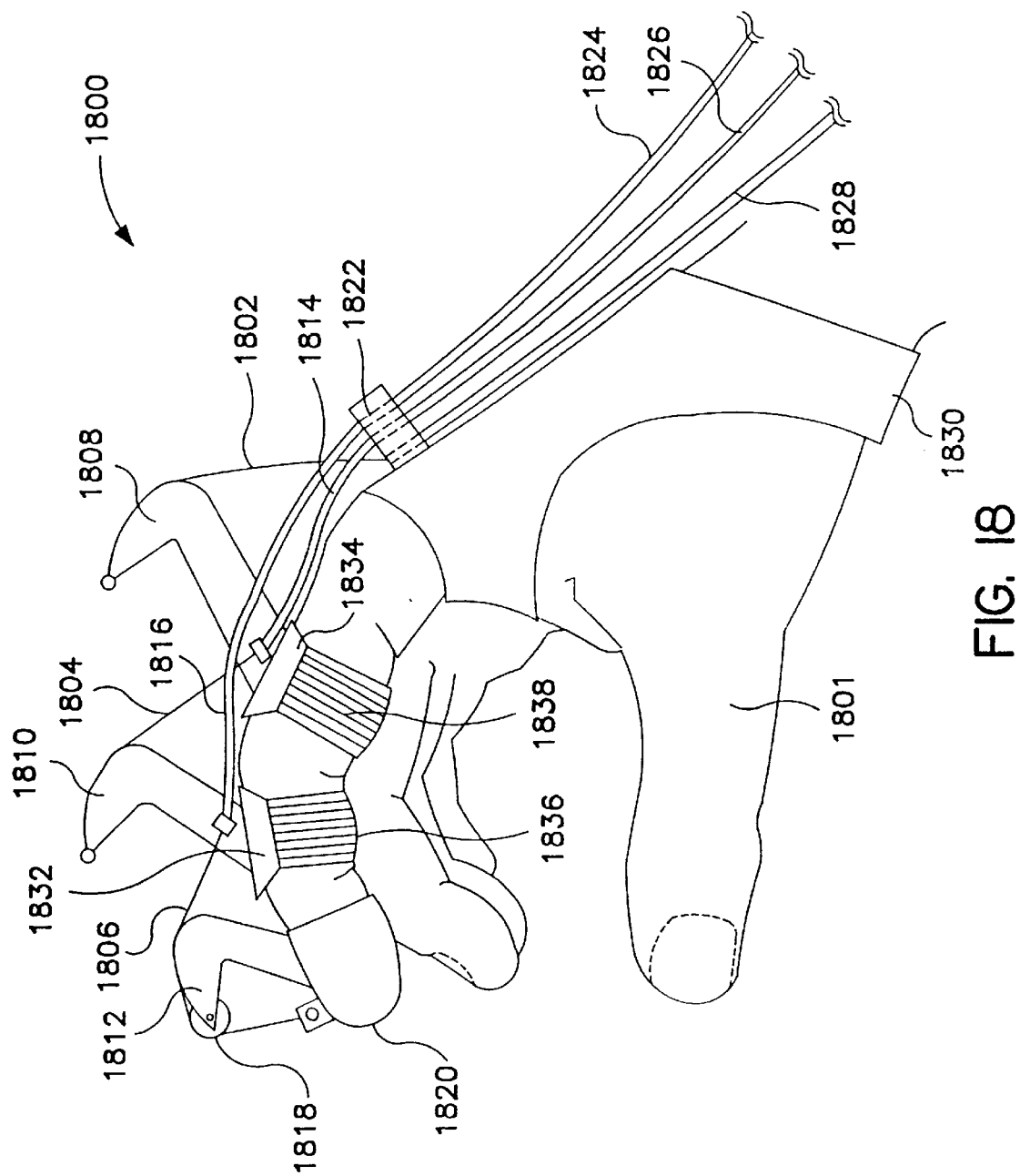
FIG. 18 is a side view of another alternative embodiment of the mechanical structure of an index-finger-controlling force-feedback device capable of exerting forces in the finger plane.

FIG. 18 illustrates an embodiment of the invention which utilizes a cam-based superstructure 1800 which is worn over an instrumented glove 1801 capable of measuring hand position. In this embodiment, a mechanical superstructure capable of exerting forces on the index finger is shown while the structures that would be used for the other fingers are omitted for clarity. The device 1800 comprises a superstructure having an offset front cam 1812, an offset middle cam 1810, an offset rear cam 1808 and a base support 1822 which anchors the three tendon casings 1824, 1826 and 1828 that serve as the force-transmitting means. For exerting forces at the fingertip and torques at the distal finger joint, a force applicator 1820 to which is attached a tendon 1806, is used. Conveniently, the tendon 1806 is routed around a pulley 1818 and then through a guiding groove at the top of the front cam 1812 and then through a flexible tendon casing 1816 which is anchored at the base of the middle offset cam 1810 at one end, and at the base support 1822 at the other. For exerting torques at the middle finger joint, a tendon 1804 which is fixed to the front of the middle cam 1810 is used. The tendon 1804 is routed in a guiding groove at the top of the middle cam 1810 and then through a flexible tendon casing 1814 which is anchored at the base of the rear cam 1808 at one end, and at the base support 1822 at the other. Finally, for exerting torques at the base finger joint, a tendon 1802 which is fixed to the front of the rear cam 1810 is used. The tendon 1802 is routed in a guiding groove at the top of the rear cam 1810 and then directly to the base support 1822 at the other. The three tendons 1806, 1804 and 1802 enter the base support 1822 on one side and exit into tendon casing 1824, 1826 and 1828 respectively on the other. The base support 1822 is attached to the hand by any convenient means 1830, such as straps, belts or the like. In addition, the front cam 1812 attaches to the distal phalanx of the finger via the force applicator 1820. The middle cam 1810 attaches to the middle phalanx by an attachment device 1836, which may be any convenient means, such as a strap or belt. Conveniently, the middle cam may be mounted on a base 1832 to which the attachment means 1836 is affixed. Similarly, the rear cam 1808 attaches to the proximal phalanx of the finger by an attachment device 11838, which may be any convenient means, such as a strap or belt. Again, the rear cam 1808 may be mounted on a base 1834 to which the attachment means 1838 is fixed.

In operation, the instrumented glove 1801 acts as the position-sensing means for the device. Under little or no tendon force, the finger is free to move and flex in any direction while the position sensing in the hand ensures that the tendon slack will be kept to a minimum, ensuring prompt response when forces are desired at the fingertip. Forces and torques are transmitted to the fingertip and joints respectively using three tendons 1806, 1804 and 1802 per finger. Under tension, tendon 1806 will pull up on the force applicator 1820 thus producing a reactive force at the fingertip as well as a reactive force at the distal finger joint. Tendon 1804 will pull on the middle offset cam 1810 which will produce a reactive torque at the middle finger joint. Similarly, tendon 1802 will pull on the rear offset cam 1808 which will produce a reactive torque at the proximal finger joint. Unlike the device presented in FIG. 17, device 1800 makes it possible to control the torques and forces being exerted at each joint individually.

Figure 19A:
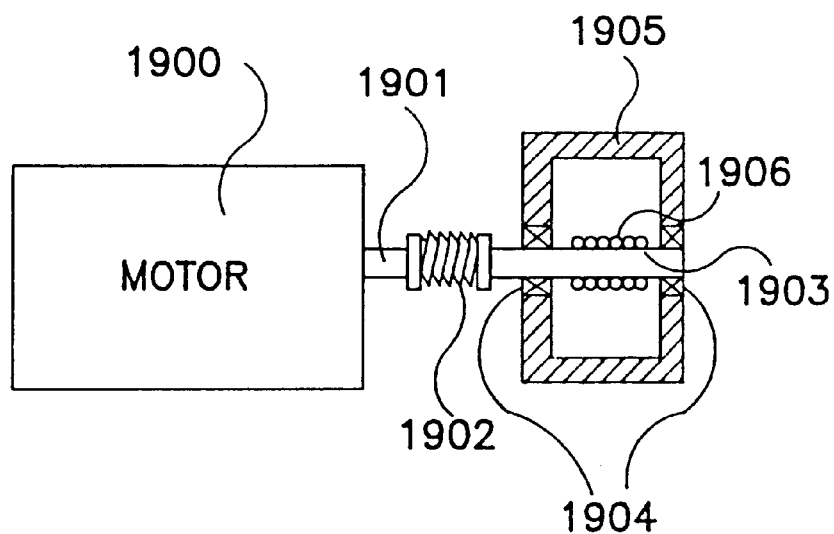
FIGS. 19A and 19B are diagrammatic illustrations of a side cross-section and a perspective view of an illustrative embodiment of a motor-spool assembly, which demonstrates how a motor may control tendon position.
Figure 19B:
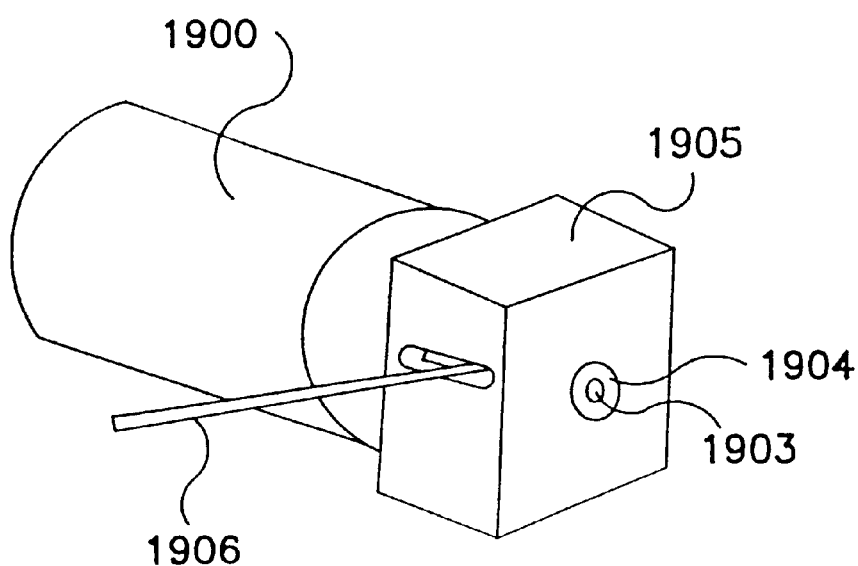

FIGS. 19A and 19B are diagrammatic illustrations of a side cross-section and a perspective view of an illustrative embodiment of a motor-spool assembly, which demonstrates how a motor may control tendon position. Motor 1900 with shaft 1901 is connected to spool shaft 1903 by optional coupler 1902. Shaft 1903 rotates in spool housing 1905 by bearings 1904. Tendon 1906 is wound around the shaft 1903.

Figure 20:
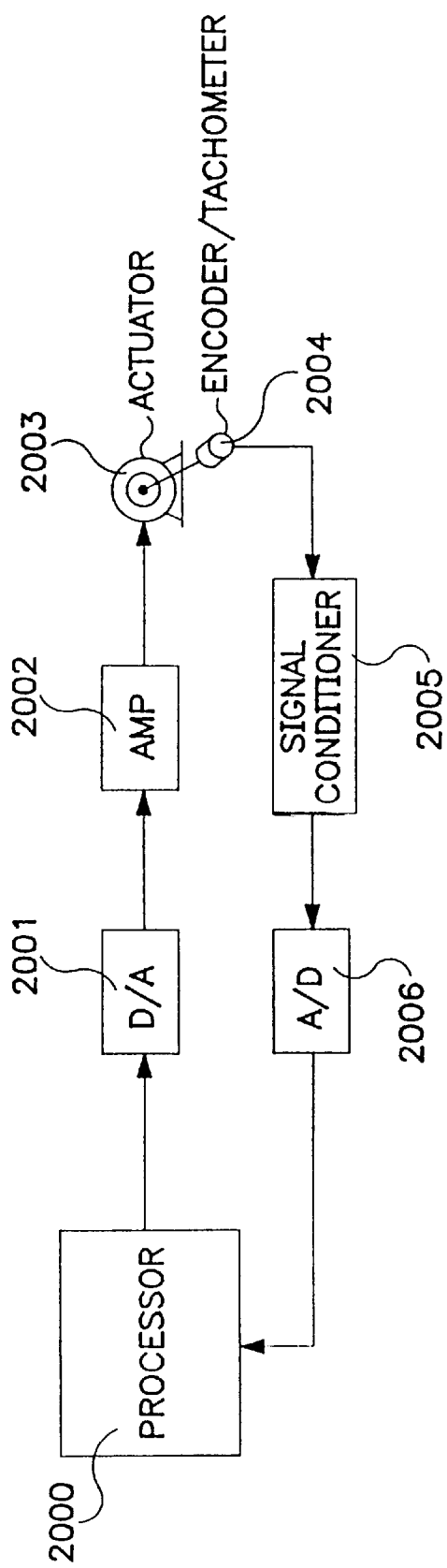
FIG. 20 is a block diagram of a canonical motor-control system.

FIG. 20 is a block diagram of a canonical motor-control system. The processor 2000 provides a digital signal to the digital-to-analog converter 2001, which outputs an analog voltage which is amplified by the amplifier 2002 which powers the motor 2003. The motor may have an encoder, tachometer, or other rotation-monitoring means 2004, which provides a signal to the signal conditioner 2005. The signal-conditioner output is digitize by the analog-to-digital converter 2006, which provides the rotation information in digital form to the processor 2000.

Figure 21A:
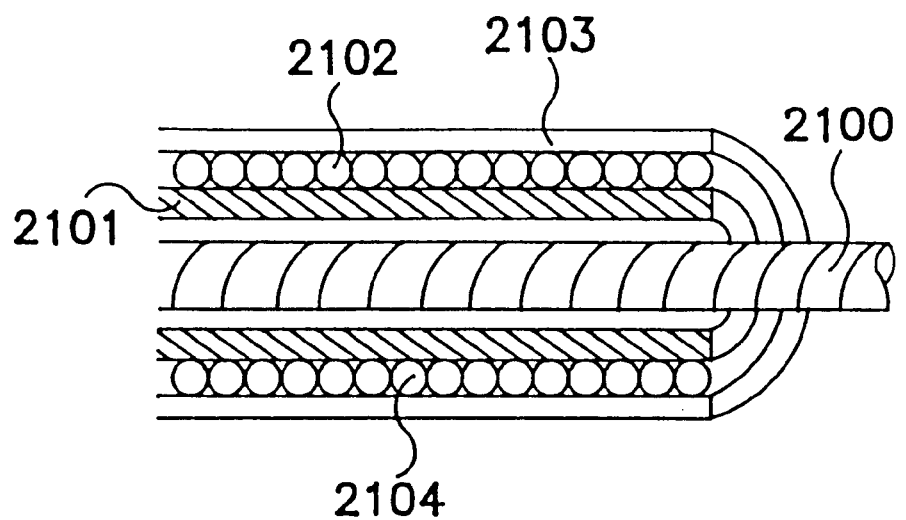
FIGS. 21A and 21B are a longitudinal cross section of a flexible tendon in a useful embodiment of a flexible sheath tendon guide.
Figure 21B:
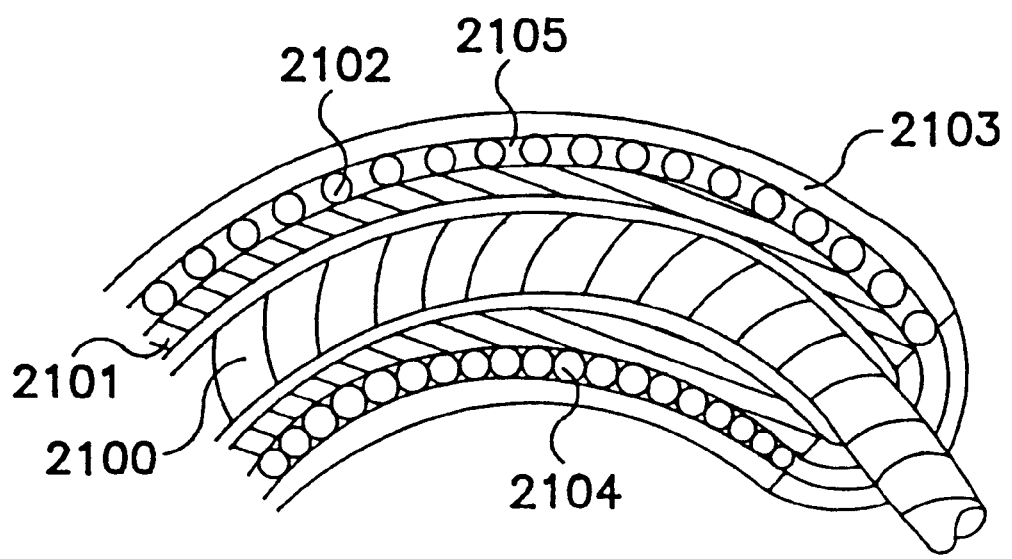

FIGS. 21A and 21B are a longitudinal cross section of a flexible tendon in a useful embodiment of a flexible sheath tendon guide. FIG. 21A shows the tendon-sheath structure unflexed, while FIG. 21B shows the tendon-sheath structure flexed. The sheath comprises a flexible inner layer 2101, typically Teflon®, or any other lubricious, flexible, low-compressibility material through which the flexible, high-tensile strength tendon 2100 passes. Surrounding the inner layer is a spring winding 2102 and 2104 which adds considerable compressive strength to the sheath, while still allowing low resistance to flexing. Surrounding the winding layer is a flexible encapsulating layer 2103, which prevents the coils from buckling on top of one another, in addition to providing a smooth outer surface. In FIG. 21B, where the tendon-sheath structure is shown flexed from top to bottom, the top surface of the winding layer 2102 is shown where the individual wires separate creating a space 2105 when flexed, providing little resistance to bending. The bottom surface of the winding layer 2104 still has all wires firmly against one another, providing strong compressive strength.

FIGS. 22A–22E are diagrammatic illustrations showing various pinned joints which may be employed when routing a tendon 2200 from the actuator to its desired final destination. These "rigid" joint structures provide an alternative to the flexible joint structure described in FIGS. 21A and 22B. FIG. 22A comprises two links 2201 and 2202 which are pinned together via a pin 2203. Each link typically encloses the tendon 2200, and may be of any convenient cross-sectional shape, such as round or square. As shown, a pulley 2204 also rotates about this axis. The tendon 2200 passes across the pulley, and due to the pulley's placement at the joint axis, the tendon will always pass through the same location in each of the links independent of link angle. A hole in each link endcap 2205 further guides the tendon. The joint angle between the two links may optionally be measured by any convenient means, such as an encoder, potentiometer, resolver, and the like 2207, or a resistance-varying strain-sensing goniometer 2208, such as provided by Kramer, U.S. Pat. No. 5,047,952. Among other things, the angle information may be used to correct for the change in tendon length as it passes along the pulley. Link-end surfaces 2206 may be made such that they press against each other and prevent the links from sufficiently aligning, whereby the tendon could draw away from the pulley.

FIG. 22B is a top view, and FIG. 22C is an end cross-section view, where a plurality of tendons 2212 are routed across a plurality of pulleys 2213. Two links 2209 and 2210 are connected by pin 2211, which provides the rotation axis for the pulleys 2213. When multiple tendons are routed, each tendon as shown may represent an independently-controlled tendon. A pair of tendons as shown may also comprise a single tendon, where one visible tendon is moving from the actuator, while the paired tendon is actually the returning portion of the tendon. Such a configuration is useful when it is desirable to have a tendon form a complete loop.

FIG. 22D is a diagrammatic illustration where two links 2214 and 2215 can pass through alignment without concern that the tendon 2221 might lose contact with a guiding pulley. The two links 2214 and 2215 are shown pinned by joint 2216. The pulleys 2217 and 2218 are pinned to rotate on the link 2215 via pins 2219 and 2220, respectively. With this configuration, the path of the tendon relative to link 2215 remains constant, since that is the link to which the pulleys are attached. However, relative to link 2214, the path of the tendon varies with the angle of link 2215.

FIG. 22E is a diagrammatic illustration of a dual-tendon-guide pulley arrangement. The principle of operation here is similar to the operation of FIG. 22D. Links 2222 and 2223 rotate relative to each other via pin 2224. Pulley 2225 also rotates about that pin. There are two other pulleys 2226 and 2227 which rotate on link 2223 via shafts 2228 and 2229, respectively. Tendon 2230 is guided by pulleys 2225 and 2226, while tendon 2231 is guided by pulleys 2225 and 2227. As with FIG. 22D, when two pulleys are used, with one pulley on each side of the tendon, the links may align without concern that the tendon may lift from contact with a pulley. Various joint-angle sensor as previously mentioned may again be used. The joint-angle information may also be used to correct for the change in tendon length which occurs when the one link rotates relative to the other. This joint structure is particularly useful when two tendons are desired, or when a single tendon loop is desired, where tendon 2230 and 2231 represent outgoing and return portions of a single tendon loop.

Figure 23A:
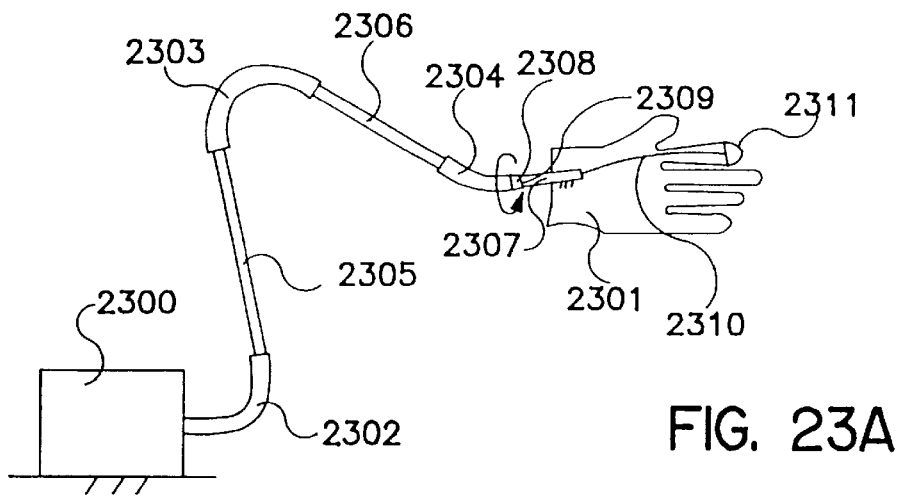
FIGS. 23A–23D are diagrammatic illustrations of various convenient force-transmitting means.

FIGS. 23A–23D are diagrammatic illustrations of various convenient force-transmitting means. FIG. 23A comprises a stationary actuator module 2300 and a plurality of rigid straight tendon guides 2305, 2306, 2307 and 2308, connected by guiding joints 2302, 2303 and 2304. Each of the guiding joints may be a flexible joint (such as in FIGS. 21A and 21B), a rigid pinned joint (such as in FIGS. 22A–22E), and the like. In such a configuration, the majority of tendon friction losses are associated with a finite portion of the transmission, namely the joint regions. Rigid portion 2308 may rotate axially relative to rigid portion 2307, which is supported by the hand or glove 2301. Tendon 2310 terminates at the desired location, which in the case of FIG. 23A is the fingertip 2311.

Figure 23B:
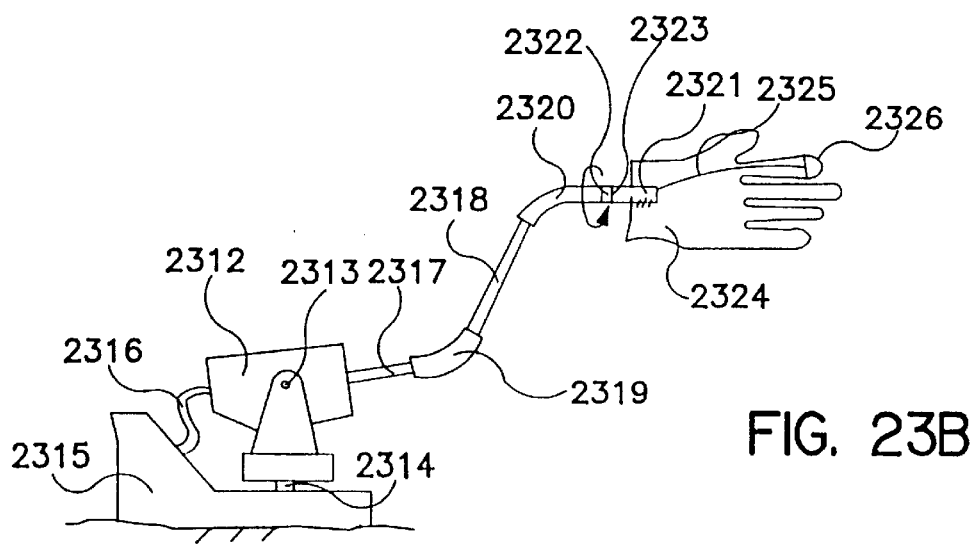

FIG. 23B is similar to FIG. 23A, however, the actuator module 2312 pivots about horizonal axis 2313 and rotates about vertical axis 2314 to minimize the joint flexure of joints 2319 and 2320, which results in friction losses in the tendon. Control signals may come from the fixed portion of the housing 2315 and are transmitted to the actuator module 2312 via connection means 2316. Since the actuator module is able to reorient itself depending on the location of the end of the force-transmitting means, which in this example is the hand, only two joints 2319 and 2320 are necessary. The joints connect rigid straight portions 2317, 2318, 2322 and 2321. Rigid portion 2322 may rotate axially relative to rigid portion 2321 via joint 2323. Rigid portion 2321 is supported by the hand or glove 2324. The tendon 2325 terminates in this example at the fingertip 2326.

Figure 23C:
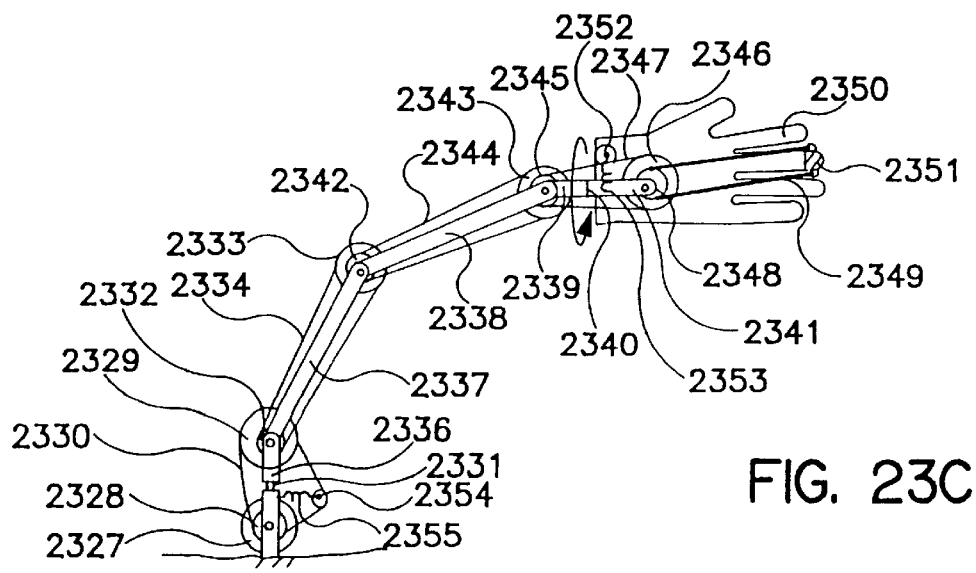

FIG. 23C is a diagrammatic illustration of how rotational movement from a motor may be transmitted to rotational movement at a terminal point, such as at the hand. In particular, this manner of transmitting rotational movement is useful when used in conjunction with structures such as the structure comprising links 2335, 2336, 2337, 2338, 2339, and 2341 connected by revolute joints. In FIG. 23C, the transmission of rotational movement is accomplished by a concatenation of tendon loops and pulleys. In this case, the pulleys rotate co-axially with the axes of the links that separate them. The transmitted rotational movement may be used in any convenient manner, such as providing a pulling or pushing force, a rotational torque, and the like. Motor 2327 with pulley 2328 drives pulley 2329 via tendon 2330. In this example, the motor is stationed relative to link 2335, about which the entire structure, beginning with link 2336, may rotate about axial joint 2331. To accommodate for the resulting change in tendon loop length, roller pulley 2354 with tensioning spring means 2355 may be used. Typically, other alignment pulleys are also required to prevent the tendon loop from coming off the pulleys during rotation; however, they are not shown in the figure for clarity. Pulley 2329 is attached to pulley 2332 which drives pulley 2343 via tendon loop 2334. Pulley 2343 is connected to pulley 2342 which drives pulley 2343 via tendon loop 2344. Pulley 2343 is connected to pulley 2345 which drives pulley 2346 via tendon loop 2347. Pulley 2348 transmits force to the desired end location. In this illustrative example, pulley 2348 imparts abduction/adduction forces onto the fingertip 2351 of a hand 2350 via tendon 2349; however, any of a variety of forces or torques may be imparted to the hand or other body part. In this example, link 2339 may rotate relative to link 2341 about axial joint 2340. To account for the change in tendon loop length during rotation, roller pulley 2352 with tensioning spring means 2353 may be used. In practice, other alignment pulleys are used with this axial joint to ensure that the tendon loop doesn't come off pulleys 2345 and 2346. The joints of this structure may have associated joint-angle measuring means, such as encoders, flex sensors, and the like, and the joints may also be actively driven such that the last link 2341 is forcibly drive to a known or desired position relative to the base link 2335.

Figure 23D:
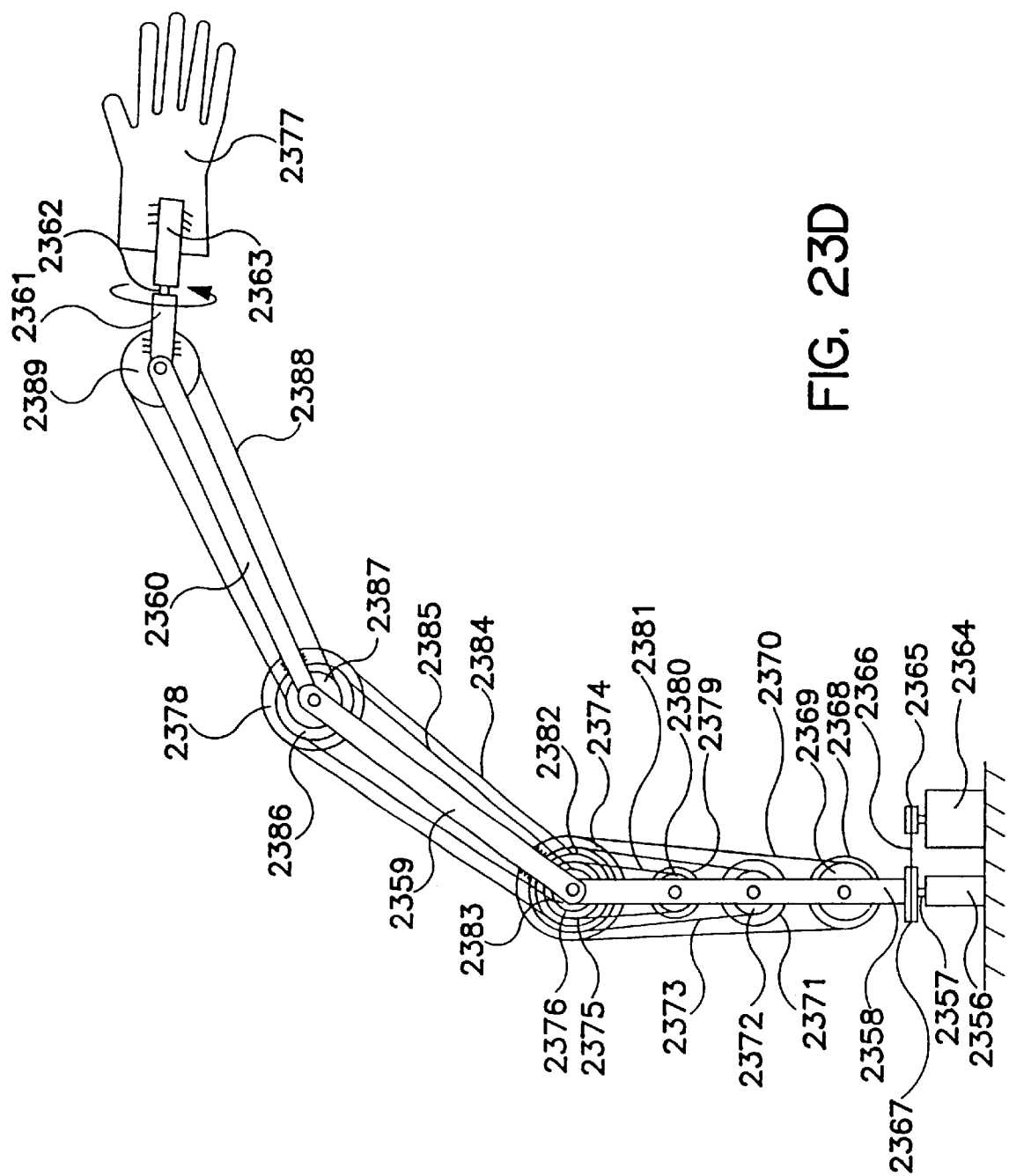

FIG. 23D is a diagrammatic illustration of how a structure similar to FIG. 23C with a set of links connected by revolute joints may be forcibly driven into position, where all actuators are located near the base link. The grounded-force actuating device of FIG. 23D may be used to provide grounded forces to a portion of the body, such as the hand, particularly when there is another device associated with the hand which provides forces to the hand with respect to another body part, such as provided in FIG. 1, and the like. When the device of FIG. 23D is used to provide grounded forces to the hand, it is also a convenient structure by which forces may be transmitted to the hand for use by the hand-referenced force-feedback device, such as provided in FIG. 1, and the like.

In FIG. 23D, motor 2364 is connected to pulley 2365 which drives rotation pulley 2367 via tendon loop 2366. By activating motor 2364, link 2358 is caused to rotate about base link 2356 on shaft 2357. Motor 2368 is connected to pulley 2369 which drives pulley 2374 via tendon loop 2370, and where pulley 2374 is connected to link 2359 such that rotation of motor 2368 causes link 2359 to rotate. Motor 2371 is connected to pulley 2372 which drives idler pulley 2382 via tendon loop 2373. Idler pulley 2382 is connected to pulley 2375 which drives pulley 2378 via tendon loop 2384, and where pulley 2378 is connected to link 2360, such that rotation of motor 2371 causes rotation in link 2360. Motor 2379 is connected to pulley 2380 which drives idler pulley 2376 via tendon loop 2381. Idler pulley 2376 is connected to pulley 2383 which drives idler pulley 2386 via tendon loop 2385. Idler pulley 2386 is connected to pulley 2387 which drives pulley 2389 via tendon loop 2388. Pulley 2389 is connected to link 2361 about which the terminal link 2363 may rotate about axial joint 2362. In this figure, terminal link 2363 is affixed to the hand or glove 2377. It is often desirable to have joint-angle position-sensing means associated with the joints connecting the links, such as encoders, potentiometer, flex sensors and the like. Such joint-angle position-sensing means are not explicitly shown in FIG. 23D for clarity.

Figure 24:
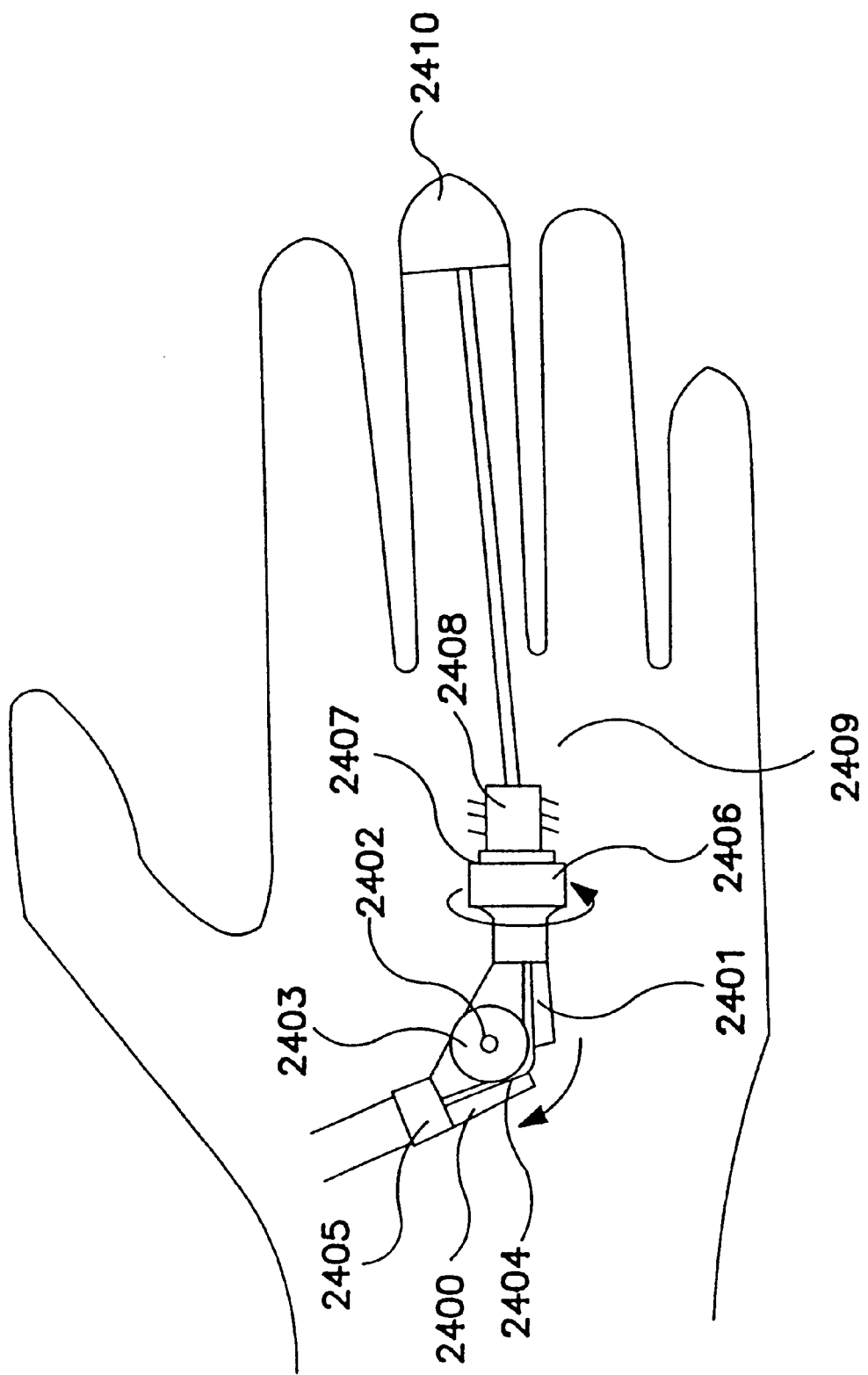
FIG. 24 is a diagrammatic illustration of a pinned joint, such as provided in FIG. 22A, being used to transmit tendon tension to the hand.

FIG. 24 is a diagrammatic illustration of a pinned joint, such as provided in FIG. 22A, being used to transmit tendon tension to the hand. Links 2400 and 2401 are connected by axis 2402. Tendon guide sheath 2405 is connected rigidly to link 2400, and rotary coupler 2406 is connected to link 2401. Rotary coupler 2406 rotates about axial joint 2407 relative to mating coupler link 2408, which is attached to the glove or hand 2409. Pulley 2403 rotates about axis 2402. Tendon 2404 passes around pulley 2403, through the rotary-link structure comprising links 2406 and 2408, and onto the fingertip 2410 or any other desirable terminal-tendon location.

Figure 25A:
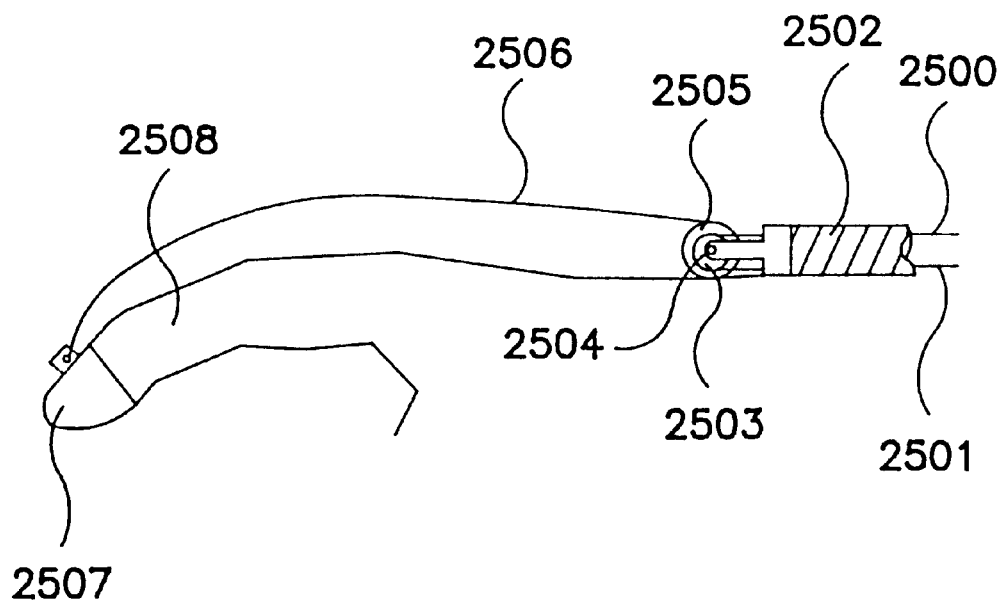
FIGS. 25A and 25B are diagrammatic illustrations of useful conversion of the movement of a circulating tendon loop.
Figure 25B:
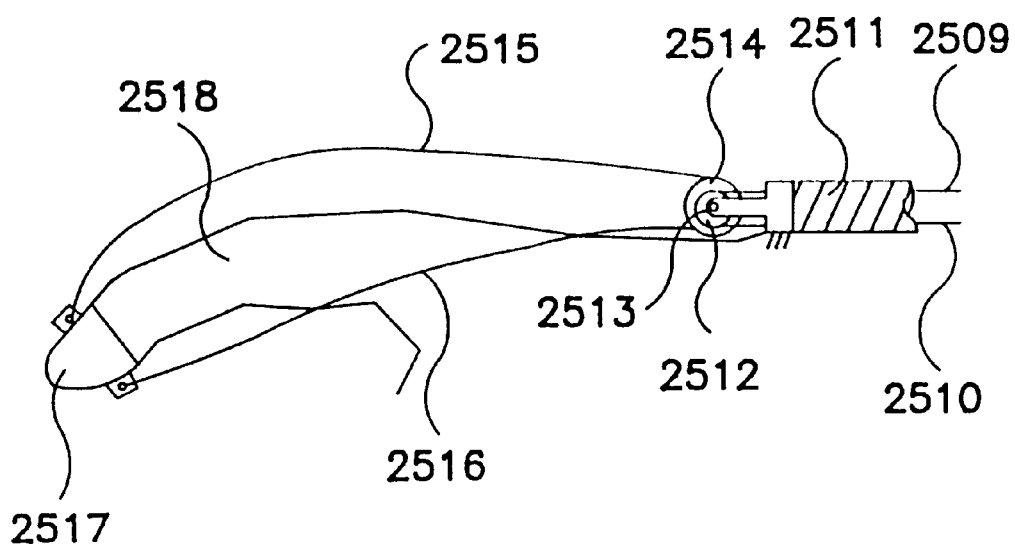

FIGS. 25A and 25B are diagrammatic illustrations of useful conversion of the movement of a circulating tendon loop. In FIG. 25A, a tendon loop comprising outgoing and return tendon portions 2500 and 2501, respectively, passes around input pulley 2503 which rotates about axis 2504 which is held stationary relative to tendon-guide structure 2502. Conveniently, the tendon-guide structure may be attached to a glove or hand with a finger 2508. Input pulley 2503 is connected to output pulley 2505 which affects fingertip force applicator 2507 via tendon 2506. A useful application employs such a structure to impart tension into tendon 2506 which pulls back on fingertip 2507. When tendon 2506 is stiff and appropriately guided, tendon 2506 may also be driven in compression, whereby a pushing force is applied to the fingertip 2507.

FIG. 25B is similar to FIG. 25A, where outgoing- and return-tendon portions 2509 and 2510 pass around input pulley 2512 which rotates about axis 2513 rigidly associated with tendon guide 2511. Input pulley 2512 is connected to output pulley 2514 which in FIG. 25B has a tendon loop 2515 passing around it. In this illustrative embodiment, two ends of the tendon are connected to the fingertip force applicator 2517 which contacts the fingertip. Using this structure, forces to resist or assist finger flexure may be applied with a non-rigid tendon, i.e., a tendon which only transmits tensile forces.

Figure 26:
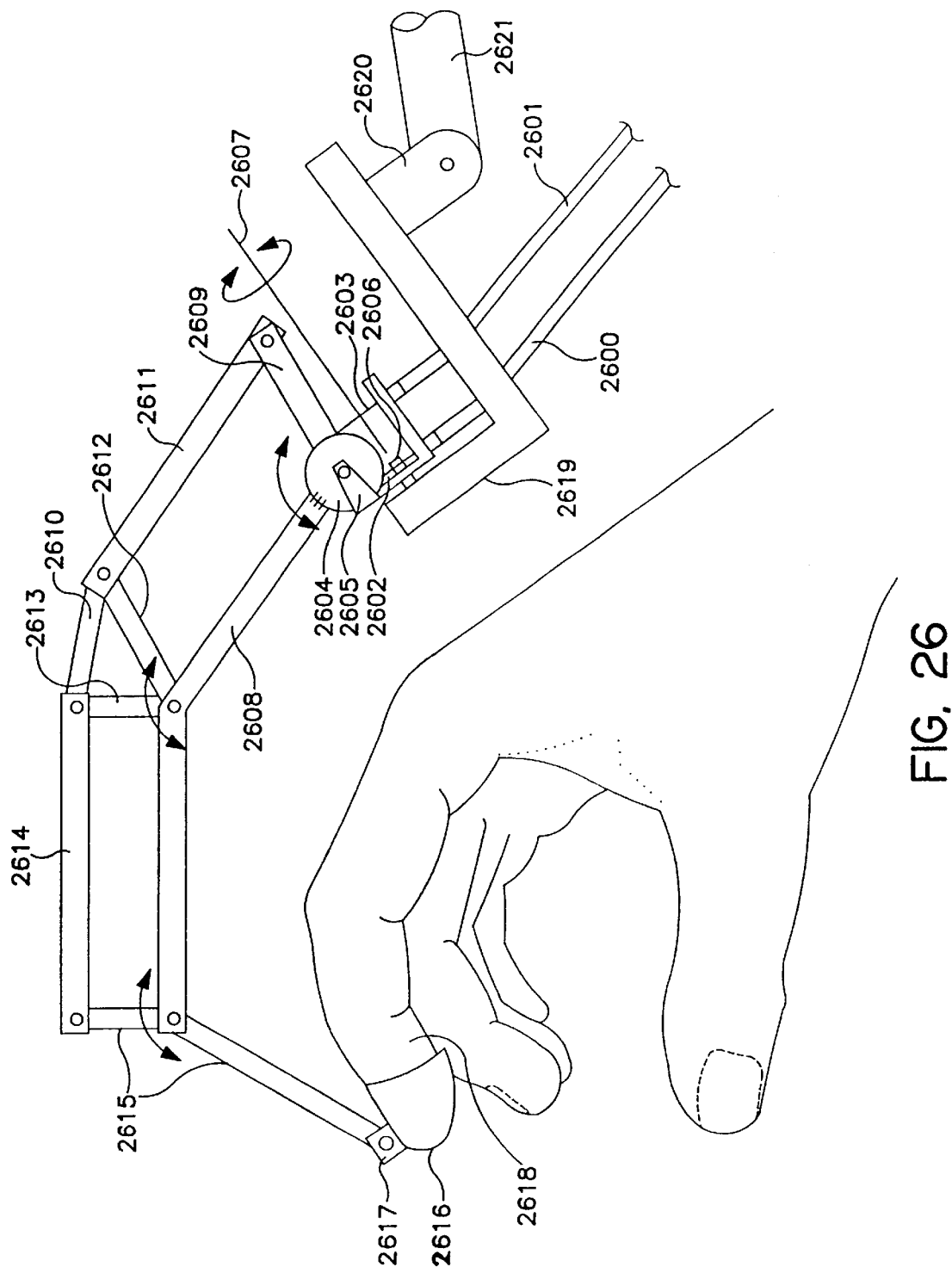
FIG. 26 is an illustrative embodiment, similar in structure to FIGS. 15C and 14, but where the pulley-support structure is not supported by the hand.

FIG. 26 is an illustrative embodiment, similar in structure to FIGS. 15C and 14, but where the pulley-support structure is not supported by the hand. Instead, the pulley-support structure may be connected to an immovable object, or to a moving object, such as a force- or position-programmable robotic arm. The robotic arm may be commanded to follow the hand such that the fingertips always remain within the workspace of the hand-linkage system, thus creating an effectively larger workspace than is inherent in the hand-linkage system. One advantage to this embodiment is that the user needs to only insert their fingertips into the device, i.e., they don't need to strap the device onto their metacarpus. This makes for quicker donning and doffing, removes reaction forces from non-intuitive portions of the hand, and promotes better hygiene. In FIG. 15C, the abduction axis shaft 1568, which in FIG. 26 is 2606, with axis 2607, is connected to mounting bracket 2619, rather than the hand backplate. In essence, the "backplate," may now move independently of the hand, and is shown to be positioned by a positioning mechanism, shown for example as comprising the two links 2620 and 2621. Such a positioning mechanism may be any robot-like device, such as a PUMA robot, a SensAble Technologies Phantom, and the like.

Figure 27:
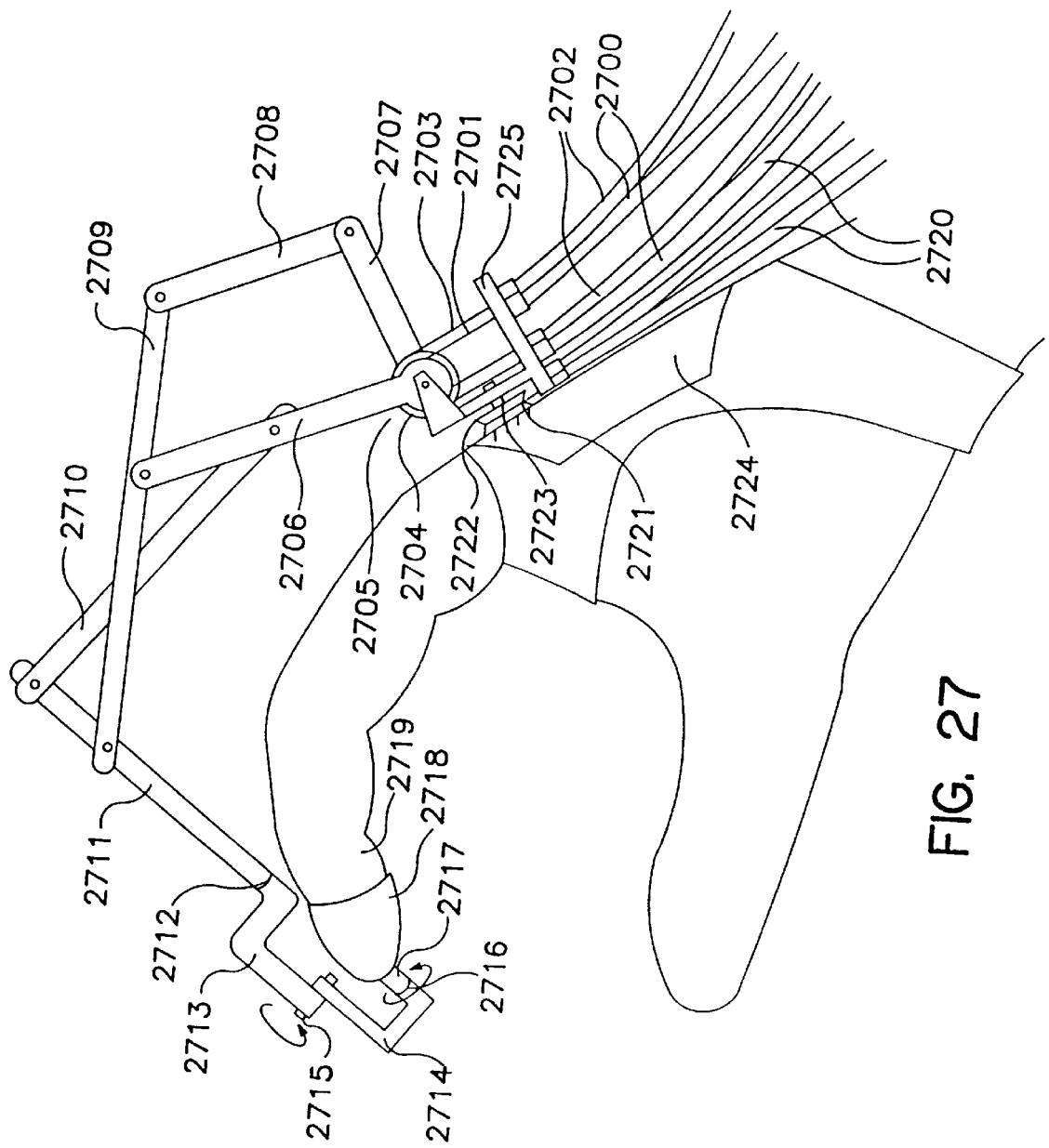
FIG. 27 is similar in principle to FIG. 26, with the main difference being the replacement of the variation on the 5-bar linkage with a 7-bar linkage.

The remainder of the structure of FIG. 26 operates as follows. The device is a variation on a 5-bar linkage where two of the bars, i.e., links 2609 and 2608 are position controllable. The position of these two links uniquely determines the position of the endpoint 2617 of link 2615. The structure was chosen since it permits a wide range of hand formations without binding. Tendon portions 2603 and 2602 are transmitted to the device via tendon guides 2601 and 2600, respectively. These tendons guides may be of any convenient form for transmitting tendon tension, including but not limited to the techniques described in FIGS. 21, 22A–22E, 23A–23D, and the like. The transmitted tendon portions pass around pulley 2604, thus affecting its rotational position. Pulley 2604 is rigidly attached to link 2608. Similarly, there is another tendon-guide structure directly behind the one just described, such that it does not appear in this side-view illustration, but where the associated pulley affects the orientation of link 2609. The three links 2613, 2610 and 1612 are all pinned at their ends, such that movement of link 2611 relative to link 2608 causes link 2614 to move relative to link 2608, hence, moving link 2615. As shown, the end of link 2615 is connected to fingertip force-applying means 2616 which applies force, and optionally other sensing signals, to the fingertip 2618. The coupling between link 2615 to fingertip force applying means 2616 is shown schematically as a pinned joint for simplicity; however, the attachment is typically more complex. The attachment may comprise a ball joint, a gimbal, other jointed structure, flexible coupling, and the like. FIG. 27 provides a diagrammatic illustration of a particularly useful gimbal-like structure which may be used for FIG. 26 or any other appropriate figure. For clarity in FIG. 26, the abduction-controlling mechanism typically associated with shaft 2606 is not shown. An illustrative example of such an abduction-controlling mechanism is provided by FIG. 27, where tendon 2721 is guided to the device by guides 2720, and passes around pulley 2722, which in FIG. 27 is attached to the backplate, but is attached to the mounting bracket 2619 in FIG. 26 (again, not shown).

As just discussed, FIG. 27 is similar in principle to FIG. 26, with the main difference being the replacement of the variation on the 5-bar linkage with a 7-bar linkage. The 7-bar linkage as shown provides an different trajectory for link 2711 (compare with link 2615 in FIG. 26) given angles of links 2706 and 2707 (compare with links 2608 and 2609 in FIG. 26). Obviously, in FIG. 27 the pulley structure is attached to the hand backplate, but it can also be suspended by a fixed or movable object as was explicitly shown in FIG. 26. In fact, any such figures with a pulley structure may be interchangeably mounted to the hand backplate or to a fixed or movable structure without departing from the scope of this invention. Similarly, any feedback structures shown for a single finger may be replicated for multiple fingers.

FIG. 27 does provide a slight perspective view to the point where a second pulley may be seen. Tendon guides 2700 transmit tendon 2701 from a force generator (not shown). The force generator may comprise any convenient force- or position-generating means, such as the motor and spool apparatus provided in FIG. 19. The force generator may also comprise a voice coil, a solenoid, nickel-titanium alloy wire (Nitinol), pneumatic motor, hydraulic motor, electric motor, and the like. The tendon 2701 passes around pulley 2704 which is attached to link 2706. Similarly, tendon guides 2702 transmit tendon 2703 which passes around pulley 2705 which is attached to link 2707. The remaining structure is self-evident from the figure, which provides the pinned connections for links 2706, 2707, 2708, 2709, 2710 and 2711. The remainder of the structure implements a gimbal, where link 2711 is connected by axial joint 2712 to link 2713, which is connected by a revolute joint 2715 to link 2714, which is connected by an axial joint 2716 to link 2717 which is rigidly attached to force applicator 2718 which applies forces, and optionally other sensory stimulations such as texture, temperature, pressure, moisture, and the like to the fingertip 2719. Pulley-support structure 2725 pivots about axis 2723 to provide abduction/adduction capability. Tendon guides 2720 transmit the tendon 2721 which passes around the pulley 2722 which is attached to the hand backplate, but which rotates freely relative to axial joint 2723. By routing tendons to the hand to rotate the pulleys, rather than placing motors directly on the hand, or in close proximity to the pulleys, space is conserved and multiple linkage assemblies may be stacked side by side to accommodate multiple fingers.

Figure 28:
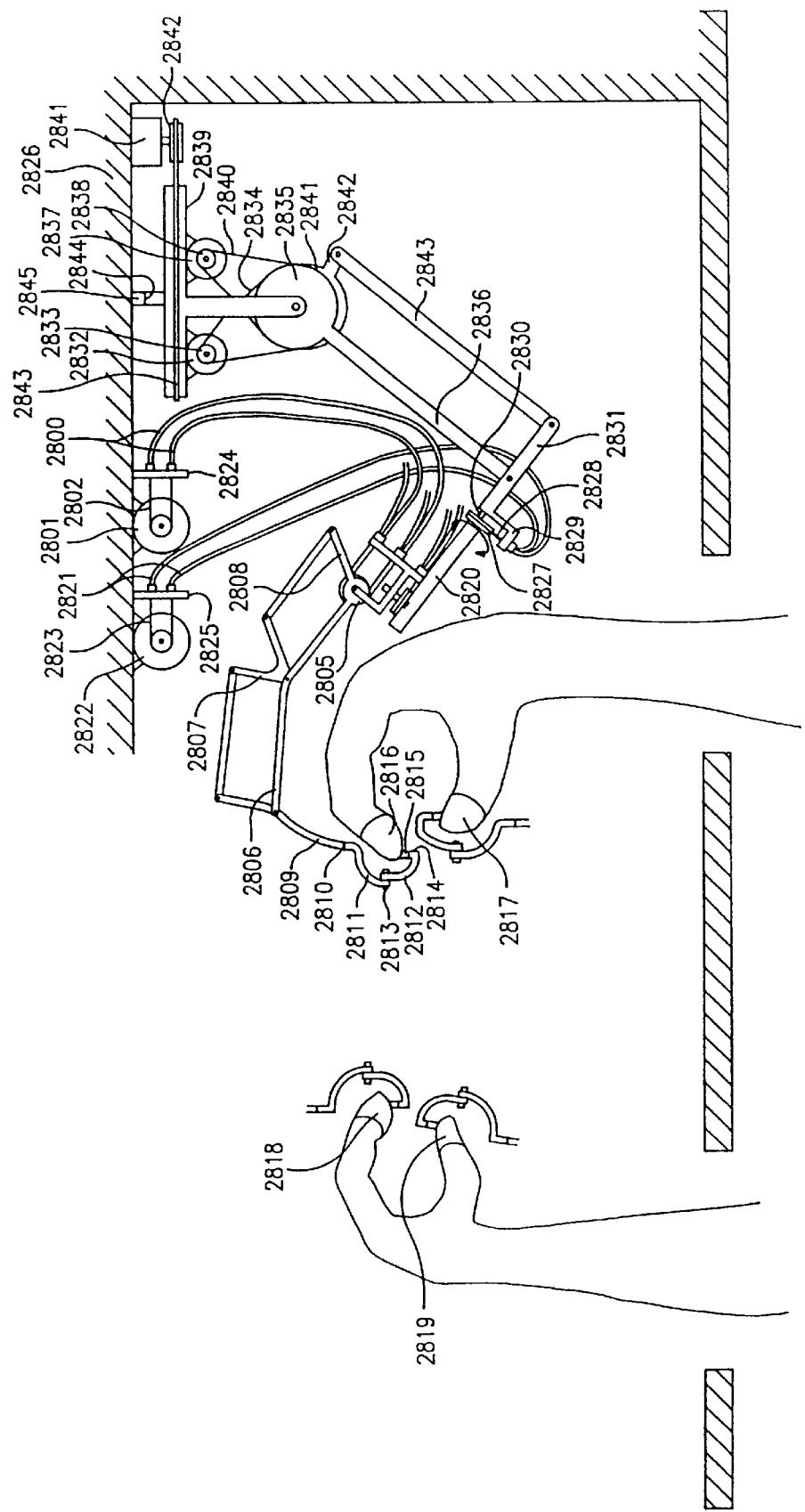
FIG. 28 is a diagrammatic illustration extending the structure of FIG. 26 to two hands, and where a force-programmable robot is shown.

FIG. 28 is a diagrammatic illustration extending the structure of FIG. 26 to two hands, and where a force-programmable robot is shown. FIG. 28 was drawn to illustrate the concept of a "micro" manipulator providing force and position control to the hand for subtle hand movements, and where a larger "macro" manipulator periodically or continually readjusts the placement of the micro-manipulator such the user's hand always remains in the usable workspace of the micro-manipulator. As shown, the fingertip force applicators are accessible via inserting one's hands into openings in a reference structure; however, the entire micro/macro assembly may also reside on a desk top.

For brevity, and since much of the underlying details of FIG. 28 have already been described or are obvious from the figure, only the differences and highlights will be further discussed here. The majority of the micro-manipulator as shown comprises another variation of a 5-bar linkage (comprising links 2808, 2807, 2806, 2809, 2811, 2812 and 2815, and further comprising joints 2810, 2813 and 2814, and further comprising pulley 2805, and further comprising fingertip force-applicator 2816), which is very similar to the variation described in FIG. 26, but where "V-shaped" link 2807 replaces the three links 2613, 2610 and 2612. The structure of FIG. 28 explicitly provides the abduction-controlling mechanism provided explicitly by FIG. 27. FIG. 28 also explicitly provides the fingertip force-controlling gimbal-like mechanism provided by FIG. 27. For clarity, only the terminal portion of other such feedback structures are shown attached to the thumb fingertip of the right hand and the index fingertip and thumb fingertip of the left hand. Obviously, the device and concept may be extended to further fingertips.

Motor 2801 is attached to a reference structure 2826, where the motor imparts tension to tendon loop 2802, where the tendon loop is guided by tendon guides 2800 which are affixed at one end to guide bracket 2824 which is further attached to the reference structure 2826. The other end of the tendon guides is attached to the pulley support structure associated with the 5-bar linkage assembly, and the tendon loop emerges and passes around pulley 2805. There is obviously another motor-tendon-guide assembly which drives the pulley associated with the other link of the 5-bar mechanism.

Motor 2822 is attached to a reference structure 2826, where the motor imparts tension to tendon loop 2823, where the tendon loop is guided by tendon guides 2821 which are affixed at one end to guide bracket 2825 which is further attached to the reference structure 2826. The other end of the tendon guides is attached to positioning bracket 2829, and the portion 2828 of the tendon loop that emerges from the guides near this bracket passes around pulley 2827 which is attached to mounting bracket 2820. When motor 2822 rotates its shaft, mounting bracket 2820 is caused to rotate about axial joint 2830 relative to positioning bracket 2829.

The macro-manipulator comprises two motors 2832 and 2837 mounted to rotating disk 2839. This disk rotates about axial joint 2844 relative to base link 2845 attached to a reference location. Motor 2841 has pulley 2842 which drives the rotation of disk 2839 via tendon loop 2843. When the disk 2839 rotates, so do both motors 2832 and 2837. These motors drive pulleys 2841 and 2835 via tendon loops 2834 and 2840, respectively. Typically, the motors 2832 and 2837 are placed as close to the axis of joint 2844 as possible to minimize the rotational inertia which motor 2841 needs to overcome. Pulley 2835 is connected to link 2836, and pulley 2841 is connected to link 2843, which links are attached to link 2831, from which positioning bracket 2829 projects. While the macro-manipulator just described provides one force- and position-programmable robotic arm, any appropriate robotic-like device, with the desired number of degrees of freedom may be used. The robotic arm as shown provides four degrees of freedom, which is sufficient for some applications, although other application may require more.

Figure 29:
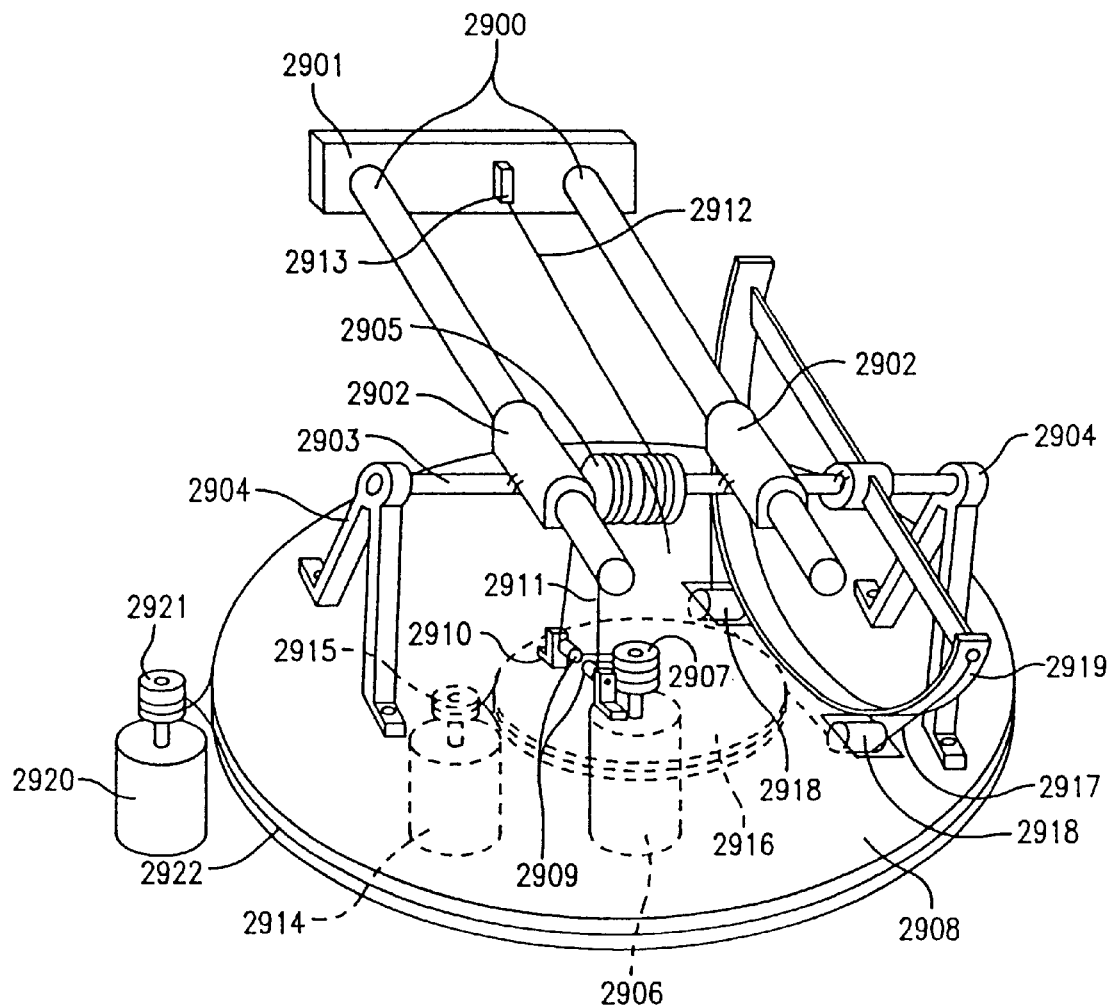

FIG. 29 is a diagrammatic illustration showing a force- and position-programmable robotic arm which may be used as a macro-manipulator, or as a grounded-force device which attaches to the grasp-force device of FIG. 1, and the like. Rods 2900 are supported by bearings 2902 which are attached to a shaft 2903 which pivots relative to shaft supporting members 2904 which are further attached to rotating disk 2908. One end of the pair of rods is attached to an end plate 2901. A tendon-guiding spool 2905 rotates freely on the shaft 2903. An extension tendon 2912 passes from one end plate 2901, around the tendon-guiding spool 2905 and is terminated at its other end at a second end plate which isn't shown. On the end plate 2901, the tendon 2912 is terminated at a tensioning block 2913. The other end of the rods and tendon, along with the other end plate, have been removed from the drawing to expose the underlying mechanism. As spool 2905 rotates, it provides tension to the tendon 2912, causing the rods and end-plate structure to translate relative to the shaft 2903.

The motor 2906 (underneath the plate 2908), has its rotational axis aligned with the rotational axis of the plate. As the spool 2907 which is connected to the motor shaft rotates, the tendon loop 2911 is caused to move. This tendon 2911 passes around the spool 2907, around tendon-guiding-idler pulleys 2909 (which are attached to plate 2908 via support structures 2910), and passes around the tendon-guiding spool 2905. Thus, as the motor 2906 rotates, the spool 2905 rotates, and so the rods translate.

The motor 2914 has a pulley 2915. Idler pulley 2916 rotates coaxially with the axis of the motor 2906 and plate 2908. Elevation pulley 2919 is attached to the shaft 2903. Elevation tendon 2917 is attached at the near end of elevation pulley 2919, passes down and around the near elevation-guide pulley 2918, passes counterclockwise around idler pulley 2916, passes clockwise around motor pulley 2915, continues on to pass around the idler pulley 2916 again, passes under the far elevation-guide pulley 2918, up the far side of the elevation pulley 2919, and if finally anchored at the top of the far side of the elevation pulley 2919. Thus, when the motor 2914 rotates, the elevation pulley rotates, and the rods change their angle of elevation.

The motor 2920 has a pulley 2921 which drives the plate 2908 to turn via tendon 2922. Thus, when motor 2920 turns, the rods also turn about the axis aligned with the axis of motor 2906. Note that various support details for the plate 2908 have also been eliminated from the figure for clarity. One advantage of this design is that is requires no translation of any of the motors, thus inertia is minimized. Various modification to the design may be conveniently made, such as the rods may be one over the other. Various rod cross sections may be employed, including triangular and rectangular. Various bearing constructions may be used, such as roller wheels, each position at 120 degrees orientation relative to the other, with the rod passing through the projected vertex of the roller wheels.

Figure 30:
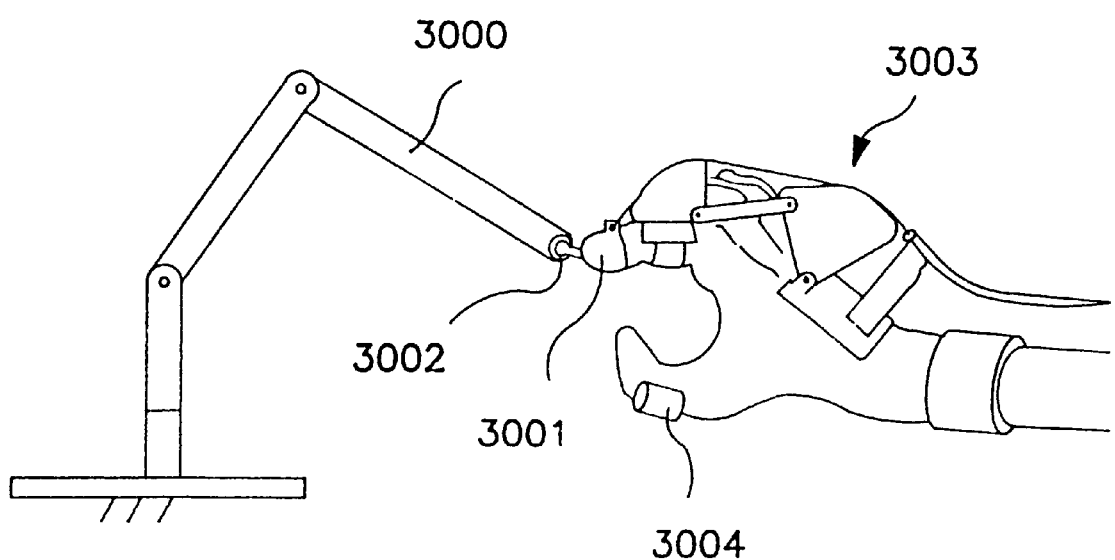
FIG. 30 is a diagrammatic illustration of a hand-feedback device, such as provide by FIG. 1, and the like, being attached at the fingertip to a force- or position-programmable robot arm by a coupler.

FIG. 30 is a diagrammatic illustration of a hand-feedback device 3003, such as provide by FIG. 1, and the like, being attached at the fingertip 3001 to a force- or position-programmable robot arm 3000 by a coupler 3002. Such an arm may be any appropriate robotic-like arm, such as a PUMA arm, a Phantom arm by SensAble Technologies, and the like. The hand feedback device may comprise any type of feedback, for example grasp forces which are local to the hand, such as is provided by the device of FIG. 1. The hand-feedback device may also comprise tactile elements, for instance on or more vibratory elements 3004, such as are provided by the CyberTouch product manufactured by Virtual Technologies, Inc. In the case of vibratory feedback, the robotic arm would provide the ground-referenced force to one or more fingers, while the tactile-feedback elements provided tactile feedback to the same or other fingers. By using the robotic arm along with the hand-referenced grasp-force-feedback device of FIG. 1, again, ground-referenced forces can be applied to one or more fingers, while forces on the fingers relative to the hand can be applied to the same or other fingers. The robotic-like device may be attached to any portion of the hand to provide ground-referenced forces and positioning. The location of attachment to the hand affects the sensory perception. The robotic-like device may also provide absolute location information for the hand.

Figure 31:
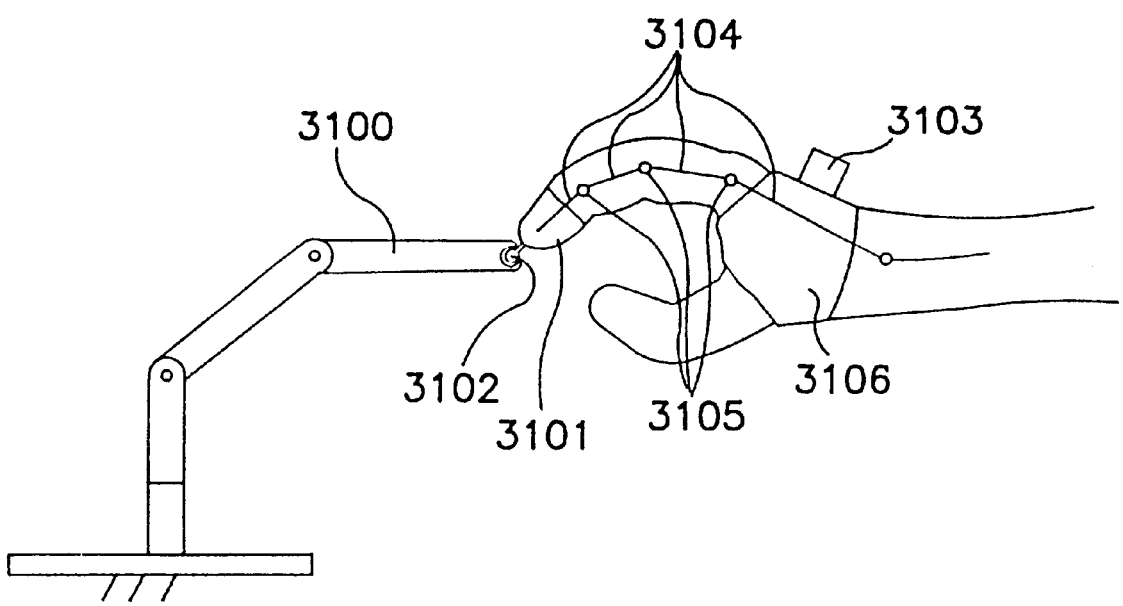
FIG. 31 is a diagrammatic illustration of a fingertip of a hand being positioned by a robotic-arm-like device, connected to the force-applying device via a coupler.

FIG. 31 is a diagrammatic illustration of a fingertip of a hand being positioned by a robotic-arm-like device 3100, connected to the force-applying device 3101 via a coupler 3102. Here it is assumed that the position of the point of attachement of the robot arm to the hand is known from the robot arm. Associated with the hand is an alternate position-sensing device, such as an electromagnetic 6-DOF-positioning device 3101 manufactured by Polhemus, Inc. or Ascension Technology Corp, both located in Vermont. As shown, the position-sensing device 3103 is supported on the hand by support 3106. If the hand is modeled as a set of links 3104 interconnected by constant-axis revolute joints 3105, then by using the position of the fingertip from the robot arm, and the position of the metacarpus from the 6-DOF position-sensing device, and using an inverse kinematic mathematical determination as described in U.S. Pat. No. 5,676,157, the joint angles 3105 can be determined. Once these joint angles are determined, using forward kinematics, a graphical hand can be displayed on a computer screen which mimics the movements of the hand and finger.

Figures 32A, 32B:
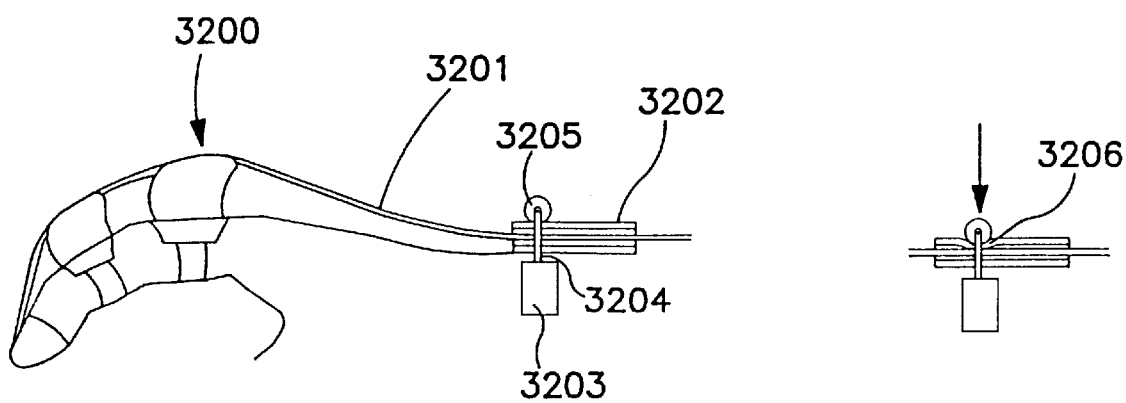
FIGS. 32A and 32B are diagrammatic illustrations of a movement-impeding apparatus.

FIGS. 32A and 32B are diagrammatic illustrations of a movement-impeding apparatus. The figures show such an apparatus in combination with a portion of the grasp-force-feedback device 3200 such as is provided in FIG. 1, and the like. As shown in FIG. 32A, when the finger is flexed, tendon 3201 slides relative to guide 3202 which is typically attached to a glove or hand. As shown in FIG. 32B, to impede movement of the finger, actuator 3203 is activated, withdrawing rod 3204 and element 3205, such that guide 3206 collapses onto the tendon 3201, opposing its movement relative to the guide, or even preventing it from further moving relative to the guide altogether. Actuator 3203 may be any convenient actuator such as a solenoid, voice coil, motor, and the like. If tendon 3201 is stiff, actuation of actuator 3203 can also prevent the finger from extending. In general, the entire actuator may be replaced with a more conventional brake- or clutch-like mechanism which impedes or prevents movement.

Figure 33B:
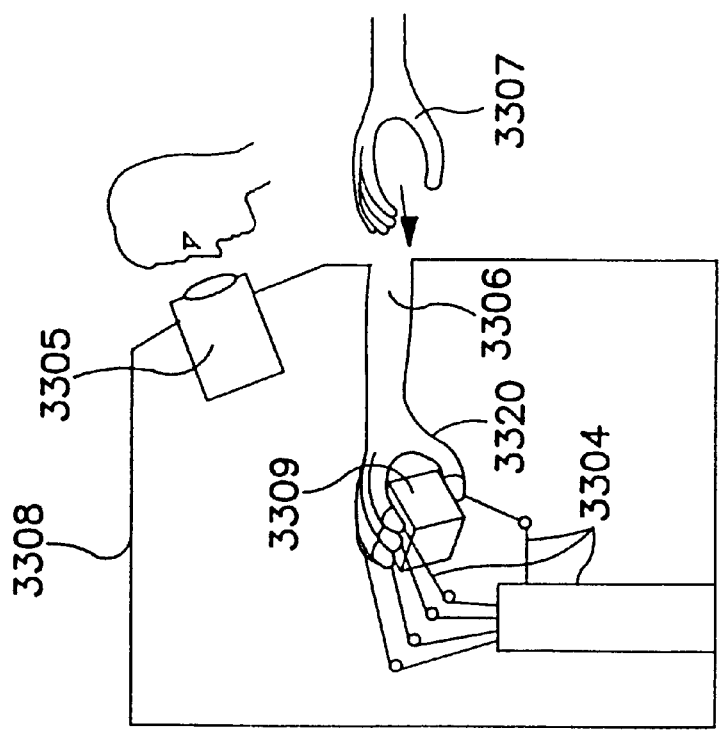
Figure 33A:
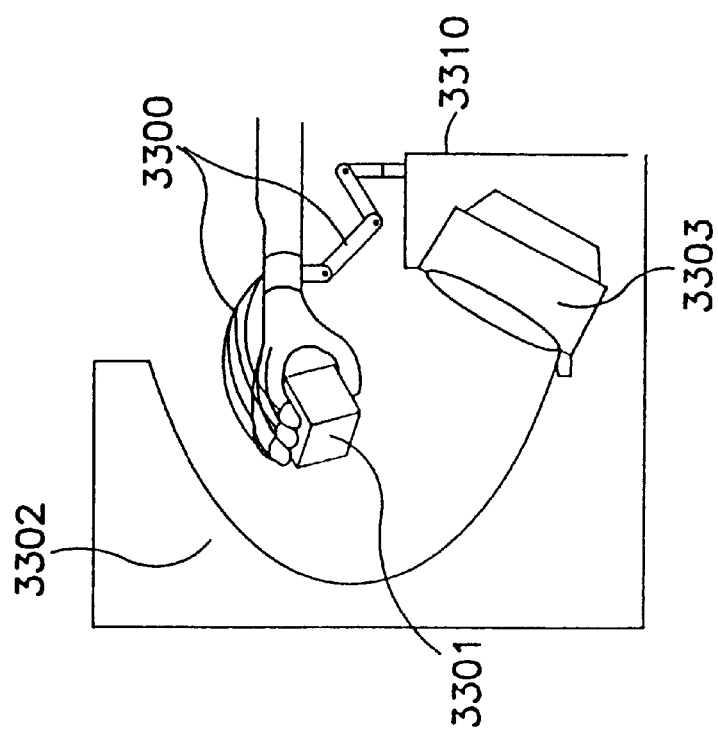

FIGS. 33A–33D are diagrammatic illustrations a canonical force-feedback system, representing any of the force-feedback embodiments described in the subject application, being used with a 3D display system. FIG. 33A shows the canonical force-feedback system 3300 being used with a display system employing a computer monitor 3303 projecting onto a parabolic mirror 3302. Due to the optical effects of the parabolic mirror, a virtual image 3301 of what is displayed on the monitor will appear in 3D at the focal point of the mirror. Thus, without any further viewing requirements, the user perceives that they are manipulating the virtual object with their hand which is wearing the canonical force-feedback equipment.

FIG. 33B is a diagrammatic illustration of a canonical force-feedback system 3304 attached to a glove 3320 which is further attached to the opening 3306 in a viewing structure 3308. The glove has enough structure that it maintains its form, even without the presence of a hand in it. Such a glove can be made from rubber, plastic, neoprene, and the like. Although a variety of viewing systems may be used, the one discussed here 3305 comprises one or more computer monitors or TVs, with appropriate optics in front to give, the perception that the object displayed on the screen is behind the display. Such display technology is common place for head-mounted displays known to those skilled in the art of virtual reality. The display gives the viewer the perception that the object they see is real and resides within the viewing structure 3308. Associated with the glove 3320 are sensors such that the configuration of the hand is known by a computer (not shown). The computer displays for the user a graphical representation of their hand 3307, along with the object 3309, and performs collision and force calculations between the hand and object, and displays the forces on the hand by the canonical force-feedback system. Such a viewing-feedback system finds utility in museums and the like where people need to quickly insert and remove their hands from the device.

FIG. 33C is a diagrammatic illustration of a canonical force-feedback system 3321 being used below a mirror 3311 where the user inserts their hand under the mirror at location 3319. A computer monitor 3312 supported by support structure 3314 projects an image onto the mirror which reflects to the eyes of the user. The monitor may alternate displaying views slightly offset to the left and right (corresponding to the different images seen by one's eyes) of images of the virtual hand (calculated as before using measurements of the physical hand) and virtual object 3322, then by synchronizing LCD glasses 3313 with the alternating left-right-shifted views, the viewer receives a 3D stereoscopic perception. Such LCD glasses viewing technology is provided by Crystal Eyes®. Thus the viewer perceives that they are manipulating a real object beneath a pane of glass.

FIG. 33D is similar in concept to FIG. 33C, however, the monitor-mirror combination is replaced by a flat-panel display 3315 atop support structure 3316. Again, left-right-eye views are alternated and synchronized with LCD glasses 3317, giving the viewer a stereoscopic perspective that there is a real object under 3318 the counter top which they are manipulating. A computer (not shown) calculates the views and forces associated with the canonical force-feedback device and the virtual object.

Figure 34:
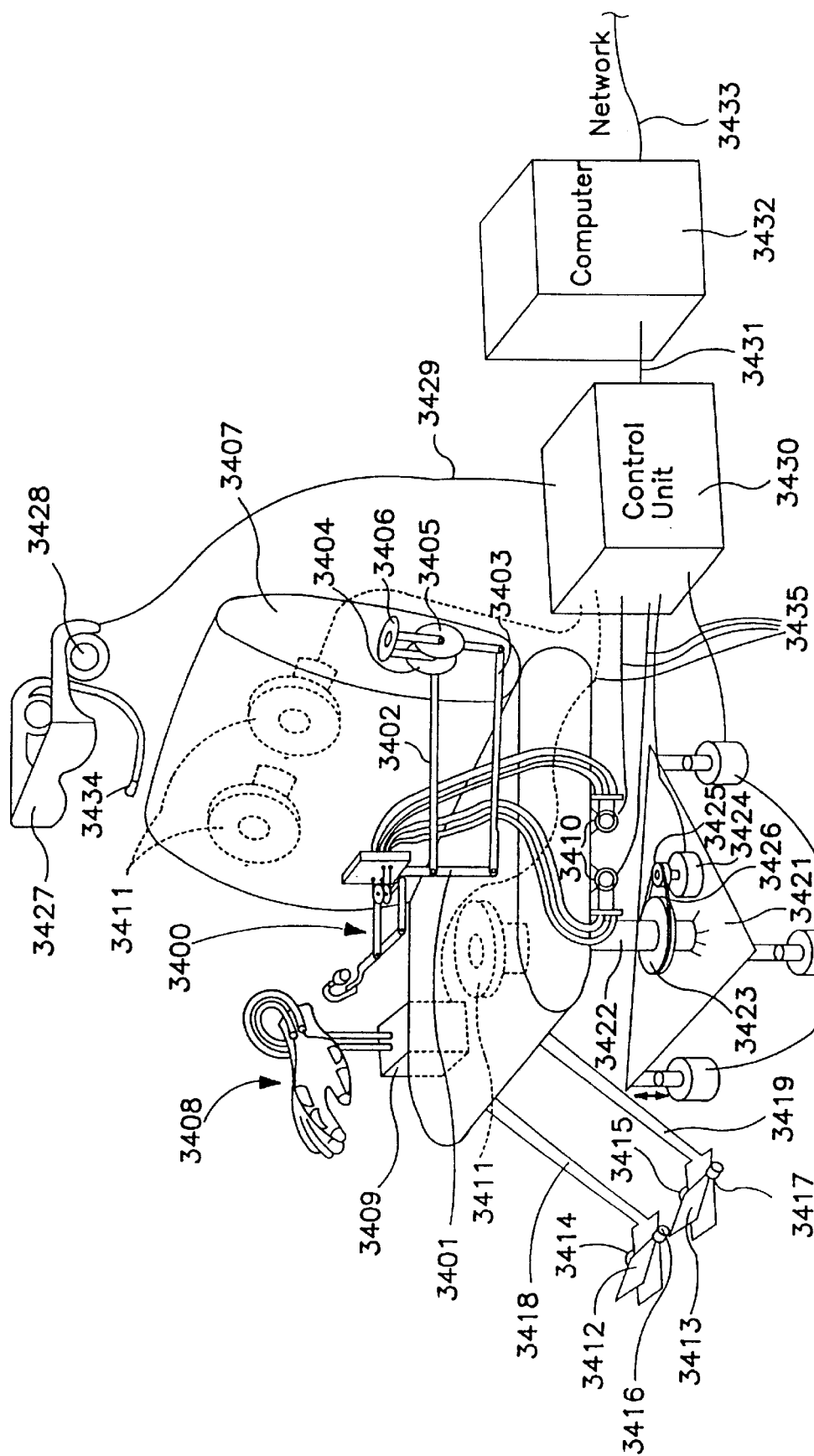
FIG. 34 is a diagrammatic illustration of a simulation chair.

FIG. 34 is a diagrammatic illustration of a simulation chair 3407. The chair finds use in entertainment, military training, flight and driving draining, and the like. The chair may include any of our force-feedback devices described in the subject application. In addition, the chair may incorporate a head-mounted display 3427, motion platform 3421, steering/moving pedals 3412 and 3413, headphones 3428, microphone 3434, vibration-inducing speakers 3411, a control unit 3430, a computer 3432, interconnects 3431, 3429 and 3435, a network connection 3433, and the like. As shown to exemplify the concept, a micro/macro feedback device 3402 similar to that provided in FIG. 28 is attached to the left side of the chair. The macro part of the feedback device comprises pulleys 3405, 3406 and 3404 to provide elevation, extension and rotation of the micro part. For clarity, details of the attachment means and actuation means for the macro-manipulator are not shown. To the end of the macro-manipulator is attached a micro-manipulator 3400 driven by motors 3410, and others which are not shown. Again, to exemplify the concept, a grasp-force-feedback device 3408 similar to that provided by FIG. 1, and the like, is shown connected to the right side of the chair seat. Any appropriated feedback device may be used with either hand. Other navigational aids such as a joystick, SpaceBall®, trackball, and the like may also be positioned near the chair. The steering pedals 3412 and 3413 are connected to legs 3418 and 3419. Angle measuring means 3414 and 3417, such as encoders, flex sensors and the like determine pedal angles. The pedals 3412 and 3413 also may have return springs 3416 and 3415 to keep the pedals extending up. The motion base may be any suitable technique for modifying the position and orientation of the chair. To exemplify the concept, a motion platform with three controllable elevating motors 3420 is shown. By appropriately energizing one or more of the motors, a variety of tilts can be effected. The motors may be any appropriate actuator, including electrical motors, pneumatic motors, hydraulic motors, voice coils, solenoids and the like. A motor 3424 is used to rotate the chair relative to the motion base. The motor has a pulley 3425 which is connected via tendon loop 3426 to chair pulley 3423 which turns chair post 3422 to which the chair cushion 3407 is attached.

Figure 35:
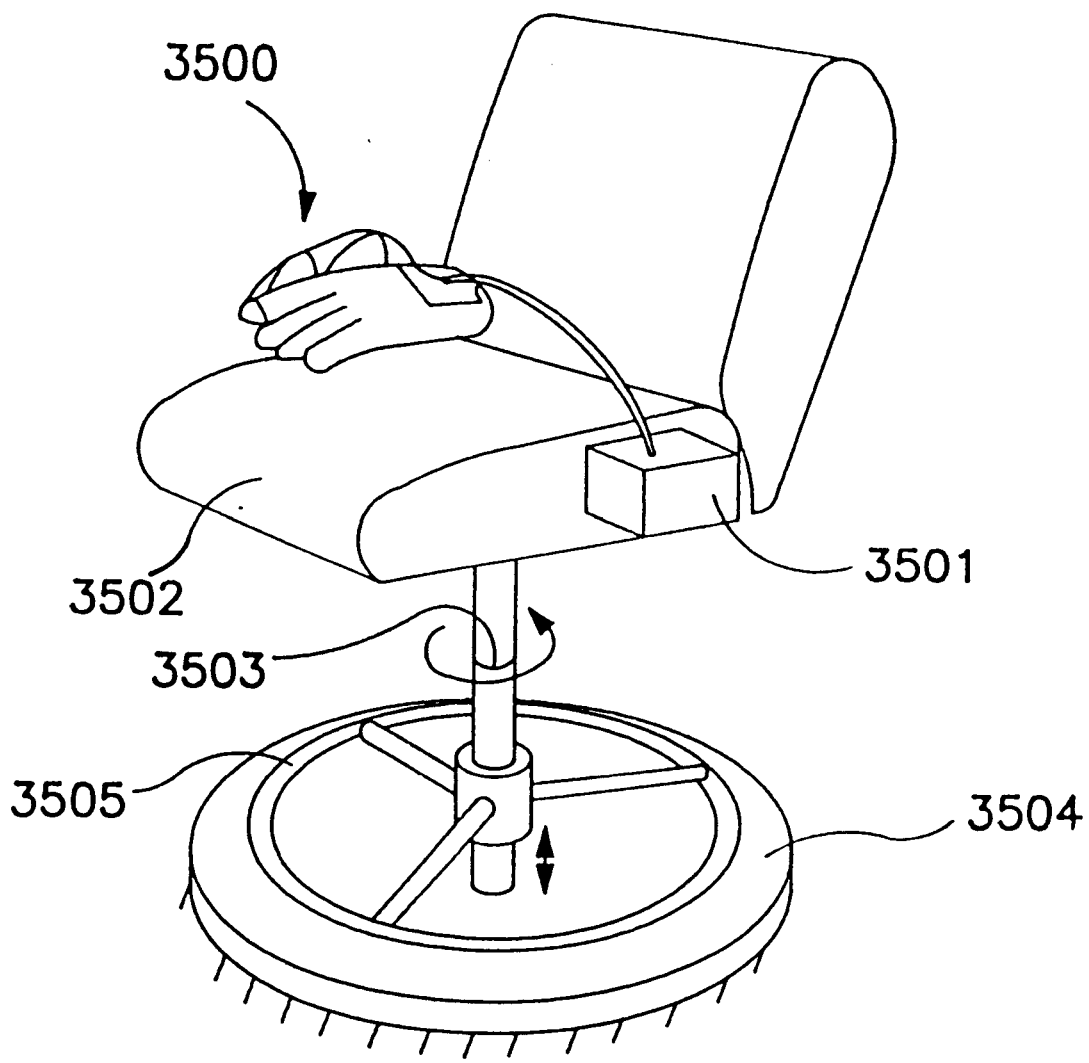
FIG. 35 is a diagrammatic illustration of a variant on the simulation chair of FIG. 34.

FIG. 35 is a diagrammatic illustration of a variant on the simulation chair of FIG. 34. In FIG. 35, the chair 3502 again comprises any of the feedback devices described in the subject application, where for purpose of example, the grasp-force feedback device of FIG. 1 3500 is shown with actuator module 3501 mounted to the side of the chair. The chair of FIG. 35 may contain any of the components and features of the chair of FIG. 34; however, the method of navigation is different. Rather than the steering/forward pedals 3412 and 3417 of FIG. 34, a "barstool" bar 3505 is employed to control forward movement. The chair 3502 is able to rotate about the axial joint 3503 relative to the base 3504. Typically the rotation is effected by human power, i.e., pushing the chair with one's feet until the desired direction is determined. Once the direction is determined, the farther down the bar 3505 is pressed, the faster one moves in that direction.

All publications, patents, and patent applications mentioned in this specification are herein incorporated by reference to the same extent as if each individual publication or patent application was specifically and individually indicated to be incorporated by reference.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best use the invention and various embodiments with various modifications as are suited to the particular use contemplated. It is intended that the scope of the invention be defined by the Claims appended hereto and their equivalents.

What is claimed is:

1. A robotic force-feedback system, said system comprising:
    a force-feedback device for contacting a human hand having a sensing link connected to a non-sensing link with at least one sensing joint between the sensing and non-sensing links, said device comprising a force applicator adapted to apply a force to the sensing link;
    force application means for applying a generated force between said sensing link and said non-sensing link, said force application means comprising a moment-augmenting structure, a tendon elevated by said moment-augmenting structure, said tendon connected to said force applicator and capable of transmitting the generated force to the force applicator;
    a manipulator disposed at a location separated from said force-feedback device; and
    a communication link between said force-feedback device and said manipulator.

2. An interactive computer system comprising:
    first and second force-feedback interface devices for right and left hands of a human operator, each said interface device including means for sensing the force applied to at least one fingertip of a finger and generating a sensed applied force signal related to said sensed force, and means for controlling the fingertip force in response to said sensed applied force signal, wherein said fingertip force may vary as a function of finger position;
    a display device for presenting a graphic environment to said human operator; and
    simulation means receiving said sensed signals and information about said graphic environment and communicating feedback to said human operator as said human operator interacts with said graphic environment.

3. A robotic force-feedback system according to claim 1 wherein said device comprises a glove.

4. A force-feedback system according to claim 1 wherein the force applicator comprises a platform and wherein the platform may be moved from a first position displaced from the sensing link to a second position in contact with the sensing link.

5. An interactive computer system according to claim 2 wherein the computer system is a computer aided design system and wherein said graphic environment is a design environment.

6. A force-feedback system comprising:
    a device adapted to contact a human hand having a sensing link connected to a second link with at least one joint between the sensing link and the second link, the force-feedback device comprising a force applicator adapted to apply a force to the sensing link; and
    force application means for applying a generated force to the sensing link, said force application means comprising a moment-augmenting structure positionable on the human hand, a tendon elevated by said moment-augmenting structure, said tendon connected to said force applicator and capable of transmitting the generated force to the force applicator.

7. A force-feedback system according to claim 6 wherein the force application means applies a force between the sensing link and the second link.

8. A force-feedback system according to claim 7 wherein the second link is a non-sensing link.

9. A force-feedback system according to claim 6 wherein the joint is a sensing joint.

10. A force-feedback system according to claim 6 further comprising a force generator remote from the force applicator.

11. A force-feedback system according to claim 6 wherein the tendon is enclosed along at least a portion of its length by a casing.

12. A force-feedback system according to claim 6 wherein the force applicator comprises a force sensor capable of generating a signal related to the force applied to the sensing link.

13. A force-feedback system according to claim 12 further comprising a control system for controlling the generated force is response to the signal.

14. A force-feedback system according to claim 6 wherein the moment-augmenting structure comprises first and second elements connected by an articulation.

15. A force-feedback system according to claim 14 wherein the first and second elements move in the same plane.

16. A force-feedback system according to claim 6 wherein the moment-augmenting structure comprises a flexure-articulating component and an abduction articulating component.

17. A force-feedback system according to claim 16 wherein the moment-augmenting structure further comprises two revolute joints.

18. A force-feedback system according to claim 6 wherein the moment-augmenting structure comprises a member comprising means for attachment to an intermediate link between the sensing link and the second link.

19. A force-feedback system according to claim 6 wherein the force applicator comprises a platform.

20. A force feedback system according to claim 19 wherein the platform may be moved from a first position displaced from the sensing link to a second position in contact with the sensing link.

* * * * *